United States Patent
Pieprzyk et al.

(10) Patent No.: US 8,389,960 B2
(45) Date of Patent: Mar. 5, 2013

(54) MICROFLUIDIC DEVICES AND METHODS

(75) Inventors: Martin Pieprzyk, Menlo Park, CA (US); Geoff Facer, Lane Cove (AU); Timothy Woudenberg, Moss Beach, CA (US); Brian Fowler, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 13/295,028

(22) Filed: Nov. 11, 2011

(65) Prior Publication Data

US 2012/0261007 A1   Oct. 18, 2012

Related U.S. Application Data

(63) Continuation of application No. 12/688,462, filed on Jan. 15, 2010, now Pat. No. 8,058,630.

(60) Provisional application No. 61/145,459, filed on Jan. 16, 2009.

(51) Int. Cl.
*G01N 21/64* (2006.01)
(52) U.S. Cl. .................................. 250/459.1
(58) Field of Classification Search ............... 250/459.1
See application file for complete search history.

(56) References Cited

U.S. PATENT DOCUMENTS

| | | | |
|---|---|---|---|
| 6,540,895 B1 | 4/2003 | Spence et al. |
| 6,619,311 B2 | 9/2003 | O'Connor et al. |
| 6,885,982 B2 | 4/2005 | Harris et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,318,912 B2 | 1/2008 | Pezzuto et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |

(Continued)

FOREIGN PATENT DOCUMENTS

| | | |
|---|---|---|
| CN | 1997454 B | 6/2010 |
| WO | 01/67369 A2 | 9/2001 |

(Continued)

*Primary Examiner* — Kiho Kim
(74) *Attorney, Agent, or Firm* — Kilpatrick Townsend & Stockton LLP

(57) ABSTRACT

Embodiments of the present invention provide improved microfluidic devices and related apparatus, systems, and methods. Methods are provided for reducing mixing times during use of microfluidic devices. Microfluidic devices and related methods of manufacturing are provided with increased manufacturing yield rates. Improved apparatus and related systems are provided for supplying controlled pressure to microfluidic devices. Methods and related microfluidic devices are provided for reducing dehydration of microfluidic devices during use. Microfluidic devices and related methods are provided with improved sample to reagent mixture ratio control. Microfluidic devices and systems are provided with improved resistance to compression fixture pressure induced failures. Methods and systems for conducting temperature controlled reactions using microfluidic devices are provided that reduce condensation levels within the microfluidic device. Methods and systems are provided for improved fluorescent imaging of microfluidic devices.

16 Claims, 34 Drawing Sheets

U.S. PATENT DOCUMENTS

| | | | |
|---|---|---|---|
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 8,058,630 B2 | 11/2011 | Pieprzyk et al. |
| 2002/0005493 A1 | 1/2002 | Reese et al. |
| 2002/0023684 A1 | 2/2002 | Chow |
| 2004/0180377 A1 | 9/2004 | Manger et al. |
| 2005/0053952 A1 | 3/2005 | Hong et al. |
| 2005/0072946 A1 | 4/2005 | Studer et al. |
| 2005/0084421 A1 | 4/2005 | Unger et al. |
| 2005/0201901 A1 | 9/2005 | Grossman et al. |
| 2005/0214173 A1* | 9/2005 | Facer et al. ............. 422/100 |
| 2005/0252773 A1 | 11/2005 | McBride et al. |
| 2006/0172408 A1 | 8/2006 | Quake et al. |
| 2006/0188906 A1 | 8/2006 | Kim et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0029169 A1 | 2/2008 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0257920 A1 | 10/2009 | Facer et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |
| 2011/0002812 A1* | 1/2011 | Asogawa et al. ............ 422/68.1 |

FOREIGN PATENT DOCUMENTS

| | | |
|---|---|---|
| WO | 2007/033385 A2 | 3/2007 |
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |

* cited by examiner

Dynamic Array Schematic

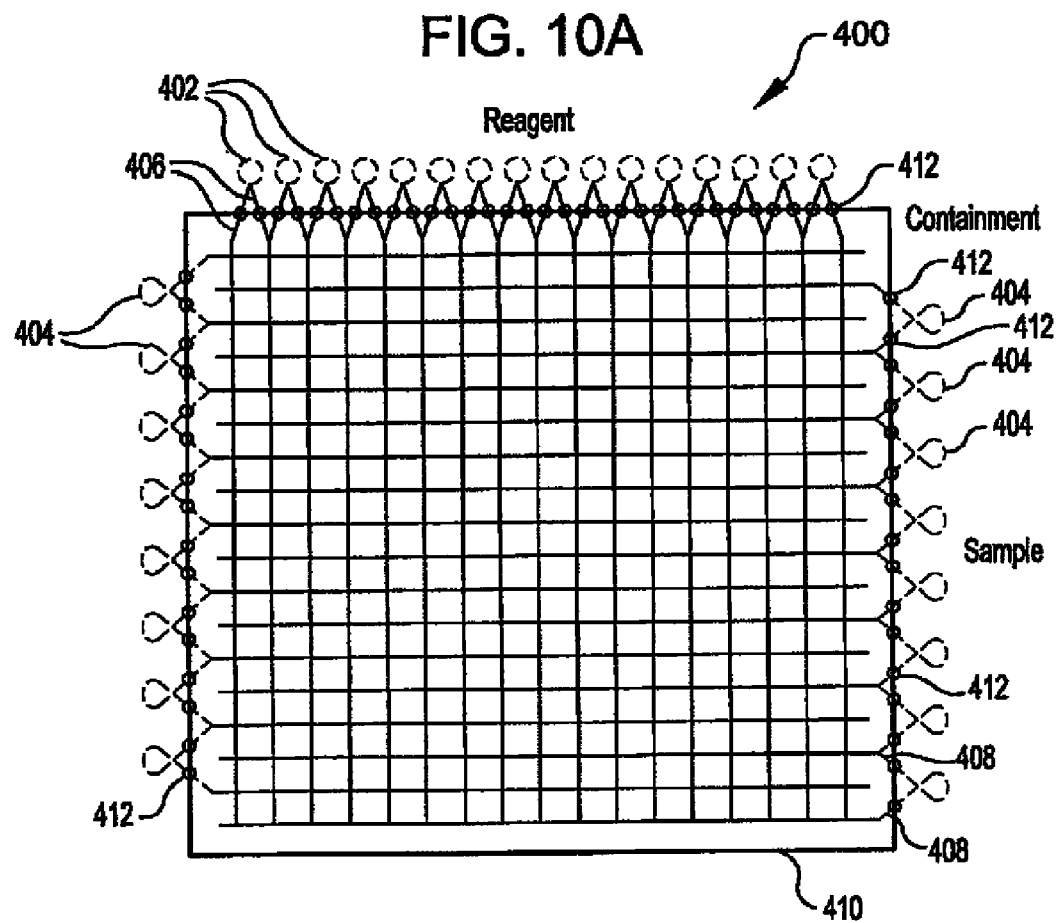

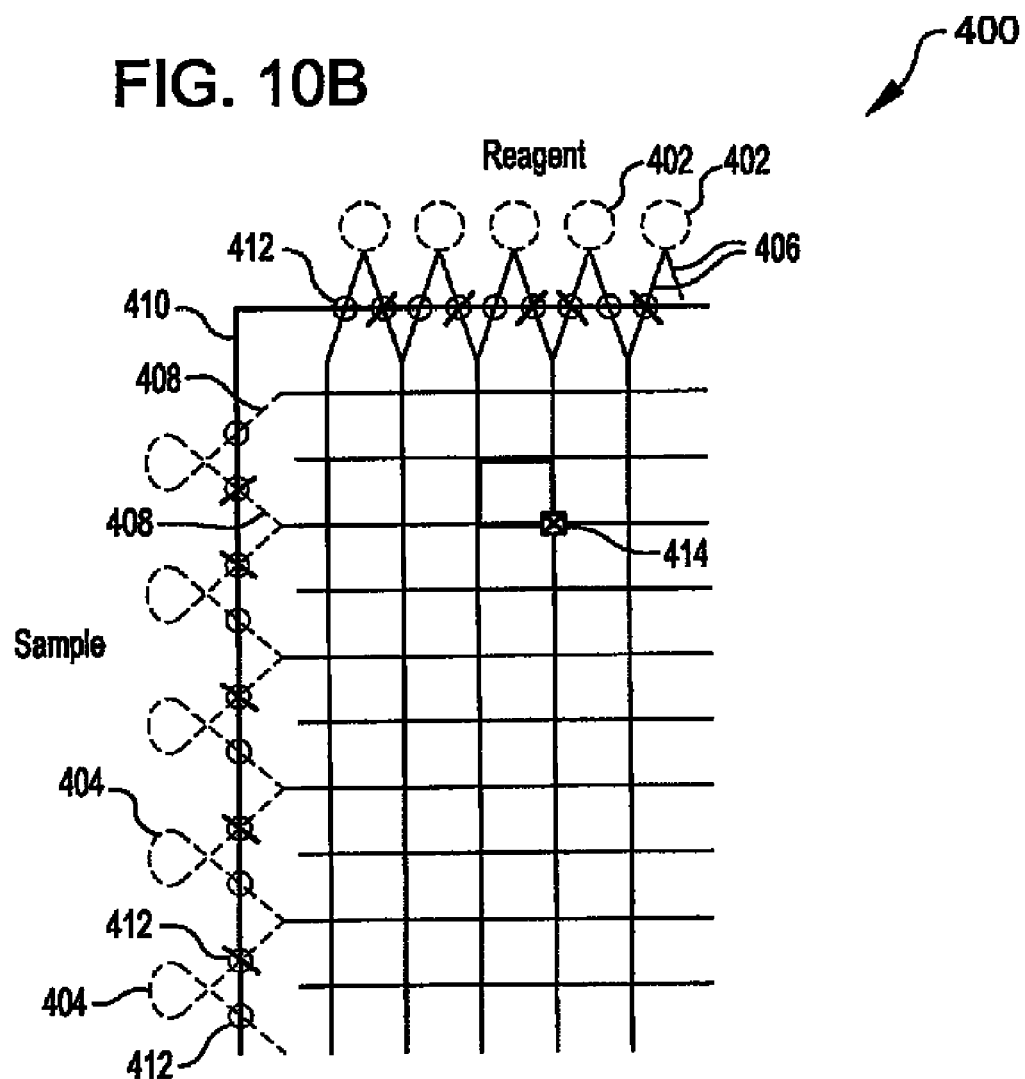

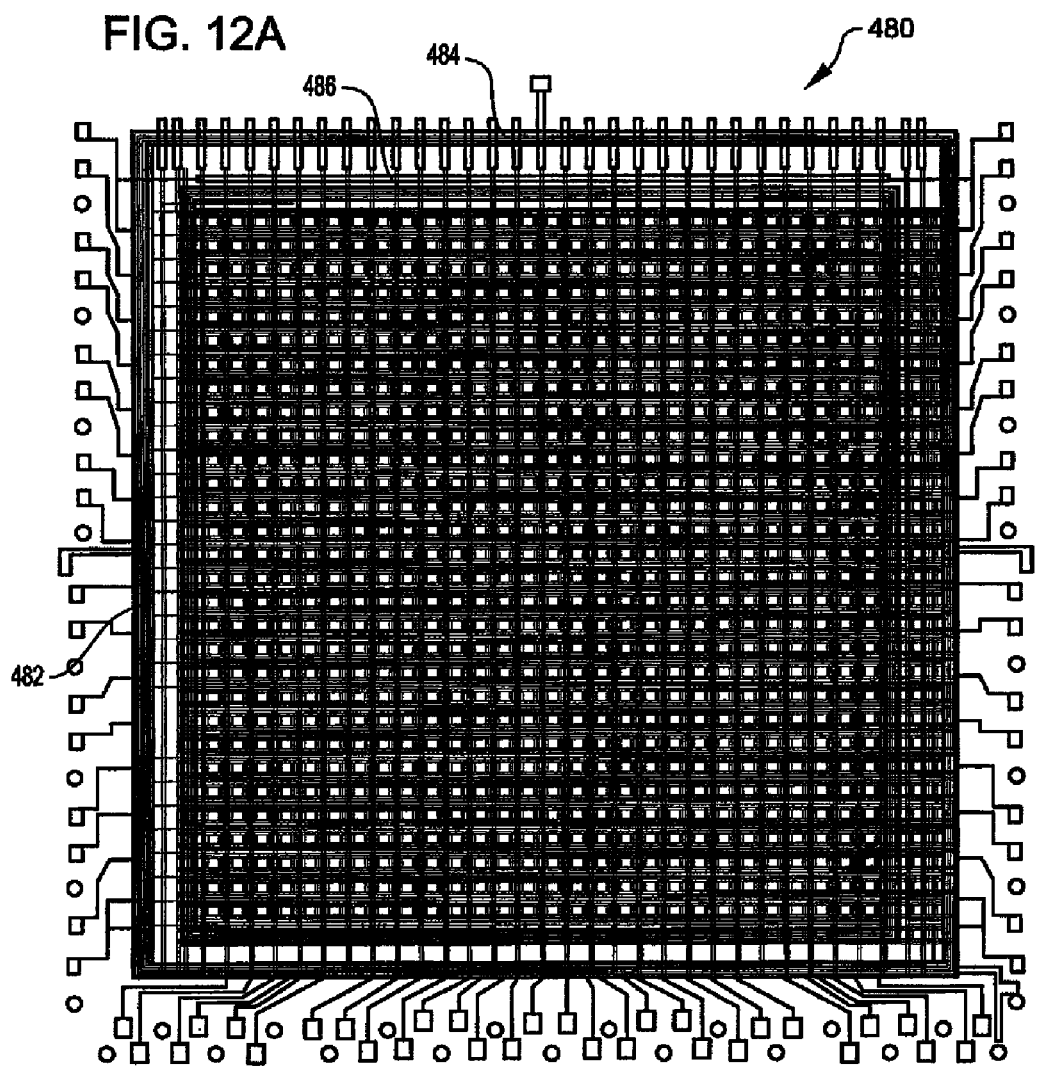

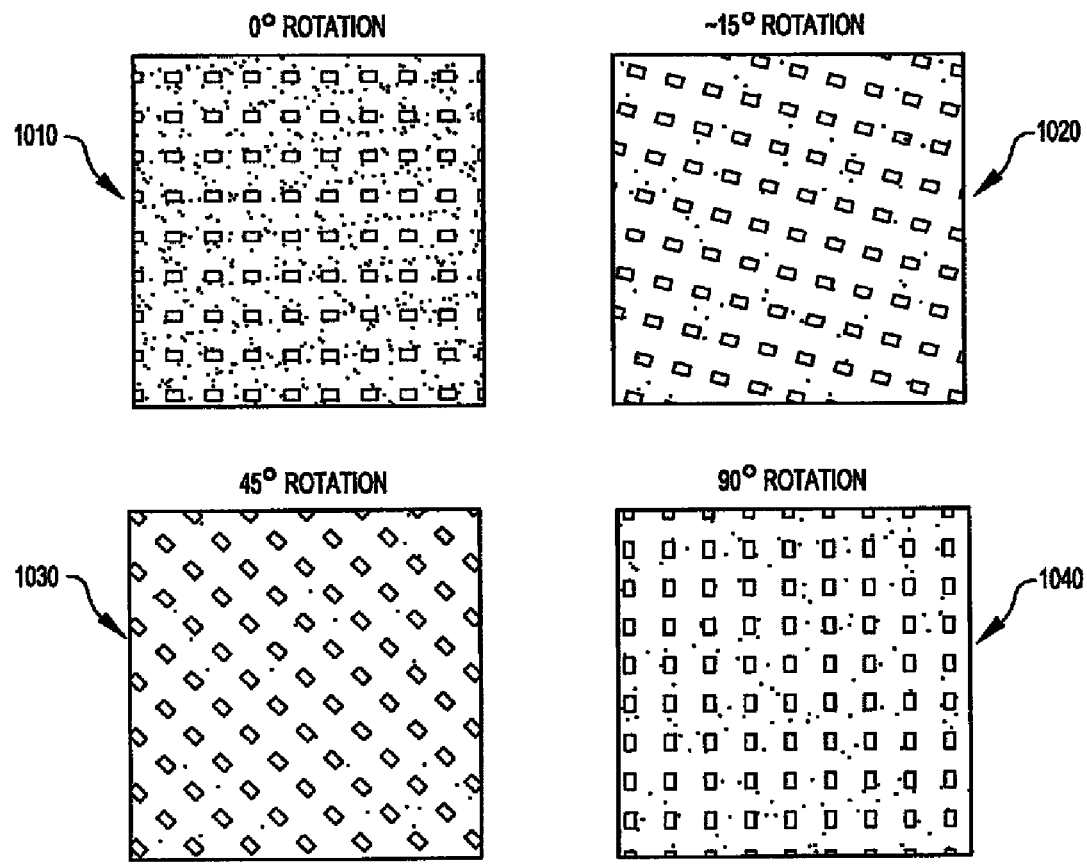

Reducing in-chip scattered light
Test result, Alexa 568 imaging:

MICROFLUIDIC DEVICES AND METHODS

CROSS-REFERENCES TO RELATED APPLICATIONS

This application is a continuation of U.S. patent application Ser. No. 12/688,462, filed Jan. 15, 2010, which claims the benefit of U.S. Provisional Application No. 61/145,459, filed Jan. 16, 2009; the entire contents of these applications are incorporated herein by reference.

BACKGROUND OF THE INVENTION

The present invention relates generally to microfluidic devices, which provide for precise control and manipulation of fluids that are geometrically constrained to a small, typically sub-millimeter, scale. In particular, the invention provides microfluidic devices and related apparatus, systems, and methods.

Recently, there have been concerted efforts to develop and manufacture microfluidic systems to perform various chemical and biochemical analyses and syntheses, both for preparative and analytical applications. The goal to make such devices arises because of the significant benefits that can realized from miniaturization with respect to analyses and syntheses conducted on a macro scale. Such benefits include a substantial reduction in time, cost and the space requirements for the devices utilized to conduct the analysis or synthesis. Additionally, microfluidic devices have the potential to be adapted for use with automated systems, thereby providing the additional benefits of further cost reductions and decreased operator errors because of the reduction in human involvement. Microfluidic devices have been proposed for use in a variety of applications, including, for instance, capillary electrophoresis, gas chromatography and cell separations.

Microfluidic devices adapted to conduct nucleic acid amplification processes are potentially useful in a wide variety of applications. For example, such devices could be used to determine the presence or absence of a particular target nucleic acid in a sample, as an analytical tool. Examples of utilizing microfluidic device as an analytical tool include:

testing for the presence of particular pathogens (e.g., viruses, bacteria or fungi);

identification processes (e.g., paternity and forensic applications);

detecting and characterizing specific nucleic acids associated with particular diseases or genetic disorders (e.g., fetal diagnostics);

detecting gene expression profiles/sequences associated with particular drug behavior (e.g., for pharmacogenetics, i.e., choosing drugs which are compatible/especially efficacious for/not hazardous with specific genetic profiles); and conducting genotyping analyses and gene expression analyses (e.g., differential gene expression studies).

Alternatively, the devices can be used in a preparative fashion to amplify nucleic acids, producing an amplified product at sufficient levels needed for further analysis. Examples of these analysis processes include sequencing of the amplified product, cell-typing, DNA fingerprinting, and the like. Amplified products can also be used in various genetic engineering applications. These genetic engineering applications include (but are not limited to) the production of a desired protein product, accomplished by insertion of the amplified product into a vector that is then used to transform cells into the desired protein product.

While currently available microfluidic devices and related apparatus, systems, and methods provide for a wide range of uses, further improvements are desirable. In particular, it would be beneficial to reduce costs associated with the production and use of microfluidic devices. It would also be beneficial to provide improved processes for using microfluidic devices.

BRIEF SUMMARY OF THE INVENTION

Embodiments of the present invention provide improved microfluidic devices and related apparatuses, systems, and methods. Methods are provided for reducing mixing times during use of microfluidic devices. Microfluidic devices and related methods of manufacturing are provided with increased manufacturing yield rates. Improved apparatuses and related systems are provided for supplying controlled pressure to microfluidic devices. Methods and related microfluidic devices are provided for reducing dehydration of microfluidic devices during use. Microfluidic devices and related methods are provided with improved sample to reagent mixture ratio control. Microfluidic devices and systems are provided with improved resistance to compression fixture pressure induced failures. Methods and systems for conducting temperature controlled reactions using microfluidic devices are provided that reduce condensation levels within the microfluidic device. Methods and systems are provided for improved fluorescent imaging of microfluidic devices. Reduced mixing times lowers both time and related costs for the analysis being conducted. Microfluidic devices with increased manufacturing yield rates lower costs and help to minimize waste. Improved apparatus and systems for supplying controlled pressure to microfluidic devices help to simplify microfluidic device processing equipment, thereby reducing costs. Decreased microfluidic device dehydration helps to minimize detrimental impacts that occur when water escapes from reaction fluids, especially from sample fluids that contain significant relative amounts of water. Improved sample to reagent mixture ratio control helps to increase processing effectiveness. Lower rates of compression fixture pressure induced failure help to increase the success rate achieved during temperature controlled reactions. Improved fluorescent imaging helps to increase the certainty by which analysis results can be determined.

Reduced Mixing Times

Thus, in one aspect, embodiments of the present invention provide methods for reducing mixing time for a mixture of a sample fluid and a reagent fluid. A method can, for example, involve a microfluidic device having a reaction cell that includes a sample chamber and a reagent chamber that are in fluid communication through an interface channel having an interface valve. Sample fluid can be introduced into the sample chamber at a first pressure and reagent fluid can be introduced into the reagent chamber at a second pressure. The sample fluid and the reagent fluid can be mixed by opening the interface valve. The first pressure and the second pressure can be sufficiently different to cause the mixing to occur at least in part by fluid injection. In some embodiments, the sample chamber pressure is greater than the reagent chamber pressure, and can be greater by 1.0 psi. In other embodiments, the reagent chamber pressure is greater than the sample chamber pressure, and can be greater by 1.0 psi. Often, a microfluidic device reaction cell will be configured with a sample chamber volume being greater than a reagent chamber volume, but can also be configured with a reagent chamber volume being equal to or greater than a sample chamber volume.

Increased Manufacturing Yield Rates

In another aspect, embodiments of the present invention provides microfluidic devices with increased manufacturing yield rates, and related methods for manufacturing. A device can include, for example, a configuration that allows for the isolation of defective reaction cells. During the manufacture of a microfluidic device, manufacturing defects may result in one or more defective reaction cells. Often, these defective cells can be identified during quality control inspections. Embodiments of the present invention provide microfluidic devices that can be configured so as to isolate one or more reaction cells, including one or more identified defective reaction cells. The device can include a first flow channel for introduction of a fluid via an inlet to the first reaction cell and a second flow channel for introduction of a fluid via the inlet to the second reaction cell. A microfluidic device can be configurable to have the inlet in fluid communication with the first flow channel, and fluidically separated from the second flow channel. Often, the device will also be configurable to have the inlet in fluid communication with the second flow channel and fluidically separated from the first flow channel. In some embodiments, each of the first flow channel and the second flow channel is initially in fluid communication with the inlet, and the device includes a first fusible isolation feature and a second fusible isolation feature, the first fusible isolation feature being configurable to fluidically separate the first flow channel from the inlet, and the second fusible isolation feature being configurable to fluidically separate the second flow channel from the inlet. In some embodiments, each of the first and second fusible isolation features is a containment valve that is fusible by an exposure of ultraviolet light. The first and second flow channels can be for the introduction of a sample fluid. Alternatively, the first and second flow channels can be for the introduction of a reagent fluid.

In further embodiments, a microfluidic device with increased manufacturing yield rate can include both a sample inlet and associated first and second sample flow channels, and a reagent inlet and associated first and second reagent flow channels. The first sample flow channel can be for introducing a sample fluid via the sample inlet into a first reaction cell, and the second sample flow channel can be for introducing a sample fluid via the sample inlet into a second reaction cell. Likewise, the first reagent flow channel can be for introducing a reagent fluid into the first reaction cell via the reagent inlet, and the second reagent flow channel can be for introducing a reagent fluid into the second reaction cell via the reagent inlet. The device can be configurable to have the sample inlet in fluid communication with the first sample flow channel and fluidically separated from the second sample flow channel. Likewise, the device can be configurable to have the reagent inlet in fluid communication with the first reagent flow channel and fluidically separated from the second reagent flow channel. Often, a device will also be configurable to have the sample inlet in fluid communication with the second sample flow channel and fluidically separated from the first sample flow channel. Likewise, a device will often be configurable to have the reagent inlet in fluid communication with the second reagent flow channel and fluidically separated from the first reagent flow channel. In some embodiments, each inlet can be in initial fluid communication with two reaction cells by way of separate flow channels, and the device can include fusible isolation features configured to fluidically separate an inlet from a reaction cell. In some embodiments, a fusible isolation feature includes a containment valve that is fusible by an exposure of ultraviolet light or other electromagnetic radiation.

In further embodiments, an increased manufacturing yield rate microfluidic device for reacting M number of samples with N number of different reagents can include a plurality of sample inlets, a plurality of sample flow channels, a plurality of reagent inlets, and a plurality of reagent flow channels. A device can be configurable to selectively cause each of the plurality of sample inlets to be in fluid communication with a first of a unique pair of the plurality of sample flow channels and fluidically separated from a second of the unique pair of the plurality of sample flow channels. Likewise, a device can be configurable to selectively cause each of the plurality of reagent inlets to be in fluid communication with a first of a unique pair of the plurality of reagent flow channels and fluidically separate from a second of the unique pair of the plurality of reagent flow channels. Often, a device can be configurable to selectively cause each of the plurality of sample inlets to be in fluid communication with a second of a unique pair of the plurality of sample flow channels and fluidically separated from a first of the unique pair of the plurality of sample flow channels. Likewise, a device can often be configurable to selectively cause each of the plurality of reagent inlets to be in fluid communication with a second of a unique pair of the plurality of reagent flow channels and fluidically separate from a first of the unique pair of the plurality of reagent flow channels. In some embodiments, each of the plurality of sample inlets is in initial fluid communication with a unique pair of the plurality of sample flow channels, and the device further comprises a plurality of fusible sample isolation features, each fusible sample isolation feature being configurable to fluidically separate one of the plurality of sample inlets from one of the plurality of sample flow channels. In some embodiments, each of the plurality of reagent inlets is in initial fluid communication with a unique pair of the plurality of reagent flow channels, and the device further comprises a plurality of fusible reagent isolation features, each fusible reagent isolation feature being configurable to fluidically separate one of the plurality of reagent inlets from one of the plurality of reagent flow channels. In some embodiments, a fusible isolation feature includes a containment valve that is fusible by an exposure to ultraviolet light or other electromagnetic radiation.

Related methods for manufacturing a microfluidic device having increased manufacturing yield rate can include the identification of defective reaction cells and configuring the device to isolate the identified defective reaction cells. In some embodiments, a method for manufacturing a microfluidic device can include: fabricating a microfluidic device according to any of the above described embodiments; performing an inspection for defects in the microfluidic device; and configuring the device so to isolate defects.

Supplying Controlled Pressure

In another aspect, embodiments of the present invention provide apparatus and systems for supplying controlled pressure to a microfluidic device. An apparatus can include, for example, a holder configured to couple with a microfluidic device, a plurality of accumulators for supplying controlled pressure to the microfluidic device, and a pressure regulator for selectively regulating pressure supplied to each of the plurality of accumulators. In some embodiments, the pressure regulator includes an accumulator selector valve. In some embodiments, the pressure regulator employs rotary motion. In some embodiments, an apparatus for supplying controlled pressure includes one or more first supply outlet selector valves for selectively placing a first supply outlet in fluid communication with one of the plurality of accumulators. In some embodiments, an apparatus for supplying controlled pressure includes one or more second supply outlet selector valves for selectively placing a second supply outlet in fluid communication with one of the plurality of accumulators. In some embodiments, a first supply outlet selector valve includes a rotary valve. In some embodiments, a second supply outlet selector valve includes a rotary valve. A system can include, for example, any of the above described apparatus and a control unit for controlling the operation of the pressure regulator. In some embodiments, the system can control one or more accumulator selector valves, and one or more supply outlet selector valves.

Reduced Dehydration

In another aspect, embodiments of the present invention provide methods for reducing dehydration of a microfluidic device, and related microfluidic devices. A method can include, for example, providing a microfluidic device having one or more vent channels, introducing a sample fluid and a reagent fluid into the device, and introducing a substantially non-permeable fluid into at least one of the vent channels after the introduction of the sample fluid and the reagent fluid so as to inhibit dehydration of the device. In some embodiments, a method can include connecting two or more vent channels. In some embodiments, the substantially non-permeable fluid is perfluoropolyether oil. In some embodiments, each vent channel is in fluid communication with a vent channel port for introduction of the substantially non-permeable fluid into the vent. In some embodiments, introduction of substantially non-permeable fluid forces air to emerge from a vent channel vent. A related microfluidic device can include, for example, a plurality of reaction cells, each reaction cell for reacting a sample fluid with a reagent; and a plurality of vent channels, each vent channel adapted to vent the device during the introduction of fluid into the device, and each vent line being in fluid communication with a vent channel port.

Improved Mixture Ratio Control

In another aspect, embodiments of the present invention provide microfluidic devices having improved sample to reagent mixture ratio control, and related methods. A microfluidic device can include, for example, a sample chamber for containing a sample fluid; a reagent chamber for containing a reagent fluid; a reaction chamber for receiving sample fluid from the sample chamber and reagent fluid from the reagent chamber; a sample channel for transferring sample fluid from the sample chamber to the reaction chamber; the sample channel including a sample channel restriction for controlling the flow rate of sample fluid, and a sample interface valve associated therewith for controlling fluid communication between the sample chamber and the reaction chamber; and a reagent channel for transferring reagent fluid from the reagent chamber to the reaction chamber; the reagent channel including a reagent channel restriction for controlling the flow rate of reagent fluid, and a reagent interface valve associated therewith for controlling fluid communication between the reagent chamber and the reaction chamber. In some embodiments, the device includes an interface control channel for controlling actuation of the sample interface valve and the reagent interface valve. In some embodiments, the device includes a sample interface control channel for controlling actuation of the sample interface valve and a reagent control channel for controlling actuation of the reagent interface valve. In some embodiments, the sample interface valve is disposed between the sample channel restriction and the reaction chamber. In some embodiments, the reagent interface valve is disposed between the reagent channel restriction and the reaction chamber. In some embodiments, the sample channel restriction and the reagent channel restriction are adapted so that the amount of sample fluid received by the reaction chamber exceeds the amount of reagent fluid received by the reaction chamber. In some cases, the ratio of sample fluid received to reagent fluid received is approximately ten to one.

In further embodiments, a microfluidic devices having improved sample to reagent mixture ratio control can include: a plurality of sample chambers, each of the sample chambers being adapted to contain a sample fluid; a plurality of reagent chambers, each of the reagent chambers being adapted to contain a reagent fluid; a plurality of reaction chambers, each of the reaction chambers being adapted to receive sample fluid from one of the sample chambers and to receive reagent fluid from one of the reagent chambers; a plurality of sample channels, each of the sample channels being adapted to transfer sample fluid from one of the sample chambers to one of the reaction chambers, at least one of the sample channels including a sample channel restriction for controlling the flow rate of sample fluid, and a sample interface valve associated therewith for controlling fluid communication between the sample chamber and the reaction chamber; and a plurality of reagent channels, each of the reagent channels being adapted to transfer reagent fluid from one of the reagent chambers to one of the reaction chambers, at least one of the reagent channels including a reagent channel restriction for controlling the flow rate of reagent fluid, and a reagent interface valve associated therewith for controlling fluid communication between the reagent chamber and the reaction chamber. In some embodiments, a sample channel restriction is configured differently than another sample channel restriction so as to compensate for variations in sample chamber pressure and/or sample channel flow impedance. In some embodiments, a reagent channel restriction is configured differently than another reagent channel restriction so as to compensate for variations in reagent chamber pressure and/or reagent channel flow impedance. In some embodiments, a microfluidic device can include a plurality of interface control channels, each of which is for controlling actuation of one of the sample interface valves and one of the reagent interface valves so as to control the flow of sample fluid and reagent fluid into one of the reaction chambers. In some embodiments, the microfluidic device can include a plurality of sample interface control channels each of which is for controlling actuation of a sample interface valve, and can include a plurality of reagent interface control channels each of which is for controlling actuation of a reagent interface valve. In some embodiments, one or all of the sample interface valves or reagent interface valves can be disposed between a channel restriction and one of the reaction chambers. In some embodiments, the channel restrictions are adapted so that the amount of sample fluid received by a reaction chamber exceeds the amount of reagent received. In some embodiments, the ratio of sample received to reagent received by a reaction chamber is approximately ten to one.

Related methods for conducting a reaction between a sample and a reagent with improved sample to reagent mixture ratio control can include, for example, providing a microfluidic device in accordance with any of the above described embodiments having channel restrictions; introducing a sample fluid into a sample chamber with the sample chamber interface valve closed; introducing a reagent fluid into a reagent chamber with the reagent interface valve closed; opening the sample interface valve to transfer sample fluid to the reaction camber; opening the reagent interface valve to transfer reagent fluid to the reaction chamber; closing the sample interface valve after the transfer of the sample fluid to the reaction chamber; and closing the reagent interface valve after the transfer of reagent fluid to the reaction chamber. In some embodiments, a sample interface valve and a reagent interface valve are opened or closed at substantially the same time.

Increased Resistance to Compression Fixture Induced Failure

In another aspect, embodiments of the present invention encompasses microfluidic devices and related systems providing increased resistance to compression fixture pressure induced failure. A microfluidic device can include, for example, a plurality of inlets formed in an elastomeric substrate; a plurality of chambers formed in the elastomeric substrate, each one of the chambers being in fluid communication with one of said plurality of inlets through one of a plurality of flow channels, each flow channel having a control valve for controlling fluid communication between said one of the plurality of inlets and said one of the plurality of chambers; and a control channel formed in the elastomeric substrate, the control channel having a first end and a second end, the first end being in fluid communication with the second end through a restriction feature for preventing the flow of control fluid from the second end to the first end, the second end being coupled with at least one of said control valves for actuation of said at least one control valve. In some embodiments, the restriction feature is a check valve. In some embodiments, the restriction feature is sealed by an application of ultraviolet light. In some embodiments, the restriction feature is sealed thermally. In some embodiments, the restriction feature is an actuated element, which can be a guided pin or cam. In some embodiments, a microfluidic device can include a compensation feature adapted to increase fluid pressure in a control channel in response to the microfluidic device being compressed. The compensation feature can be in fluid communication with a control channel, and can be a fluid filled structure.

In some embodiments, a microfluidic system having increased resistance to compression fixture pressure induced failure can include, for example, a microfluidic device having a control channel coupled with at least one control valve, and a control fluid introduction device in fluid communication with the control channel. In some embodiments, the control fluid introduction device can be adapted to prevent backflow of control fluid from the microfluidic device. In some embodiments, the control fluid introduction device includes an accumulator and is adapted to eliminate the presence of gas within the accumulator. In some embodiments, the control fluid introduction device includes a backflow restriction feature, which can be a check valve, or can include an actuated element such as a guided pin or cam.

In some embodiments, a microfluidic system having increased resistance to compression fixture pressure induced failure can include, for example, a preferential compression fixture for applying pressure preferentially to areas of the microfluidic device where control-fluid-filled structures exist so as to produce increase control fluid pressure in a control channel in response to the microfluidic device being compressed. In some embodiments, the preferential compression fixture can include a pad or a pin for applying pressure preferentially.

In some embodiments, a microfluidic system having increased resistance to compression fixture pressure induced failure can include, for example, a compensation device in fluid communication with a control channel. The compensation device can produce increased control fluid pressure in the control channel in response to the microfluidic device being compressed by the compression fixture. In some embodiments, the compensation device includes a syringe plunger.

Temperature Controlled Reactions with Reduced Condensation

In another aspect, embodiments of the present invention provide methods and systems for conducting a microfluidic temperature controlled reaction using a thermal control device so as to reduce condensation levels within a microfluidic device. A method can include, for example, placing a microfluidic device in thermal communication with a thermal control source using a compression fixture and heating the compression fixture so that a temperature of an elastomeric surface of the microfluidic device contacted by the compression fixture is elevated above a condensation threshold. In some embodiments, the compression fixture is heated using a heat source other than the thermal control source. In some embodiments, the temperature of an elastomeric surface of the microfluidic device is elevated above forty degrees centigrade, and can be elevated above seventy degrees centigrade. Another method can include, for example, using a compression fixture that includes a permeable portion adapted to be held in contact with an elastomeric portion of the microfluidic device. In some embodiments, the thermal control device includes venting adapted to remove moisture from an elastomeric portion of a microfluidic device. In some embodiments, the venting is forced. In some embodiments, the thermal control device includes a dehydration device for removing moisture from an elastomeric portion of a microfluidic device.

In some embodiments, a system for conducting a microfluidic temperature controlled reaction can include, for example, a thermal control device that includes a thermal control source and a compression fixture for holding a microfluidic device in thermal communication with the thermal control source. The thermal control device can be adapted to heat the compression fixture so that a temperature of an elastomeric surface of the microfluidic device contacted by the compression fixture is elevated above a condensation threshold. The thermal control device can include a heat source separate from the thermal control source, and the separate heat source can supply heat to an upper region of an elastomeric portion of a microfluidic device. In some embodiments, the compression fixture includes a permeable portion adapted to be held in contact with an elastomeric portion of a microfluidic device. The thermal control device can include venting adapted to remove moisture from an elastomeric portion of a microfluidic device, and the venting can be forced. In some embodiments, the thermal control device includes a dehydration device for removing moisture from an elastomeric portion of the microfluidic device.

Improved Fluorescent Imaging

In another aspect, the present invention provides methods and systems for fluorescent imaging of a microfluidic device. A method can include, for example, providing a microfluidic device having a non-opaque portion that includes a plurality of processing sites, a first plurality of flow channels primarily oriented along a first feature direction, and a second plurality of flow channels primarily oriented along a second feature direction. A method can include illuminating the microfluidic device from an illumination direction having a non-orthogonal azimuth relative to both the first feature direction and the second feature direction, and imaging the microfluidic device from an imaging direction. In some embodiments, the azimuth can be non-orthogonal by at least 15 degrees, by at least 30 degrees, or by approximately 45 degrees. A method can include determining an elevation for the illumination direction so as to substantially minimize a ratio of reflections to fluorescent signal in the imaging direction. A method can include illuminating the microfluidic device from an illumination direction so as to substantially minimize a ratio of reflections to fluorescent signal in the imaging direction, and can include determining the illumination direction. Determining the illumination direction can include determining a ratio of reflections to fluorescent signal for a plurality of different azimuths and/or a plurality of different elevations.

In some embodiments, a system for fluorescent imagining of a microfluidic device can include, for example, a microfluidic device, an illumination subsystem adapted to illuminate the microfluidic device with electromagnetic radiation, and an imaging subsystem adapted to image the microfluidic device from an imaging direction. The microfluidic device can have a non-opaque portion that includes a plurality of processing sites, a first plurality of flow channels primarily oriented along a first feature direction, and a second plurality of flow channels primarily oriented along a second feature direction. The illumination subsystem can illuminate the microfluidic device from an illumination direction non-orthogonal to both the first feature direction and the second feature direction. The imaging subsystem can include a charge-coupled device (CCD) camera array and/or a complementary metal-oxide-semiconductor (CMOS) device. The illumination direction can be adjustable, such as in azimuth and/or elevation. The illumination subsystem can be adapted to illuminate the microfluidic device from an azimuth that is non-orthogonal relative to both the first feature direction and the second feature direction by at least 15 degrees, by at least 30 degrees, or by approximately 45 degrees. The illumination subsystem can be adapted to illuminate the microfluidic device so as to substantially minimize a ratio of reflections to fluorescent signal in the imaging direction.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 10A is a simplified schematic diagram illustrating a microfluidic device matrix having alternate fluid introduction flow paths configurable to isolate device defects according to embodiments of the present invention.

FIG. 10B is a simplified schematic diagram illustrating a microfluidic device matrix having alternate fluid introduction flow paths configurable to isolate device defects according to embodiments of the present invention.

FIG. 12A shows a microfluidic matrix device having peripheral vent channels according to embodiments of the present invention.

FIG. 23A shows reflection test results using illumination in accordance with embodiments of the present invention.

DETAILED DESCRIPTION OF THE INVENTION

Figure 1:
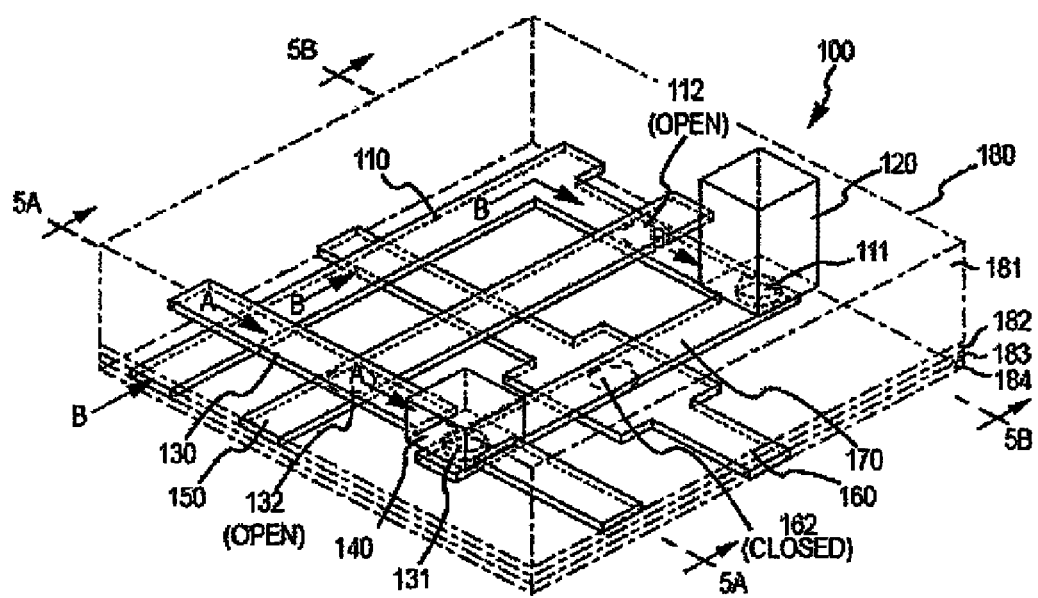
FIG. 1 depicts a perspective view of a unit cell of a microfluidic device according to embodiments of the present invention, showing flow paths for fluid introduction.

The present invention relates generally to microfluidic devices and related apparatus, systems, and methods. In particular, methods are provided for reducing mixing times during use of microfluidic devices. Microfluidic devices and related methods of manufacturing are provided with increased manufacturing yield rates. Improved apparatus and related systems are provided for supplying controlled pressure to microfluidic devices. Methods and related microfluidic devices are provided for reducing dehydration of microfluidic devices during use. Microfluidic devices and related methods are provided with improved sample to reagent mixture ratio control. Microfluidic devices and systems are provided with improved resistance to compression fixture pressure induced failure. Methods and systems for conducting temperature controlled reactions using microfluidic devices are provided that reduce condensation levels within the microfluidic device. Methods and systems are provided for improved fluorescent imaging of microfluidic devices.

Microfluidic Device Discussion

In the present application, references are made to certain types of "reaction" chambers in a microfluidic device. In general, these "reaction chambers" include processing sites, processing chambers, and/or reaction sites, any combination of these, and the like. These chambers may be closed, partially closed, open, partially open, sealed, or combinations thereof, including any temporary or transient conditions involving any of these states, and the like. In some embodiments, the chambers are sealed, capable of being sealed, closeable, isolated, capable of being isolated, and combinations thereof, and any combination or single condition of any temporary or transient conditions involving any of these states, and the like. Therefore, use of the term reaction chamber is not intended to limit the present invention, but to include these other structures. Additionally, the term "chamber" is not intended to limit the present invention, but should be used in its ordinary meaning, unless specific features associated with the chamber have been recited. Of course, there can be other variations, modifications, and alternatives.

Moreover, through the present document, references are made to fluorescent indications from a microfluidic device. Embodiments herein are not limited to such fluorescent indications, but also include luminescent indications, including chemiluminescent, electroluminescent, electrochemiluminescent, and phospholuminescent, bioluminescent, and other luminescent processes, or any other processing involving any other type of indications that may be detected using a detection device. As will be evident to one of skill in the art, methods and systems operable in the detection and analysis of these fluorescent and luminescent indications are transferable from one indication to another. Additionally, although some embodiments utilize spectral filters as optical elements, this is not required. Some fluorescent and luminescent applications do not utilize spectral filters in the optical excitation path, the optical emission path, or both. As described herein, other embodiments utilize spectral filters. One of skill in the art will appreciate the differences associated with particular applications.

In some embodiments, a variety of devices and methods for conducting microfluidic analyses are utilized herein, including devices that can be utilized to conduct thermal cycling reactions such as nucleic acid amplification reactions. The devices can differ from conventional microfluidic devices in that they can include elastomeric components such as deflectable membranes that can form valves; in some instances, much or all of the device is composed of elastomeric material. For example, amplification reactions can be linear amplifications, (amplifications with a single primer), as well as exponential amplifications (i.e., amplifications conducted with a forward and reverse primer set).

The methods and systems provided by some embodiments utilize blind channel type devices in performing nucleic acid amplification reactions. In these devices, the reagents that are typically deposited within the reaction sites are those reagents necessary to perform the desired type of amplification reaction. Usually this means that some or all of the following are deposited: primers, polymerase, nucleotides, metal ions, buffer, and cofactors, for example. The sample introduced into the reaction site in such cases is the nucleic acid template. Alternatively, however, the template can be deposited and the amplification reagents flowed into the reaction sites. As discussed in more detail throughout the present specification, when a matrix device is utilized to conduct an amplification reaction, samples containing nucleic acid template are flowed through the vertical flow channels and the amplification reagents through the horizontal flow channels or vice versa.

A variety of matrix or array-based devices are also utilized in some embodiments. Certain of these devices include: (i) a first plurality of flow channels formed in an elastomeric substrate, (ii) a second plurality of flow channels formed in the elastomeric substrate that intersect the first plurality of flow channels to define an array of reaction sites, (iii) a plurality of isolation valves disposed within the first and second plurality of flow channels that can be actuated to isolate solution within each of the reaction sites from solution at other reaction sites, and (iv) a plurality of perimeter guard channels surrounding one or more of the flow channels and/or one or more of the reaction sites to inhibit evaporation of solution therefrom. The foregoing devices can be utilized to conduct a number of different types of reactions, including those involving temperature regulation (e.g., thermocycling of nucleic acid analyses).

Some of the microfluidic devices utilize a design typically referred to herein as "blind channel" or "blind fill" and are characterized in part by having a plurality of blind channels, which are flow channels having a dead end or isolated end such that solution can only enter and exit the blind channel at one end (i.e., there is not a separate inlet and outlet for the blind channel). These devices require only a single valve for each blind channel to isolate a region of the blind channel to form an isolated reaction site. Additionally, the blind channels can be connected to an interconnected network of channels such that all the reaction sites can be filled from a single, or limited number, of sample inputs. Because of the reduction in complexity in inputs and outputs and the use of only a single valve to isolate each reaction site, the space available for reaction sites is increased. Thus, the features of these devices means that each device can include a large number of reaction sites (e.g., up to tens of thousands) and can achieve high reaction site densities (e.g., over 1,000-4,000 reaction sites/cm$^2$). Individually and collectively, these features also directly translate into a significant reduction in the size of these devices compared to traditional microfluidic devices.

Some microfluidic devices utilize a matrix design. Microfluidic devices of this type can utilize a plurality of intersecting horizontal and vertical flow channels to define an array of reaction sites at the points of intersection. Discrete reaction chambers can also be fluidically coupled with the points of intersection. A valve system referred to as a switchable flow array can be used to control the flow through the flow channels. Matrix devices can be constructed to analyze a large number of samples under a limited number of conditions. Some microfluidic devices can be hybrids that include both matrix and blind channel features.

Other microfluidic devices are massively partitioning devices (DID) such as described in PCT publication WO 2004/089810, U.S. patent application number No. 10/819, 088 published as US 20050019792, copending commonly assigned patent application Ser. No. 06/2141 entitled "Analysis using microfluidic partitioning devices" filed Jun. 2, 2006, each of which is incorporated by reference in its entirety for all purposes. Using massively partitioning devices, a sample can be partitioned into a multitude of isolated reaction chambers, and reactions carried out simultaneously in each chamber.

The microfluidic devices that are described herein can be made from various materials. For example, various components such as flow channels, control channels, valves and/or pumps can be fabricated from elastomeric materials. In some instances, essentially the entire device can be made of elastomeric materials. However, while some embodiments are described that include components made from elastomeric materials, various other materials can also be used.

The design of the devices enables them to be utilized in combination with a number of different heating systems. Thus, the devices are useful in conducting diverse analyses that require temperature control. Additionally, those microfluidic devices adapted for use in heating applications can incorporate a further design feature to minimize evaporation of sample from the reaction sites. Devices of this type may include a number of guard channels and/or reservoirs or chambers formed within the device through which water can be flowed to increase the water vapor pressure within the material from which the device is formed, thereby reducing evaporation of sample material from the reaction sites.

In another embodiment, a temperature cycling device may be used to control the temperature of the microfluidic devices. Preferably, the microfluidic device would be adapted to make thermal contact with the temperature cycling device. Where the microfluidic device is supported by a substrate material, such as a glass slide or the bottom of a carrier plate, such as a plastic carrier, a window may be formed in a region of the carrier or slide such that the microfluidic device, preferably a device having an elastomeric block, may directly contact the heating/cooling block of the temperature cycling device. In a preferred embodiment, the heating/cooling block has grooves therein in communication with a vacuum source for applying a suction force to the microfluidic device, preferably a portion adjacent to where the reactions are taking place. Alternatively, a rigid thermally conductive plate may be bonded to the microfluidic device that then mates with the heating and cooling block for efficient thermal conduction.

The array format of certain of the devices means the devices can achieve high throughput. Collectively, the high throughput and temperature control capabilities make the devices useful for performing large numbers of nucleic acid amplifications (e.g., polymerase chain reaction (PCR)). Such reactions will be discussed at length herein as illustrative of the utility of the devices, especially of their use in any reaction requiring temperature control. However, it should be understood that the devices are not limited to these particular applications. The devices can be utilized in a wide variety of other types of analyses or reactions. Examples include analyses of protein-ligand interactions and interactions between cells and various compounds. Further examples are provided throughout the present specification.

The microfluidic devices disclosed herein are typically constructed at least in part from elastomeric materials and constructed by single and multilayer soft lithography (MSL) techniques and/or sacrificial-layer encapsulation methods (see, e.g., Unger et al. (2000) Science 288:113-116, and PCT Publication WO 01/010 25, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al. (2000) Science 288:113-116, and PCT Publication WO/02/43615 and WO 01/01025.

The devices provided herein incorporate such pumps and/or valves to isolate selectively a reaction site at which reagents are allowed to react. Alternatively, devices without pumps and/or valves are utilized that use pressure driven flow or polymerization processes to close appropriate channels and thereby selectively isolate reaction sites. The reaction sites can be located at any of a number of different locations within the device. For example, in some matrix-type devices, the reaction site is located at the intersection of a set of flow channels. In blind channel devices, the reaction site is located at the end of the blind channel.

If the device is to be utilized in temperature control reactions (e.g., thermocycling reactions), then, as described in greater detail infra, the elastomeric device can be fixed to a support (e.g., silicon wafer, plastic carrier, etc.). The resulting structure can then be placed on a temperature control plate, for example, to control the temperature at the various reaction sites. In the case of thermocycling reactions, the device can be placed on any of a number of thermocycling plates.

Because the devices can be made of materials that are relatively optically transparent (e.g., elastomeric materials), reactions can be readily monitored using a variety of different detection systems at essentially any location on the microfluidic device. Most typically, however, detection occurs at the reaction site itself (e.g., an isolated chamber along a blind flow filled device). The fact that the device can be manufactured from substantially transparent materials also means that certain detection systems can be utilized with the current devices that are not usable with some traditional silicon-based microfluidic devices. Detection can be achieved using detectors that are incorporated into the device or that are separate from the device but aligned with the region of the device to be detected.

Devices utilizing the matrix design can have a plurality of vertical and horizontal flow channels that intersect to form an array of junctions. Because a different sample and reagent (or set of reagents) can be introduced into each of the flow channels, a large number of samples can be tested against a relatively large number of reaction conditions in a high throughput format. Thus, for example, if a different sample is introduced into each of M different vertical flow channels and a different reagent (or set of reagents) is introduced into each of N horizontal flow channels, then M×N different reactions can be conducted at the same time. Matrix devices can include valves that allow for switchable isolation of the vertical and horizontal flow channels. The valves can be positioned to allow selective flow just through the vertical flow channels or just through the horizontal flow channels. Because devices of this type allow flexibility with respect to the selection of the type and number of samples, as well as the number and type of reagents, these devices can be used for conducting analyses in which one wants to screen a large number of samples against a relatively large number of reaction conditions. The matrix devices can optionally incorporate guard channels to help inhibit evaporation of sample and reactants.

Some high-density matrix designs utilize fluid communication vias between layers of the microfluidic device to weave control lines and fluid lines through the device. For example, by having a fluid line in each layer of a two layer elastomeric block, higher density reaction cell arrangements are possible. As will be evident to one of skill in the art, multi-layer devices allow fluid lines to cross over or under each other without being in fluid communication. For example, in a particular design, a reagent fluid channel in a first layer is connected to a reagent fluid channel in a second layer through a via, while the second layer also has sample channels therein, the sample channels and the reagent channels terminating in sample and reagent chambers, respectively. The sample and reagent chambers are in fluid communication with each other through an interface channel that has an interface valve associated therewith to control fluid communication between each of the chambers of a reaction cell. In use, the interface is first closed, then reagent is introduced into the reagent channel from the reagent inlet and sample is introduced into the sample channel through the sample inlet. Containment valves are then closed to isolate each reaction cell from other reaction cells. Once the reaction cells are isolated, the interface valve is opened to cause the sample chamber and the reagent chamber to be in fluid communication with each other so that a desired reaction may take place. One of ordinary skill in the art would recognize many variations, modifications, and alternatives.

Accordingly, a particular design for a microfluidic device provides for a microfluidic device adapted to react M number of different samples with N number of different reagents comprising: a plurality of reaction cells, each reaction cell comprising a sample chamber and a reagent chamber, the sample chamber and the reagent chamber being in fluid communication through an interface channel having an interface valve associated therewith for controlling fluid communication between the sample chamber and the reagent chamber; a plurality of sample inlets each in fluid communication with the sample chambers; a plurality of reagent inlets each in fluid communication with the reagent chambers; wherein one of the sample inlets or reagent inlets is in fluid communication with one of the sample chambers or one of the reagent chambers, respectively, through a via. Certain embodiments include having the reaction cells be formed within an elastomeric block formed from a plurality of layers bonded together and the interface valve is a deflectable membrane; having the sample inlets be in communication with the sample chamber through a sample channel and the reagent inlet in fluid communication with the reagent chamber through a reagent channel, a portion of the sample channel and a portion of the reagent channel being oriented about parallel to each other and each having a containment valve associated therewith for controlling fluid communication therethrough; having the valve associated with the sample channel and the valve associated with the reagent channel in operable communication with each other through a common containment control channel; having the containment common control channel located along a line about normal to one of the sample channel or the reagent channel.

The microfluidic devices utilized in embodiments of the present invention may be further integrated into the carrier devices described in co-pending and commonly owned U.S. patent application Ser. No. 11/058,106, filed on Feb. 14, 2005, which is incorporated herein for all purposes. The carrier devices provide on-board continuous fluid pressure to maintain valve closure away from a source of fluid pressure, e.g., house air pressure. Patent application Ser. No. 11/058,106 further provides for an automated system for charging and actuating the valves of the present invention as described therein. An another preferred embodiment, the automated system for charging accumulators and actuating valves employs a device having a platen that mates against one or more surfaces of the microfluidic device, wherein the platen has at least two or more ports in fluid communication with a controlled vacuum or pressure source, and may include mechanical portions for manipulating portions of the microfluidic device, for example, but not limited to, check valves.

Another device utilized in embodiments of the present invention provides a carrier used as a substrate for stabilizing an elastomeric block. Preferably the carrier has one or more of the following features; a well or reservoir in fluid communication with the elastomeric block through at least one channel formed in or with the carrier; an accumulator in fluid communication with the elastomeric block through at least one channel formed in or with the carrier; and, a fluid port in fluid communication with the elastomeric block, wherein the fluid port is preferably accessible to an automated source of vacuum or pressure, such as the automated system described above, wherein the automated source further comprises a platen having a port that mates with the fluid port to form an isolated fluid connection between the automated system for applying fluid pressure or vacuum to the elastomeric block. In devices utilized in certain embodiments, the automated source can also make fluid communication with one or more accumulators associated with the carrier for charging and discharging pressure maintained in an accumulator. In certain embodiments, the carrier may further comprise a region located in an area of the carrier that contacts the microfluidic device, wherein the region is made from a material different from another portion of the carrier, the material of the region being selected for improved thermal conduction and distribution properties that are different from the other portion of the carrier. Preferred materials for improved thermal conduction and distribution include, but are not limited to silicon, preferably silicon that is highly polished, such as the type of silicon available in the semiconductor field as a polished wafer or a portion cut from the wafer, e.g., chip.

As described more fully below, embodiments of the present invention utilize a thermal source, for example, but not limited to a PCR thermocycler, which may have been modified from its original manufactured state. Generally the thermal source has a thermally regulated portion that can mate with a portion of the carrier, preferably the thermal conduction and distribution portion of the carrier, for providing thermal control to the elastomeric block through the thermal conduction and distribution portion of the carrier. In a preferred embodiment, thermal contact is improved by applying a source of vacuum to a one or more channels formed within the thermally regulated portion of the thermal source, wherein the channels are formed to contact a surface of the thermal conduction and distribution portion of the carrier to apply suction to and maintain the position of the thermal conduction and distribution portion of the carrier. In a preferred embodiment, the thermal conduction and distribution portion of the carrier is not in physical contact with the remainder of the carrier, but is associated with the remainder of the carrier and the elastomeric block by affixing the thermal conduction and distribution portion to the elastomeric block only and leaving a gap surrounding the edges of the thermal conduction and distribution portion to reduce parasitic thermal effects caused by the carrier. It should be understood that in many aspects of the invention described herein, the preferred elastomeric block could be replaced with any of the known microfluidic devices in the art not described herein, for example devices produced such as the GeneChip (R) by Affymetrix(R) of Santa Clara, Calif., USA, or by Caliper of Mountain View, Calif., USA. U.S. patents issued to Soane, Parce, Fodor, Wilding, Ekstrom, Quake, or Unger, describe microfluidic or mesoscale fluidic devices that can be substituted for the elastomeric block of the present invention to take advantage of the thermal advantages and improvements, e.g., suction positioning, reducing parasitic thermal transfer to other regions of the fluidic device, which are described above in the context of using an elastomeric block.

Utilizing systems and methods provided according to embodiments of the present invention, throughput increases are provided over 384 well systems. As an example, throughput increases of a factor of 4, 6, 12, and 24 and greater are provided in some embodiments. These throughput increases are provided while reducing the logistical friction of operations. Moreover the systems and methods of embodiments of the present invention enable multiple assays for multiple samples. For example, in a specific embodiment 96 samples and 96 assays are utilized to provide a total of 9,216 data points. In a particular example, the 96 assays are components of a TaqMan 5' Nuclease Assay.

Furthermore, embodiments of the present invention provide reduced reaction volumes. In embodiments of the present invention, reaction volumes ranging from 10 picoliters to 100 nanoliters are utilized. In some embodiments, reaction volumes greater than 100 nanoliters can be utilized. Merely by way of example, in embodiments, the methods and systems of the present invention can be utilized with reaction volumes of 10 picoliters to 1 nanoliter. In alternative embodiments, reaction volumes of 2 nanoliters to 100 nanoliters can be utilized.

Depending on the geometry of the particular microfluidic device and the size of the microfluidic device and the arrangement of the fluid communication paths and processing site, embodiments of the present invention provide for a range of processing site (or reaction chamber) densities. In some embodiments, the methods and systems of the present invention are utilized with chamber densities ranging from about 100 chambers per $cm^2$ to about 1 million chambers per $cm^2$. Merely by way of example, microfluidic devices with chamber densities of 250, 1,000, 2,500, 10,000, 25,000, 100,000, and 250,000 chambers per $cm^2$ are utilized according to embodiments of the present invention. In some embodiments, chamber densities in excess of 1,000,000 chambers per $cm^2$ are utilized, although this is not required by the present invention.

Operating microfluidic devices with such small reaction volumes reduces reagent usage as well as sample usage. Moreover, some embodiments of the present invention provide methods and systems adapted to perform real-time detection, when used in combination with real-time quantitative PCR. Utilizing these systems and methods, six orders of linear dynamic range are provided for some applications as well as quantitative resolution high enough to allow for the detection of sub-nanoMolar fluorophore concentrations in 10 nanoliter volumes. One of ordinary skill in the art would recognize many variations, modifications, and alternatives.

Methods conducted with certain blind channel type devices involve providing a microfluidic device that comprises a flow channel formed within an elastomeric material; and a plurality of blind flow channels in fluid communication with the flow channel, with an end region of each blind flow channel defining a reaction site or multiple reaction sites formed along the flow channel. At least one reagent is introduced into each of the reaction sites, and then a reaction is detected at one or more of the reaction sites. The method can optionally include heating the at least one reagent within the reaction site. Thus, for example, a method can involve introducing the components for a nucleic acid amplification reaction and then thermocycling the components to form amplified product. As more fully described below, an optical imaging system adapted to characterize reactions occurring in certain microfluidic devices is provided according to embodiments of the present invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It is also to be noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

PNA is peptide nucleic acid
LNA is locked nucleic acid
DA is dynamic array
PCR is polymerase chain reaction
BSA is bovine serum albumin
FRET is fluorescence resonance energy transfer
GT is genotyping
PEG is polyethylene glycol
PLP is padlock probe The term "analyte" as used herein, generally refers to a nucleic acid molecule or mixture of nucleic acid molecules, defined infra, that is to be detected or quantified using the methods of the invention. The terms "target nucleic acid analyte" and "nucleic acid analyte" are used interchangeably with the term "analyte" for the purposes of this invention.

The terms "complementary" or "complementarity" as used herein, may include the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of molecules.

The term "dye" as used herein, generally refers to any organic or inorganic molecule that absorbs electromagnetic radiation at a wavelength greater than or equal 340 nm.

The term "fluorescent dye" as used herein, generally refers to any dye that emits electromagnetic radiation of longer wavelength by a fluorescent mechanism upon irradiation by a source of electromagnetic radiation, such as a lamp, a photodiode, or a laser.

The term "GT sample buffer," as used herein generally refers to a buffer that is capable of blocking binding sites on the surface of the reaction channels and chambers in a DA chip. The buffer protects the reaction components from depletion during the chip loading process or reaction. It may also reduce the usage of additional Taq-Gold Polymerase by less than about 80% for reagent costs. A 20×GT buffer may include a combination of betaine (FW 117.15), BSA, Superblock® T20 (in PBS) (Thermo Scientific, Rockford, Ill.), Superblock® (in PBS) (Thermo Scientific, Rockford, Ill.), Superblock® (in TBS) (Thermo Scientific, Rockford, Ill.), Superblock® T20 (in TBS) (Thermo Scientific, Rockford, Ill.), glycerol, PEG 20,000, PEG MME550, PEG MME5000, and Tween 20.

The term "homogenous assay" as used herein, generally refers to a method to detect or quantify a nucleic acid analyte that requires no post-assay processing to record the result of the assay. The homogenous assays may be carried out in closed tubes or microfluidic arrays where no further addition of reagents or supplementary chemicals are necessary to record the result once the assay is started. Homogenous assays allow recordation of the result of the assay in real time, meaning that the result of the assay can be continuously recorded as the assay progresses in time.

The term "hydrolysis probes" as used herein are generally described in U.S. Pat. No. 5,210,015 incorporated herein by reference in its entirety. Hydrolysis probes take advantage of the 5'-nuclease activity present in the thermostable Taq polymerase enzyme used in the PCR reaction (TaqMan® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe may anneal downstream of one of the primers that defines one end of the amplification target site on the nucleic acid target analyte in the PCR reaction. Using the polymerase activity of the Taq enzyme, amplification of the target nucleic acid analyte is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, the hydrolysis probes of the invention may capable of detecting 8-mer or 9-mer motifs that are common in the human and other transcriptomes and may have a high $T_m$ of about 70° C. enabled by LNA analogs.

The term "label" as used herein refers to any atom or molecule which can be used to provide a detectable and/or quantifiable signal. In particular, the label can be attached to a nucleic acid or protein. Labels may provide signals detectable by fluorescence, radioactivity, colorimetric, X-ray diffraction or absorption, magnetism, enzymatic activity, and the like.

The term "nucleic acid" as used herein generally refers to cDNA, DNA, RNA, single-stranded or double-stranded and any chemical modification thereof, such as PNA and LNA. LNAs are described in U.S. Pat. Nos. 6,794,499, 6,670,461, 6,262,490, and 6,770,748 herein incorporated by reference in their entirety. Nucleic acids may be of any size. Nucleic acid modifications may include addition of chemical groups that incorporate additional charge, polarizability, hydrogen bonding, electrostatic interaction, and functionality to the individual nucleic acid bases or to the nucleic acid as a whole. Such modifications may include modified bases such as 2'-position sugar modifications, 5-position pyrimidine modifications, 8-position purine modifications, modifications at cytosine exocylcic amines, substitutions of 5-bromo-uracil, backbone modifications, methylations, unusual base pairing combinations such as the isobases isocytidine and isoguanidine and the like. The nucleic acid can be derived from a completely chemical synthesis process, such as a solid phase mediated chemical synthesis, or from a biological origin, such as through isolation from almost any species that can provide nucleic acid, or from processes that involve the manipulation of nucleic acids by molecular biology tools, such as DNA replication, PCR amplification, reverse transcription, or from a combination of those processes.

The term "nucleic acid probe" as used herein is a nucleic acid that carriers at least one covalently attached dye, such as a fluorescent dye. In particular, the probe does not contain a sequence complementary to sequences used to prime the PCR reaction.

The term "padlock probe" or "PLP" as used herein, generally refers to linear oligonucleotides having a length of about 100 base pairs. The sequences at the 3' and 5' ends of the PLP are complementary to adjacent sequences in the target nucleic acid analyte. In the central, noncomplementary region of the PLP there is a "tag sequence" that may be used to identify the specific PLP. The tag sequence may be flanked by universal primer sites or unique and/or specific primer sites, which allow PCR amplification of the tag sequence. Upon hybridization to the target, the 5' and 3' ends of the PLP are brought into close proximity and may be subsequently ligated. The resulting product is a circular probe molecule catenated to the target nucleic acid analyte. The tag regions of circularized PLPs may be amplified and quantified and/or detected using TAQMAN® Real Time PCR, for example. The presence and amount of amplicon may be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8. The above references are incorporated by reference herein in their entirety.

The teem "PCR," as used herein, generally refers to a method for amplifying, detecting, or quantifying a specific region of an analyte. One skilled in the art appreciates that there are several variations on the basic PCR technique such as allele-specific PCR, assembly PCR or polymerase cycling assembly (PCA), colony PCR, helicase-dependent amplification, hot start PCR, intersequence-specific (ISSR) PCR, inverse PCR, ligation-mediated PCR, methylation-specific PCR, multiplex ligation dependent probe amplification, multiplex PCR, nested PCR, overlap-extension PCR, quantitative PCR, quantitative real-time PCR, RT-PCR, thermal asymmetric interlaces (TAIL) PCR, touchdown PCR, and PAN-AC. Additionally, one skilled in the art would understand how to practice these variations on the basic PCR technique.

The phase "preliminary amplification reaction" as used herein, generally refers to processes for preparing the sample prior to running the homogenous assay. The term "pre-amplified sample" may be used interchangeably with the phrase "preliminary amplification reaction" for the purposes of the invention herein.

The term "purification," as used herein, generally refers to any process by which proteins, polypeptides, or nucleic acids are separated from other elements or compounds on the basis of charge, molecular size, or binding affinity.

The term "quencher" as used herein, generally refers to dye that reduces the emission of fluorescence of another dye.

The term "querying" as used herein, generally refers to determining whether a target-specific probe is associated with (e.g., bound to or catenated with) the nucleic acid analyte, and optionally quantifying the amount of target-specific probe in the sample.

A "sample" as used herein, generally refers to a sample of tissue or fluid from a human or animal including, but not limited to plasma, serum, spinal fluid, lymph fluid, the external sections of the skin, respiratory, intestinal and genitourinary tracts, tears, saliva, blood cells, tumors, organs, tissue and sample of in vitro cell culture constituents. In particular, the sample may be single cells, paraffin embedded tissue samples, and needle biopsies. Moreover, a sample may include environmental samples such as lake water, and food samples.

The phrase "substantially purified," or "substantially isolated," as used herein generally includes nucleic or amino acid sequences that are removed from their natural environment, isolated or separated, and are at least about 60% free, specifically at least about 75% free, and most specifically at least about 90% free from other components with which they may be associated with, and includes recombinant or cloned nucleic acid isolates and chemically synthesized analogs or analogs biologically synthesized by systems.

Given the tremendous diversity of polymer chemistries, precursors, synthetic methods, reaction conditions, and potential additives, there are a huge number of possible elastomer systems that could be used to make elastomeric blocks, layers, membranes, microvalves, pumps, and the like. Variations in the materials used may in some cases be driven by the need for particular material properties, i.e., solvent resistance, stiffness, gas permeability, or temperature stability. There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones or polysiloxanes.

Polyisoprene, polybutadiene, and polychloroprene are all polymerized from diene monomers, and therefore have one double bond per monomer when polymerized. This double bond allows the polymers to be converted to elastomers by vulcanization (generally, sulfur is used to form crosslinks between the double bonds by heating). This would easily allow homogeneous multilayer soft lithography by incomplete vulcanization of the layers to be bonded; photoresist encapsulation would be possible by a similar mechanism.

Pure polyisobutylene has no double bonds, but is crosslinked to use as an elastomer by including a small amount (.about.1%) of isoprene in the polymerization. The isoprene monomers give pendant double bonds on the polyisobutylene backbone, which may then be vulcanized as above.

Poly(styrene-butadiene-styrene) is produced by living anionic polymerization (that is, there is no natural chain-terminating step in the reaction), so "live" polymer ends can exist in the cured polymer. This makes it a natural candidate for a photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes are produced from di-isocyanates (A—A) and di-alcohols or di-amines (B—B); since there are a large variety of di-isocyanates and di-alcohols/amines, the number of different types of polyurethanes is huge. The A vs. B nature of the polymers, however, make them useful for heterogeneous multilayer soft lithography just as RTV 615 is: by using excess A—A in one layer and excess B—B in the other layer.

Allcock et al, Contemporary Polymer Chemistry, 2nd Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Materials having a Young's modulus of between about 1 Pa to about 1 TPa, or between about 10 Pa to about 100 GPa, or between about 20 Pa to about 1 GPa, or between about 50 Pa to about 10 MPa, or between about 100 Pa to about 1 MPa are useful in accordance with embodiments of the present invention, although materials having a Young's modulus outside of these ranges could also be utilized depending upon the needs of a particular application. In some cases, materials can have a Young's modulus of about 100 MPA (megapascals) or less. In other embodiments, the Young's modulus of the material is about 75 MPA or less, about 50 MPa or less, about 25 MPa or less, about 10 MPa or less, about 8 MPa or less, about 5 MPa or less, or about 2 MPa or less.

Embodiments of the present invention provide a microfluidic device that includes features such as channels, valves, and chambers, that are at least partially contained, embedded, or formed by or within one or more layers and/or levels. Such layers and/or levels can be made from various materials, such as an elastomeric material. An exemplary microfluidic device has a reagent flow channel, or reagent line, formed in a first layer. The reagent flow channel includes a containment valve and a chamber conduit. The microfluidic device may also have a control channel, or containment line, formed in a second layer adjacent to the first layer. Further, the microfluidic device may contain a sample flow channel, or sample line, formed in a third layer adjacent to the second layer. The sample flow channel may include a containment valve and a chamber conduit. The control channel can be in operative association with both the reagent flow channel containment valve and the sample flow channel containment valve. The microfluidic device can include a reagent chamber in fluid communication with the reagent line, and a sample chamber in fluid communication with the sample line. The reagent chamber and the sample chamber may be in fluid communication with each other by way of a reaction flow channel or reaction line, formed in the third layer. The reaction line may include an interface valve. The microfluidic device may also include an interface channel formed in a fourth layer adjacent to the third layer. The interface channel can be in operative association with the reaction flow channel interface valve.

Embodiments of the present invention also encompass methods of making and using the microfluidic devices disclosed herein. For example, operation of a microfluidic device can involve opening one or more isolation valves, closing one or more interface valves, and flowing material past the isolation valves and into one or more chambers, optionally under pressure. Techniques may also include changing the pressure in a containment line to close the isolation valves, so as to seal off the individual chambers, and changing the pressure in an interface line, so as to open an interface valve. A first material in a first chamber can flow past an open interface valve and into a second chamber, where the first material mixes or reacts with a second material contained therein.

Exemplarly Fabrication Methods

The methods used in fabrication of a microfluidic device may vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, modular assembly methods, replica molding methods, injection molding methods, hot molding methods, laser ablation methods, combinations of methods, and other methods known in the art or developed in the future. A variety of exemplary fabrication methods are described in Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rossier et al., 2002, "Plasma etched polymer microelectrochemical systems" *Lab Chip* 2:145-150; Becker et al., 2002, "Polymer microfluidic devices" *Talanta* 56:267-287; Becker et al., 2000, "Polymer microfabrication methods for microfluidic analytical applications" Electrophoresis 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, *IEEE Trans. on Electron Devices*, v. ED-26, pp. 1880-1886; Berg et al., 1994, Micro Total Analysis Systems, New York, Kluwer; Webster et al., 1996, *Monolithic Capillary Gel Electrophoresis Stage with On-Chip Detector in International Conference On Micro Electromechanical Systems, MEMS* 96, pp. 491496; and Mastrangelo et al., 1989, *Vacuum-Sealed Silicon Micromachined Incandescent Light Source*, in Intl. Electron Devices Meeting, *IDEM* 89, pp. 503-506. Each of these references are incorporated herein by reference for all purposes.

In preferred embodiments, the device is fabricated using elastomeric materials. Fabrication methods using elastomeric materials and methods for design of devices and their components have been described in detail in the scientific and patent literature. See, e.g., Unger et al., 2000, *Science* 288: 113-16; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic systems including three-dimensionally arrayed channel networks); U.S. Patent Application publication Nos. 2004/0115838, 2005/0072946; 2005/0000900; 2002/0127736; 2002/0109114; 2004/0115838; 2003/0138829; 2002/0164816; 2002/0127736; and 2002/0109114; PCT patent publications WO 2005/084191; WO 05030822A2; and WO 01/01025; Quake & Scherer, 2000, "From micro to nanofabrication with soft materials" *Science* 290: 1536-40; Xia et al., 1998, "Soft lithography" Angewandte Chemie-International Edition 37:551-575; Unger et al., 2000, "Monolithic microfabricated valves and pumps by multilayer soft lithography" *Science* 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" *Analytical Chemistry* 75, 4718-23," Hong et al, 2004, "A nanoliter-scale nucleic acid processor with parallel architecture" *Nature Biotechnology* 22:435-39; Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rolland et al., 2004, "Solvent-resistant photocurable "liquid Teflon" for microfluidic device fabrication" *J. Amer. Chem. Soc.* 126:2322-2323; Rossier et al., 2002, "Plasma etched polymer microelectrochemical systems" Lab Chip 2:145-150; Becker et al., 2002, "Polymer microfluidic devices" Talanta 56:267-287; Becker et al., 2000, and other references cited herein and found in the scientific and patent literature. Each of these references are incorporated herein by reference for all purposes.

Embodiments of the present invention further encompass aspects of microfluidic fabrication and production, as well as microfluidic device operation and use, as disclosed in U.S. patent application Ser. No. 12/018,138 filed Jan. 22, 2008, the content of which is incorporated herein by reference for all purposes.

Any of a variety of ablation, etching, or similar techniques can be used to form vias or passages in an elastomeric block, membrane, or layer. Such etching procedures are well suited for creating elastomeric layers having multiple holes or apertures, for example. In an exemplary process, an elastomeric material is placed on a wafer or mold, and allowed to cure. The elastomeric material can include one or more polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical may also be used. In some cases, the elastomeric material is deposited on the wafer or mold in a spin coating process, a spray coating process, a dip coating process, a screen printing process, an inkjet deposition process, or the like. The curing procedure can involve baking or room temperature vulcanizing (RTV), photocuring, and the like.

An elastomeric composition may include multiple parts, which can be mixed together at various ratios to obtain desired bond properties. For example, an elastomeric material may include a Part A and a Part B, which when mixed together in prescribed amounts facilitates the desired bond parameters. In some cases, the parts may be mixed in a ratio within a range from about 3:1 to about 30:1. For example, an elastomeric PDMS composition is baked to provide a 10:1 RTV layer.

In some cases, a photoresist material can be placed on the cured elastomeric material. For example, an SU-8 resist (available from MicroChem Corp., Newton Mass.) can be applied to the elastomer. Exemplary SU-8 resists include SU-8 2000, SU-8 3000, SU-8 2007, SU-8 3005, and the like. The photoresist can be deposited on the elastomeric material in a spin coating procedure, at a desired rotational speed and duration. In some cases, the spin coating can be performed at a rotational speed within a range from about 1000 to about 10,000 rpm, and for a duration within a range from about 20 seconds to about 2,000 seconds. For example, the spin coating can be performed at 5000 rpm for 200 seconds. Following this deposition, the photoresist mask can have a thickness or depth within a range from about 0.5 to about 50 microns. In some cases, the thickness is about 5 microns. The thickness of the mask can be selected for facile via opening formation, and the selected spin time can eliminate or inhibit beading of the photoresist material. The photoresist material can be used as an etch mask.

Additional procedures can be performed to prepare the photoresist for lithography exposure. For example, the photoresist can be processed at a selected temperature for a selected time duration. In some embodiments, the photoresist is soft baked at a temperature within a range from about 45° C. to about 85° C. Relatedly, the photoresist can be baked for a duration within a range from about 1 minute to about 10 minutes. In some cases, the soft bake is performed for 5 minutes at 65° C. Such preparation techniques can help to eliminate or inhibit photoresist mask cracking at exposure.

The preparation procedure may also include cooling the photoresist. For example, the photoresist may be cooled at room temperature or at a temperature within a range from about 18° C. to about 37° C., and for a duration within a range from about 3 minutes to about 300 minutes. In some cases, the photoresist is cooled for about 30 minutes.

The lithography procedure can involve multiple exposure steps. For example, a first exposure step can be performed with a first exposure mask, and a second subsequent exposure step can be performed with a second exposure mask. An exposure step can involve the application of radiation or energy, through an exposure mask, toward a photoresist. Exposure radiation can include ultraviolet light, near ultraviolet light, deep ultraviolet light, visible light, infrared light, or energy at any desired wavelength along the electromagnetic spectrum. In some cases, exposure radiation is delivered at one or more wavelengths within a range from about 10 to about $10^{-9}$ cm. In some cases, the type of radiation or energy is selected based on the composition of the photoresist. For example, specific types of radiation or energy can be applied to I-line photoresists, G-line photoresists, H-line photoresists, and the like.

The use of multiple masks can help to prevent or inhibit the effect of contaminants on a mask from replicating on the photoresist. For example, if there is an unwanted particle on the first mask at a certain location, exposure with a second mask can help to ensure exposure of the photoresist at that location. The exposure process can be followed with a post-exposure bake (PEB) procedure. In some cases, a PEB procedure is performed for a duration within a range from about 0 to about 200 minutes, and at a temperature within a range from about 50° C. to about 80° C. For example, a PEB can be performed for 2 minutes at 65° C. In some cases, the PEB can operate to cross-link the photoresist mask material, rendering the material nonsoluble. Thereafter, the exposed photoresist can be allowed to cool. An exemplary cooling process is performed at a temperature within a range from about 18° C. to about 37° C. for a duration within a range from about 1 hour to about 40 hours. In some cases, the exposed photoresist is cooled at room temperature for about 18 hours.

A development process can be performed following exposure. In some cases, the photoresist mask is developed for a duration within a range from about 10 seconds to about 10 minutes. During the development process a developer is applied to the exposed photoresist. The developer can include, for example, an organic solvent such as acetate. It is understood that the developer or solvent may be selected based on the composition of the photoresist. The developer can operate to dissolve or degrade areas or locations of the photoresist layer that were unexposed or masked during the exposure process. Following development, the photoresist mask is subject to a drying procedure. For example, the mask can be spin-dried. The mask may also be allowed to relax for a desired period of time. In some cases, the mask is allowed to relax at or near room temperature for a duration within a range from about 1 minute to about 48 hours.

Optionally, additional elastomeric layers can be spin-coated or otherwise applied onto the developed photoresist. For example, an RTV coating have a thickness or depth within a range from about 0.3 microns to about 30 microns can be deposited on the photoresist mask. The elastomeric coating can be baked for a duration within a range from about 5 minutes to about 3 hours, at a temperature within a range from about 40° C. to about 80° C. In some cases, a 3 micron RTV coating is spin-coated on an SU-8 mask, and baked for 1 hour at 60° C. Such techniques can help to minimize lateral etch, and reduce via size non-uniformity. The RTV layer can be deposited on a patterned photoresist layer, to help prevent or inhibit the formation of pinholes in the underlying elastomer.

Typically, etching involves removing certain areas of the elastomeric material that are not protected by the photoresist following development. In an exemplary procedure, etching can be performed for a duration within a range from about 1 minute to about 20 minutes and at a temperature within a range from about 50° C. to about 90° C. For example, etching can be carried out in an 80% tetrabutylammonium fluoride (TBAF) etchant solution for 6-8 minutes at 70 degrees ° C. In some cases, etching is performed in an ultrasonic bath tank, optionally in degas mode. Such procedures can help to ensure a uniform etching depth, with minimum damage to a photoresist mask during the etching procedure. Etching can be followed with a deionized water wash. In some cases, a hot water wash is performed for three minutes. The photoresist mask can be removed with adhesive tape. A deionized water wash can be applied again, optionally for 3 minutes. Stacking procedures can provide additional layers to the elastomer. In some cases, adjacent layers adhere to one another by way of interlayer bonding.

Turning now to the drawings, FIG. 1 depicts a perspective view of a unit cell 100 of a microfluidic device, according to some embodiments. Unit cell 100 includes a first channel 130, a first isolation valve 132, a first chamber 140, a second channel 110, a second isolation valve 112, a second chamber 120, a control channel 150, an interface channel 160, an interface valve 162, and a reaction channel 170. Typically, these features are at least partially contained, embedded, or formed by or within an elastomeric block 180. As shown here, first channel 130 is at least partially disposed within a first layer 181 of elastomeric block 180.

Figure 1A:
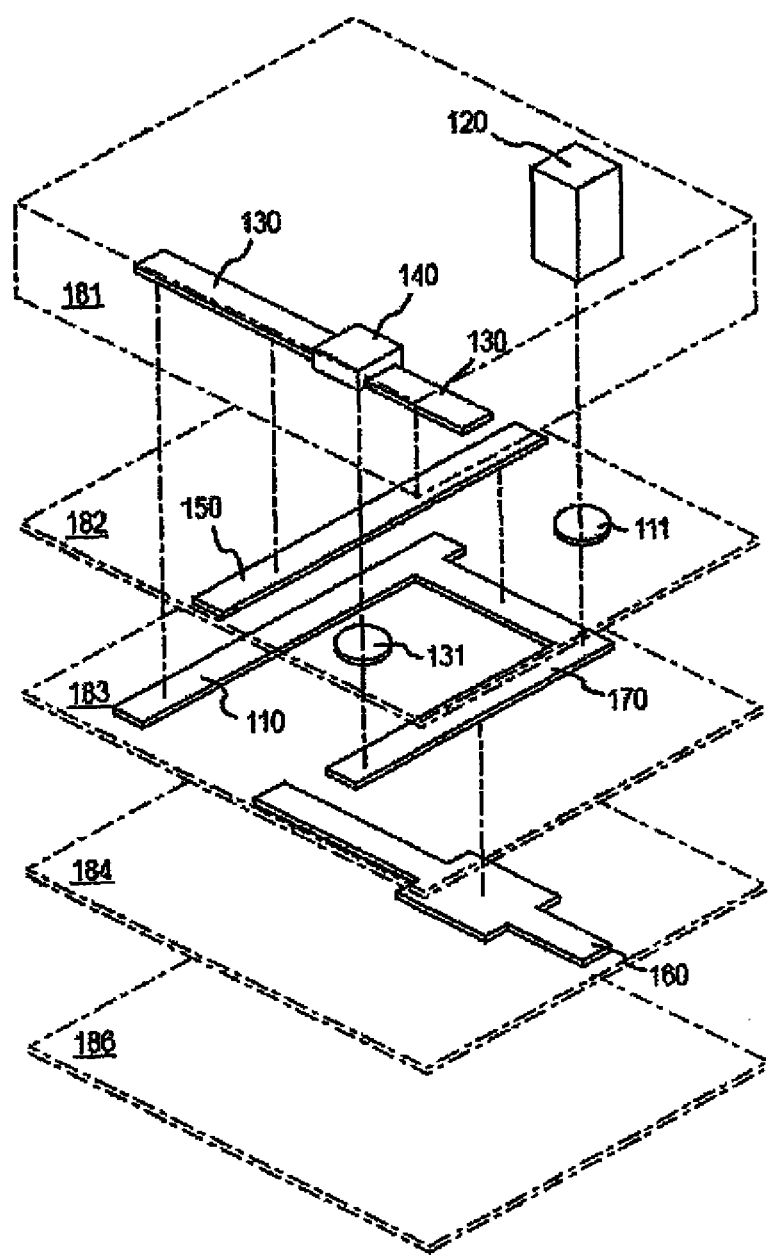
FIG. 1A shows an exploded perspective view of individual layers of a unit cell of a microfluidic device according to embodiments of the present invention.

FIG. 1A shows an exploded perspective view of individual layers of a unit cell 100 of a microfluidic device, according to embodiments of the present invention. Each layer typically includes an elastomeric membrane with one or more recesses, channels, chambers, or the like. As depicted here, the first layer 181 of unit cell 100 includes the first channel 130 in fluid communication with the first chamber 140. The first layer 181 also includes the second chamber 120. Second layer 182 includes the control channel 150, a first via 111, and a second via 131. The third layer 183 includes a second channel 110 and a reaction channel 170. As further discussed elsewhere herein, unit cell 100 can be configured so that second channel 110 and reaction channel 170 are in fluid communication with second chamber 120, optionally by way of via 111. For example, creating a fluid passage that extends from second channel 110 to reaction channel 170 can involve removing a portion of second layer 182 that is disposed below second chamber 120. Creation of this fluid passage can also involve removing a corresponding portion of third layer 183 that is disposed below second chamber 120. Similarly, unit cell 100 can be configured so that reaction channel 170 is in fluid communication with first chamber 140, optionally by way of via 131. For example, creating a fluid passage that extends from first channel 130 to reaction channel 170 can involve removing a portion of second layer 182 that is disposed below first chamber 140. Creation of this fluid passage can also involve removing a corresponding portion of third layer 183 that is disposed below first chamber 140. Fourth layer 184 includes an interface channel 160.

Hence, as shown here, first channel 130 is at least partially contained within a first layer 181. Control channel 150, via 111, and via 131 are each at least partially contained within a second layer 182, where the second layer is adjacent to the first layer. Second channel 110 and reaction channel 170 are at least partially contained within a third layer 183, where the third layer is adjacent to the second layer. As shown here, vias 131, 111 are disposed in second layer 182. It is understood that corresponding vias can be formed in third layer 183, so as to provide fluid communication from chamber 140 through via 131 and into channel 170, and fluid communication from chamber 120 through via 111 and into the intersection of channels 110 and 170. Interface channel 160 is at least partially contained within a fourth layer 184, where the fourth layer is adjacent to the third layer. First chamber 140 is at least partially contained within first layer 181. First chamber 140 in some instances can also be least partially contained within or in communication with passages located in second layer 182 and third layer 183, thus providing fluid communication between first chamber 140 and first channel 130, and between first chamber 140 and reaction channel 170. Second chamber 120 is at least partially contained within first layer 181. In some instances second chamber 120 can be at least partially contained within or in communication with passages located in second layer 182 and third layer 183, thus providing fluid communication between second chamber 120 and reaction channel 170.

With reference to the "A" arrows in FIG. 1, a first material, such as an assay reagent, can flow through first channel 130, past first isolation valve 132, and into first chamber 140. Similarly, with reference to the "B" arrows, a second material, such as an assay sample, can flow through second channel 110, past second isolation valve 112, through via 111, and into second chamber 120. To allow flow into the reaction chambers 140, 120, first and second isolation valves 132, 112, respectively, are both in a normally open valve state. To prevent or inhibit flow between first reaction chamber 140 and second reaction chamber 120 through reaction channel 170, interface valve 162 is in a normally closed valve state. Under such conditions, first channel 130 is in open fluid communication with first reaction chamber 140, and second channel 110 is in fluid communication with second reaction chamber 120, whereas fluid communication between the first and second chambers is interrupted or inhibited. Reaction chamber sizes may vary. In some embodiments, the volume of second reaction chamber 120 is different or greater than the volume of first reaction chamber 140. For example, the volume of second reaction chamber 120 can be ten times greater than the volume of first reaction chamber 140. Materials can be loaded into their respective chambers under pressure. Relatedly, materials can be loaded into chambers at certain concentrations. In some cases, a reagent solution is loaded into a chamber at a 10× concentration, and is then diluted when reacted with a sample solution contained in another chamber.

After the first and second materials have been loaded into first and second reaction chambers 140, 120 respectively, the control channel 150 can be activated, for example by pressurizing the control channel, so as to transform each of first and second isolation valves 132, 112 from an open valve state to a closed valve state. In this way the materials can be confined, optionally under pressure, within the reaction chambers. Hence, it is understood that a single control channel, for example control channel 150, can control flow of a first material into a first reaction chamber, and can also control flow of a second material into a second reaction chamber. Operation of a single control channel can thus act to isolate a first volume of material or solution within the first chamber via actuation of the first isolation valve 132, and can also isolate a second volume of material or solution within the second chamber via actuation of the second isolation valve 112. Relatedly, operation of a single control channel can cause a first deflection in a first direction at first isolation valve 132, and a second deflection in a second direction at second isolation valve 112, where first direction is opposite to second direction. For example, the deflection in the first isolation valve can be in the upward direction, and the deflection in the second isolation valve can be in the downward direction. Accordingly, control of more than one isolation valve can be effected simultaneously by operation of the single control channel. Materials can be confined within the reaction chambers under any suitable amount of pressure. In some embodiments, the pressure in the first reaction chamber 140 is different or greater than the pressure in the second reaction chamber 120. For example, a first material such as a reagent can be disposed in first reaction chamber 140 at a first pressure that is within a range from about 0 psi to about 15 psi. Relatedly, a second material such as a sample can be disposed in second reaction chamber 120 at a second pressure that is within a range from about 0 psi to about 10 psi. In some instances, material can be contained in the first reaction chamber 140 at about 10 psi, and material can be contained in the second reaction chamber 120 at about 0 psi. Often, loading of the microfluidic device involves introducing material into first channel 130 or second channel 110, or both, under pressure. A pressurizing mechanism (as are know in the art) can be used to drive materials into the chambers.

In some cases, embodiments are directed to systems and methods for conducting one or more reactions at one or more selected temperatures or ranges of temperatures over time. A microfluidic system may include a plurality of separate reaction chambers formed in a multi-layer elastomeric block. The system may also include a thermal transfer device proximal to or near at least one of the reaction chambers. The thermal transfer device can be formed to contact a thermal control source. Reagents for carrying out a desired reaction can be introduced into a microfluidic array device or matrix. The array device or matrix can be contacted with the thermal control device such that the thermal control device is in thermal communication with the thermal control source so that a temperature of the reaction in at least one of the reaction chamber is changed or controlled as a result of a change in temperature of thermal control source. Exemplary thermal cycling techniques are discussed in U.S. Patent Publication No. 2007/0196912, the content of which is incorporated herein by reference. In some embodiments, a microfluidic device or chip can be coupled with or in operative association with an Integrated Heat Spreader (IHS). Such heating mechanisms are discussed in U.S. Pat. No. 7,307,802, the content of which is incorporated herein by reference.

In some cases, passages or vias can be formed between channels or chambers at one layer and channels or chambers at another layer. For example, it is possible to create a via 131 through second layer 182 to provide fluid communication between first chamber 140 in first layer 181 and reaction channel 170 in third layer 183. Similarly, it is possible to create a via 111 through second layer 182 to provide fluid communication between second chamber 120 in first layer 181 and second channel 110 and reaction channel 170 in third layer 183. In some instances, creation of these vias can enlarge the volume of the reaction chambers. In some cases, the vias can be formed by using a laser punch to remove or ablate portions of elastomeric membrane. As shown in FIG. 1A, for example, reaction chambers 120, 140 can have an interior space that extends above a plane defined by the top of first channel 130. This interior space can also extend above a plane defined by the top of second channel 110, and above a plane defined by the top of reaction channel 170. Hence, during loading of the unit cell, fluid can flow through first channel 130 and upward into the interior of first chamber 140. Similarly, during loading, fluid can flow through second channel 110 and upward into the interior of second chamber 120, optionally through a via formed in the second layer. Relatedly, during a mixing operation, fluid can flow from the interior of first chamber 140 and downward into reaction channel 170, optionally through a via 131 formed in the second layer. Similarly, during a mixing operation fluid can flow from reaction channel 170 and upward into the interior of second chamber 120, optionally through a via 111 formed in the second layer.

According to the embodiment shown in FIG. 1, reaction channel 170 and interface valve 162 are not located within the same plane or layer as first chamber 140 and second chamber 120. For example, reaction channel 170 is disposed in third layer 183, interface valve 162 operates at or near the boundary or junction between fourth layer 184 and third layer 183, and first and second chambers 140, 120 are disposed in first layer 181. As the routing passage or reaction channel 170 passes in a lower or different layer than that of the chambers, this allows the chambers to be located in close proximity with one another. In some embodiments, a sidewall of first chamber 140 and a facing sidewall of second chamber 120 are separated by a distance of about 120 microns. In related embodiments, a distance between facing sidewalls of first and second chambers is within a range from about 40 microns to about 225 microns. For example, a first chamber sidewall and a facing second chamber sidewall can be separated by a distance of about 50 microns, about 60 microns, about 70 microns, or about 80 microns. Often, interface valve 162 is about 50 microns in width. Hence, the distance between facing sidewalls of first and second chambers can be less than, about the same as, or more than the diameter or width of the interface valve which controls or modulates flow between the chambers. Accordingly, microfluidic devices employing such architecture can present extremely large numbers of chambers within a given area. Such high densities may be difficult to achieve in situations where a valve that controls flow between two chambers is disposed in the same layer as the chambers.

The chambers 140 and 120 may have varied dimensions and volumes. In an embodiment, first chamber 140 may have a width within a range from about 25 microns to about 75 microns, a length within a range from about 80 microns to about 240 microns, and a height within a range from about 30 microns to about 90 microns. Relatedly, first chamber 140 may have a volume within a range from about 0.1 nanoliters to about 10 nanoliters. For example, first chamber 140 can have a width of 50 microns, a length of 162.5 microns, a height of 60 microns, and a volume of 0.49 nanoliters. Second chamber 120 can have a width within a range from about 70 microns to about 210 microns, a length within a range from about 80 microns to about 240 microns, and a height within a range from about 150 microns to about 450 microns. Relatedly, second chamber 120 can have a volume within a range from about 1 nanoliter to about 20 nanoliters. For example, second chamber 120 can have a width of 137.5 microns, a length of 162.5 microns, a height of 300 microns, and a volume of 6.7 nanoliters. A microfluidic device according to embodiments of the present invention can provide a center-to-center distance between first chamber 120 and second chamber of about 300 microns. In some cases, this center-to-center distance is within a range from about 250 microns to about 350 microns. Optionally, the center-to-center distance between the first chamber and the second chamber is about 312.5 microns.

Microfluidic devices can be fabricated using a variety of methods. The attached Appendix contains additional discussion of related fabrication methods.

Figure 1B:
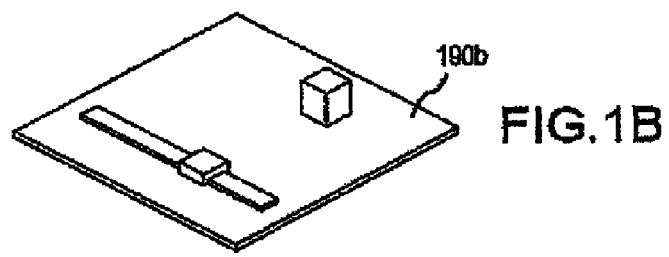
FIGS. 1B to 1E show microfluidic molds according to embodiments of the present invention.
Figure 1C:
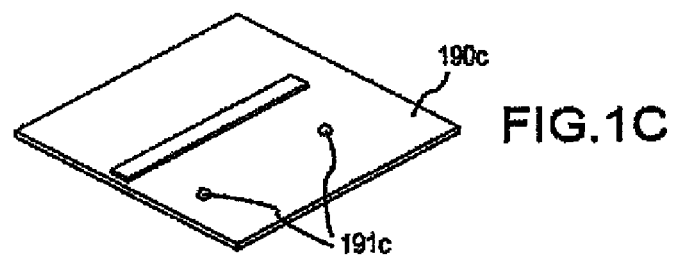
Figure 1D:
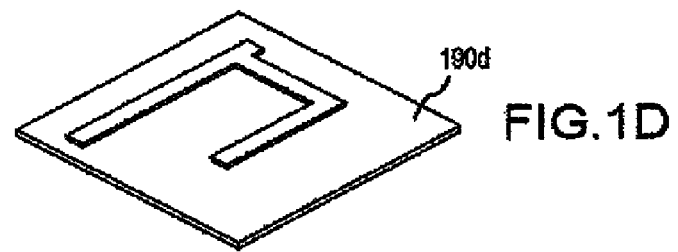
Figure 1E:
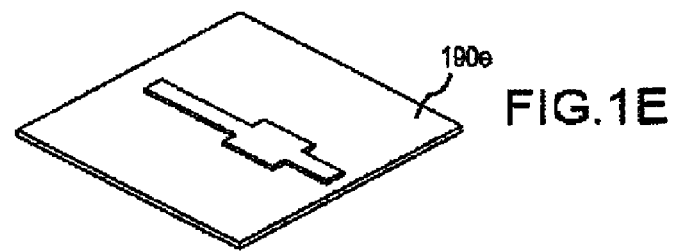

In some embodiments, a microfluidic device can include one or more layers that have been prepared according to spin or pour fabrication protocols. For example, a spin protocol can involve placing a polymeric material on a patterned disc or mold, and spinning the disc to create a layer of polymer across the disc. Exemplary polymers include polymethylmethacrylate, polystyrene, polypropylene, polyester, fluoropolymers, polytetrafluoroethylene, polycarbonate, polysilicon, and polydimethylsiloxane (PDMS). A pour protocol can involve pouring a PDMS material, for example, on a patterned template or mold, which can result in a layer of PDMS which can be peeled or pulled off the mold intact. Often, a layer prepared by a pour fabrication technique is thicker than a layer prepared by a spin fabrication technique. Elastomeric blocks can include one or more pour or spin layers, in any desired combination. In some embodiments, first layer 181 can be fabricated according to a pour protocol. For example, PDMS can be poured onto a mold that has raised portions corresponding to the various desired fluid flow channels and chambers. FIG. 1B shows an exemplary mold 190*b* which can be used to fabricate first layer 181 of FIG. 1A. After curing, the first layer can be peeled away from the mold. First layer 181 can include openings, recesses, or other voids that at least partially form or define first channel 130, first chamber 140, and second chamber 120. To create second layer 182, PDMS can be placed onto a mold that has raised portions corresponding to the various desired containment or control channels. FIG. 1C shows an exemplary mold 190*c* which can be used to fabricate second layer 182 of FIG. 1A. Mold 190*c* can also include, for example, raised or contoured portions 191*c* that form corresponding marks in second layer 182. These marks can be used during a laser ablation procedure, such that the laser ablation is directed toward the marks during the ablation. Mold 190*c* can be spun, so as to provide a thin layer of PDMS across the mold. Second layer 182 can include openings, recesses, or other voids that at least partially form or define control channel 150. In some cases, second layer 182 can be exposed to one or more laser ablations. An ablative laser beam directed to second layer 182 can form vias 111, 131. After second layer 182 is sufficiently cured, first layer 181 can be aligned and contacted with the second layer. The first layer can adhere with the second layer, and both layers can be peeled off mold 190*c* simultaneously. To create third layer 183, PDMS can be placed onto a mold that has raised portions corresponding to the various desired containment or control channels. FIG. 1D shows an exemplary mold 190*d* which can be used to fabricate third layer 183 of FIG. 1A. The mold can be spun, so as to provide a thin layer of PDMS across the mold. Third layer 183 can include openings, recesses, or other voids that at least partially form or define second channel 110 and reaction channel 170. After third layer 183 is sufficiently cured, the combined first layer 181 and second layer 182 can be aligned and contacted with the third layer. The third layer can adhere with the second layer, and all three layers can be peeled off mold 190*d* simultaneously. To create fourth layer 184, PDMS can be placed onto a mold that has raised portions corresponding to the various desired containment or control channels. FIG. 1E shows an exemplary mold 190*e* which can be used to fabricate fourth layer 184 of FIG. 1A. The mold can be spun, so as to provide a thin layer of PDMS across the mold. Fourth layer 184 can include openings, recesses, or other voids that at least partially form or define interface channel 160. After fourth layer 184 is sufficiently cured, the combined first layer 181, second layer 182, and third layer 183 can be aligned and contacted with the fourth layer. The fourth layer can adhere with the third layer, and all four layers can be peeled off mold 190*e* simultaneously. Optionally, the four layers can be placed on or contacted with a fifth layer 186 as shown in FIG. 1A. The fifth layer 186 can include a laminate or tape, or a similarly suitable material, which operates to seal a recess in the fourth layer, so as to form or seal interface channel 160. In this way, the combined first, second, third, and fourth layers 181, 182, 183, 184 can then be placed on or contacted with the fifth layer 186, which may be a solid spin layer. The fifth layer 186 can act as a sealing layer. According to some embodiments, the fifth layer 186 may include an elastomeric material, such as PDMS. In some cases, the fifth layer 186 can include a rigid or hard material such as glass, silicon, or a plastic such as polystyrene. The fifth layer 186 may, for example, seal recesses formed in bottom of the fourth layer, so as to provide channels in the fourth layer 184. The fifth layer 186 can include a film which may be attached to the fourth layer 184 via an adhesive. Hence, a sealing layer can form channels from recesses molded or machined into an adjacent layer. A sealing layer can be a transparent material, for example, polystyrene, polycarbonate, or polypropylene. Relatedly, a sealing layer can be flexible, such as an adhesive tape, and may be suitable for attachment to a substrate by bonding, such as with adhesive or heat sealing, or mechanically attached such as by compression. Often, materials used to fabricate a sealing layer are compliant to form fluidic seals with each recess to form a fluidic channel with minimal leakage. A sealing layer may further be supported by an additional support layer that is rigid (not shown). In some cases, a sealing layer is rigid.

According to embodiments of the present invention, the second, third, fourth, and fifth layers can be processed or laser punched as part of a procedure that forms a loading passage to first channel 130 in first layer 181. Relatedly, the fourth and fifth layers can be processed or laser punched as part of a procedure that forms a loading passage to second channel 110 in third layer 183. Loading passages, vias, and the like can be formed using a drilling or ablation mechanism. For example, a loading passage or via can be fabricated by ablating a portion of the elastomeric block. Excimer lasers are well suited for such ablation techniques, as they can produce a laser beam which removes a portion of the elastomeric block. In some cases, loading passages or vias, or portions thereof, can be formed before one or more of the individual layers are adhered together. For example, a portion of a loading passage or via can be formed in a layer during the molding process, or after the molding process and before the adhesion process. Optionally, formation of at least a portion of the loading passage or via can involve etching one or more elastomeric layers prior to forming the complete multilayer elastomeric block.

Figure 2:
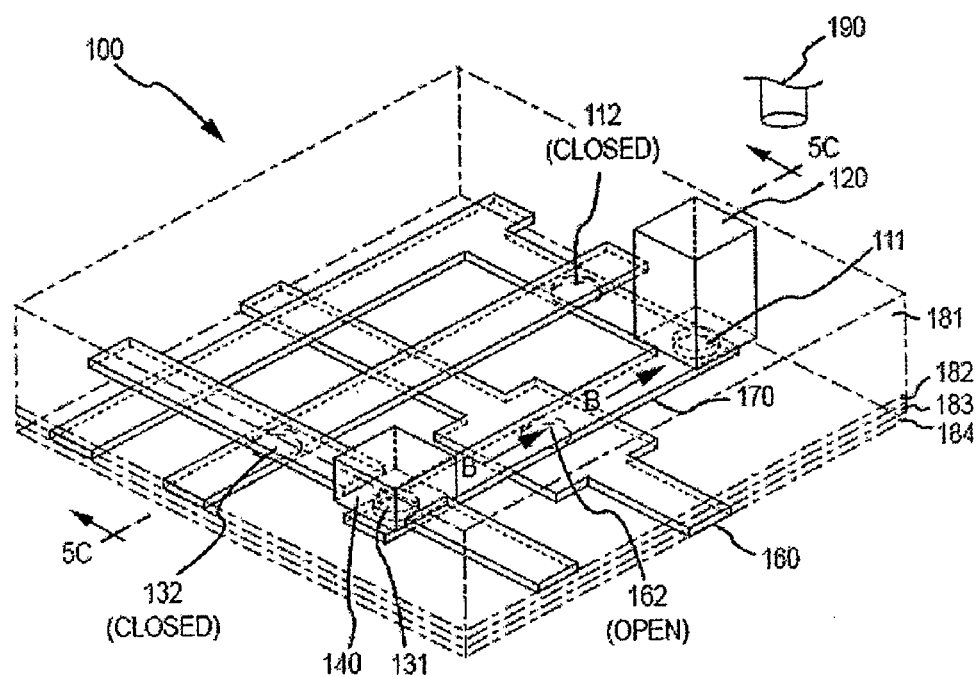
FIG. 2 illustrates a perspective view of the unit cell of FIG. 1, showing a flow path between two chambers.

FIG. 2 illustrates another perspective view of unit cell 100. As shown here with reference to the "B" arrows, the first material can flow from first reaction chamber 140, through via 131, through reaction channel 170, past interface valve 162, through via 111, and into second reaction chamber 120, where the first material can contact the second material. It is understood that in some embodiments, the second material can flow from second reaction chamber 120, through via 111, through reaction channel 170, past interface valve 162, through via 131, and into first reaction chamber. To allow such flow through reaction channel 170, the interface channel 160 can be activated so as to transform interface valve 162 from a closed valve state to an open valve state. Under such conditions, the first and second reaction chambers 140, 120 are in open fluid communication by way of the reaction channel and the vias. When, for example, material contained in first reaction chamber 140 is more highly pressurized relative to material contained in second reaction chamber 120, the pressure differential can help to release or open interface valve 162. Relatedly, such a pressure differential can facilitate mixing between the first material and the second material, as the first material is forcefully expelled from first chamber and into second chamber, thus squirting a stream of first material into a second material contained in the second chamber, where the first material can diffuse into or permeate through the second material. Often, the presence, absence, or extent of any reaction between the first and second materials, or involving either or both of the first and second materials, within the second reaction chamber can be characterized, confirmed, detected, or quantified by inspection, for example with a reader, sensor, or imaging device 190. An imaging device 190 can include a camera, optionally having a charge-coupled device (CCD), that detects or monitors energy that emits from the chamber. In some cases, the imaging device can detect emission intensity output. Exemplary imaging devices and reader techniques suitable for use with embodiments of the present invention are described in U.S. Pat. No. 7,307,802 issued Dec. 11, 2007, the content of which is incorporated herein by reference. In some cases, a reaction within a chamber is facilitated by a thermal cycler. Embodiments of the present invention encompass systems and methods for mixing or reacting materials within chambers, where such mixing or reacting procedures involve any of a variety of desired thermal cycling heating protocols or thermal gradient modalities.

Figure 3:
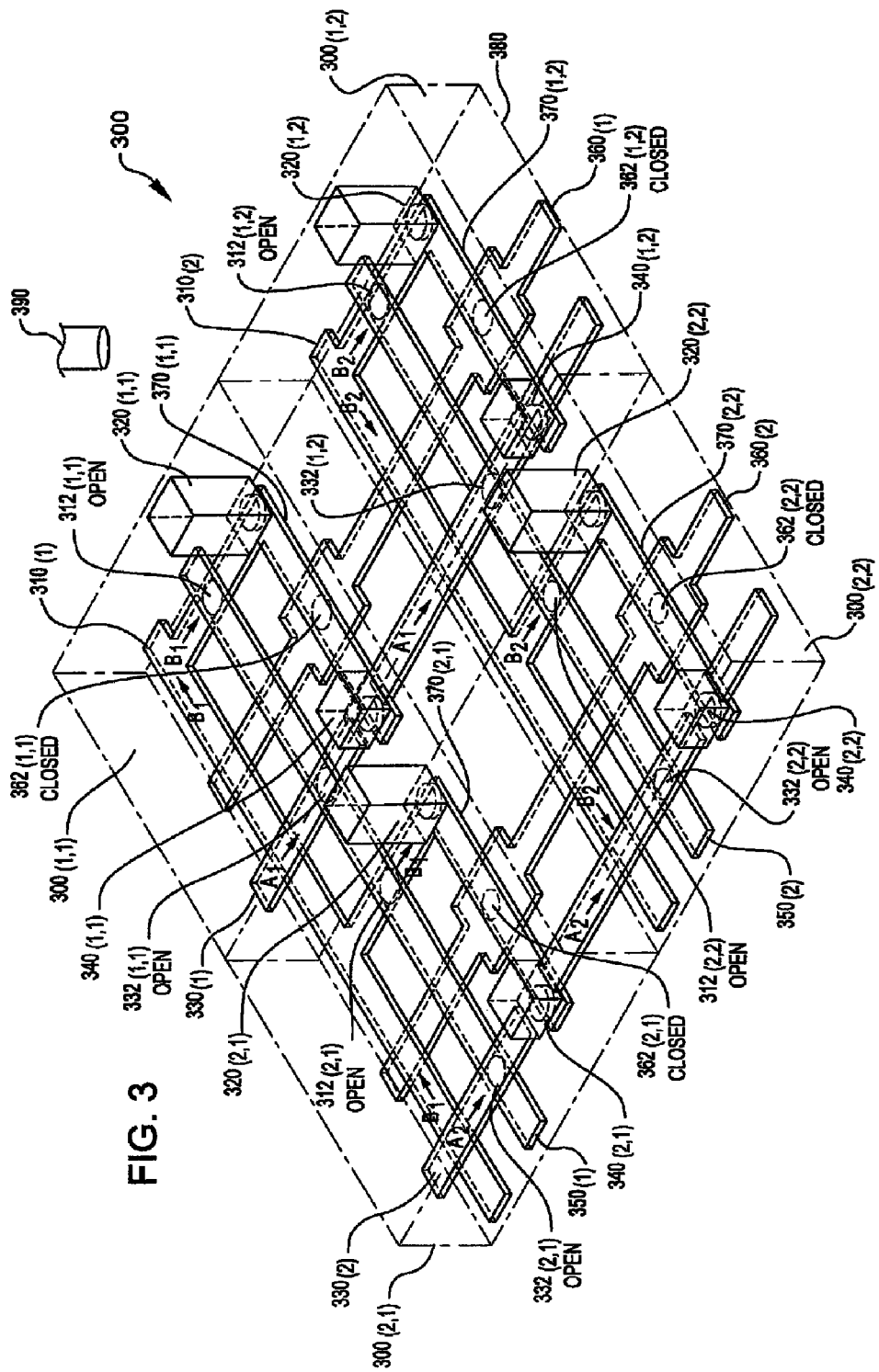
FIG. 3 illustrates a perspective view of a microfluidic device matrix having multiple unit cells according to embodiments of the present invention, showing flow paths for fluid introduction.

FIG. 3 illustrates a perspective view of a matrix 300 having four unit cells $300_{(1,1)}$, $300_{(1,2)}$, $300_{(2,1)}$, and $300_{(2,2)}$ arranged in two rows and two columns. Matrix 300 includes a plurality of first channels $330_{(1)}$, $330_{(2)}$, a plurality of first isolation valves $332_{(1,1)}$, $332_{(1,2)}$, $332_{(2,1)}$, $332_{(2,2)}$, a plurality of first chambers $340_{(1,1)}$, $340_{(1,2)}$, $340_{(2,1)}$, $340_{(2,2)}$, a plurality of second channels $310_{(1)}$, $310_{(2)}$, a plurality of second isolation valves $312_{(1,1)}$, $312_{(1,2)}$, $312_{(2,1)}$, $312_{(2,2)}$, a plurality of second chambers $320_{(1,1)}$, $320_{(1,2)}$, $320_{(2,1)}$, $320_{(2,2)}$, a plurality of control channels $350_{(1)}$, $350_{(2)}$, a plurality of interface channels $360_{(1)}$, $360_{(2)}$, and a plurality of reaction channels $370_{(1,1)}$, $370_{(1,2)}$, $370_{(2,1)}$, $370_{(2,2)}$. It is appreciated that the unit cell architecture embodiments disclosed herein can be scaled to provide a matrix having any number of desired unit cells. For example, a matrix can include 9216 unit cells arranged in 96 rows and 96 columns. Hence, embodiments of the present invention provide a high density format for reacting a plurality of samples with a plurality of reagents, for example, ninety-six (96) samples with ninety-six (96) reagents.

Microfluidic device features such as channels, valves, chambers, are often at least partially contained, embedded, or formed by or within one or more layers of an elastomeric block 380. As shown here with reference to the "A1" arrows, a first material such as a reagent can flow through a first channel $330_{(1)}$, past or through a plurality of first isolation valves $332_{(1,1)}$, $332_{(1,2)}$, and into a plurality of first chambers $340_{(1,1)}$, $340_{(1,2)}$, respectively. Likewise, with reference to the "A2" arrows, a second material such as a reagent can flow through a first channel $330_{(2)}$, past or through a plurality of first isolation valves $332_{(2,1)}$, $332_{(2,2)}$, and into a plurality of first chambers $340_{(2,1)}$, $340_{(2,2)}$, respectively. In some embodiments, materials flow through first channel $330_{(1)}$ and first channel $330_{(2)}$ in the same direction. In some embodiments, material flowing through first channel $330_{(1)}$ travels in a direction opposite from material flowing through first channel $330_{(2)}$. With reference to the "B1" arrows, a third material such as a sample can flow through a second channel $310_{(1)}$, past or through a plurality of second isolation valves $312_{(1,1)}$, $312_{(2,1)}$, and into a plurality of second chambers $320_{(1,1)}$, $320_{(2,1)}$, respectively. Hence, embodiments of the present invention provide microfluidic techniques whereby a material can be flowed through a common passage or trunk of a channel, such as second channel $310_{(1)}$, and into a plurality of individual branches stemming from the common trunk, such as those branch channels which individually feed into second chambers $320_{(1,2)}$, $320_{(2,2)}$. Similarly, with reference to the "B2" arrows, a fourth material such as a sample can flow through a second channel $310_{(2)}$, past or through a plurality of second isolation valves $312_{(1,2)}$, $312_{(2,2)}$, and into a plurality of second chambers $320_{(1,2)}$, $320_{(2,2)}$, respectively. In some embodiments, materials flow through second channel $310_{(1)}$ and second channel $310_{(2)}$ in the same direction. In some embodiments, material flowing through second channel $310_{(1)}$ travels in a direction opposite from material flowing through second channel $310_{(2)}$. As shown in FIG. 3, material flowing through second channel $310_{(1)}$ and material flowing through second channel $310_{(2)}$ travel in opposing directions "B1" and "B2", respectively. Hence, when loading multiple samples into an elastomeric layered block, some samples can be introduced through routing lines on one side of the block, and some samples can be introduced through routing lines on an opposing side of the block. This allows for an even distribution or placement of sample loading route lines on opposite sides of the block, instead of placing all or most sample loading route lines on the same side of the block. Because the sum total of the sample routing lines are divided between different sides of the block, more sample routing lines can be introduced into the block. Consequently, a greater number of samples can be analyzed within the block during a single procedure.

To allow flow from the plurality of first channels $330_{(1)}$, $330_{(2)}$ into the plurality of first reaction chambers $340_{(1,1)}$, $340_{(1,2)}$, $340_{(2,1)}$, $340_{(2,2)}$, each of the plurality of first isolation valves $332_{(1,1)}$, $332_{(1,2)}$, $332_{(2,1)}$, $332_{(2,2)}$ is in an open valve state. To allow flow from the plurality of second channels $310_{(1)}$, $310_{(2)}$ into the plurality of second reaction chambers $320_{(1,1)}$, $320_{(1,2)}$, $320_{(2,1)}$, $320_{(2,2)}$, each of the plurality of second isolation valves $312_{(1,1)}$, $312_{(1,2)}$, $312_{(2,1)}$, $312_{(2,2)}$ is in an open valve state. To prevent or inhibit flow between each of the plurality of first reaction chambers $340_{(1,1)}$, $340_{(1,2)}$, $340_{(2,1)}$, $340_{(2,2)}$ and their corresponding counterpart of the plurality of second reaction chambers $320_{(1,1)}$, $320_{(1,2)}$, $320_{(2,1)}$, $320_{(2,2)}$ through their corresponding counterpart of the plurality of reaction channels $370_{(1,1)}$, $370_{(1,2)}$, $370_{(2,1)}$, $370_{(2,2)}$, respectively, each of the plurality of interface valves $362_{(1,1)}$, $362_{(1,2)}$, $362_{(2,1)}$, $362_{(2,2)}$, respectively, is in a closed valve state. Under such conditions, first channel $330_{(1)}$ is in fluid communication with first reaction chambers $340_{(1,1)}$, $340_{(1,2)}$, first channel $330_{(2)}$ is in fluid communication with first reaction chambers $340_{(2,1)}$, $340_{(2,2)}$, second channel $310_{(1)}$ is in fluid communication with second reaction chambers $320_{(1,1)}$, $320_{(2,1)}$, and second channel $310_{(2)}$ is in fluid communication with second reaction chambers $320_{(1,2)}$, $320_{(2,2)}$. Fluid communication between first chambers $340_{(1,1)}$, $340_{(1,2)}$, $340_{(2,1)}$, $340_{(2,2)}$ and second chambers $320_{(1,1)}$, $320_{(1,2)}$, $320_{(2,1)}$, $320_{(2,2)}$, respectively, is interrupted.

A first material can be loaded into first reaction chambers $340_{(1,1)}$, $340_{(1,2)}$ via first channel $330_{(1)}$. A second material can be loaded into first reaction chambers $340_{(2,1)}$, $340_{(2,2)}$ via first channel $330_{(2)}$. A third material can be loaded into second reaction chambers $320_{(1,1)}$, $320_{(2,1)}$ via second channel $310_{(1)}$. A fourth material can be loaded into second reaction chambers $320_{(1,2)}$, $320_{(2,2)}$ via second channel $310_{(2)}$. Optionally, such materials can be loaded into the chambers under a desired or selected pressure. Control channel $350_{(1)}$ can be activated so as to transform each of first isolation valves $332_{(1,1)}$, $332_{(2,1)}$ and second isolation valves $312_{(1,1)}$, $312_{(2,1)}$ from an open valve state to a closed valve state. Similarly, control channel $350_{(2)}$ can be activated so as to transform each of first isolation valves $332_{(1,2)}$, $332_{(2,2)}$ and second isolation valves $312_{(1,2)}$, $312_{(2,2)}$ from an open valve state to a closed valve state. In this way the materials can be confined or maintained, optionally under pressure, within the reaction chambers.

Figure 4:
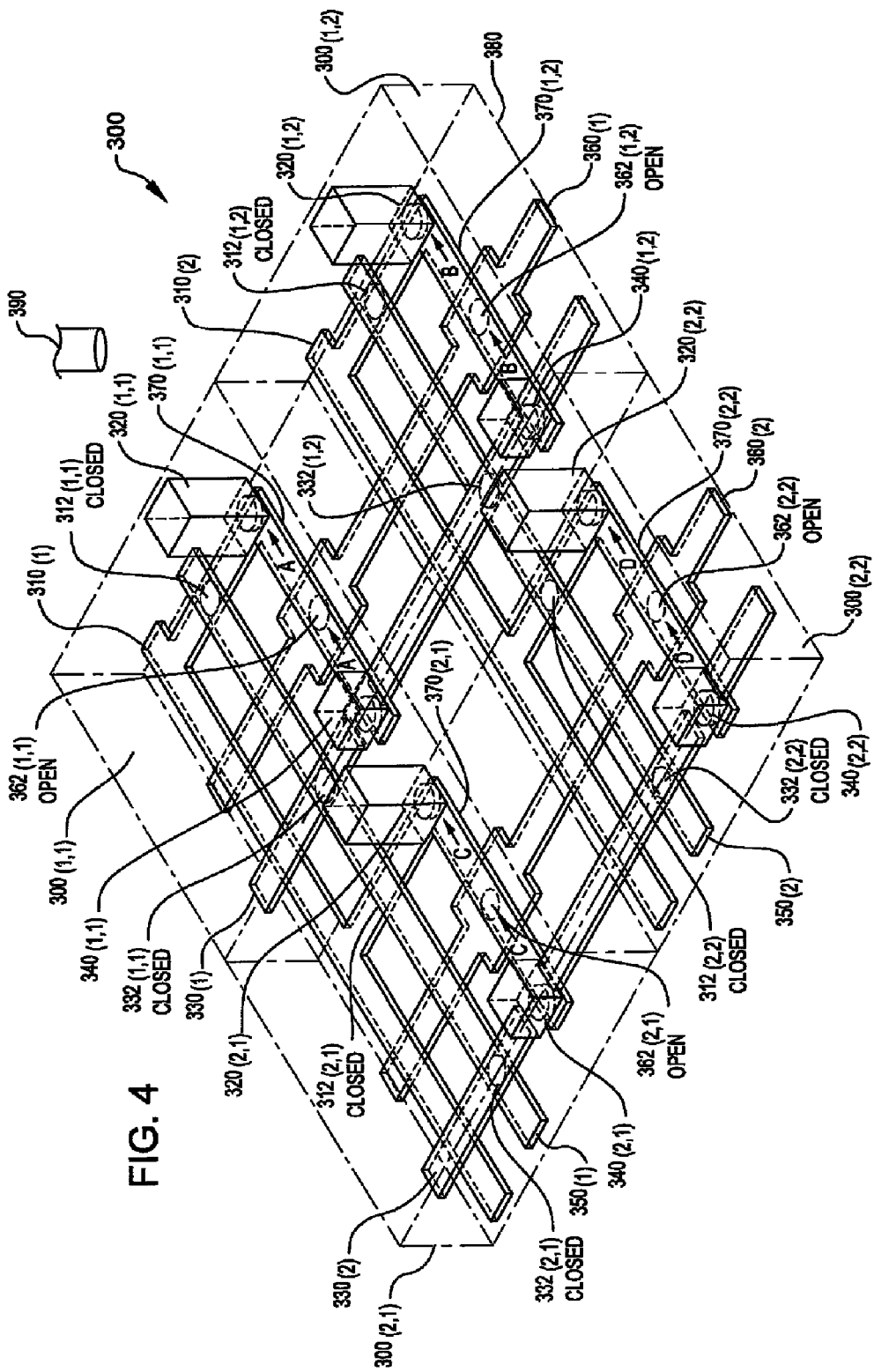
FIG. 4 illustrates a perspective view of the microfluidic device matrix of FIG. 3, showing flow paths for fluid mixing.

FIG. 4 illustrates another perspective view of matrix 300 having four unit cells $300_{(1,1)}$, $300_{(1,2)}$, $300_{(2,1)}$, $300_{(2,2)}$. As shown here with reference to the "A" arrows, the first material can flow from first reaction chamber $340_{(1,1)}$, through reaction channel $370_{(1,1)}$, past interface valve $362_{(1,1)}$, and into second reaction chamber $320_{(1,1)}$, where the first material can contact the third material. To allow such flow through reaction channel $370_{(1,1)}$, the interface channel $360_{(1)}$ can be activated so as to transform interface valve $362_{(1,1)}$ from a closed valve state to an open valve state. Under such conditions, first reaction chamber $340_{(1,1)}$ and second reaction chamber $320_{(1,1)}$ are in fluid communication via reaction channel $370_{(1,1)}$. Often, the presence, absence, or extent of any reaction between the first and third materials within second reaction chamber $320_{(1,1)}$ can be confirmed, detected, or quantified by inspection, for example with a reader or sensor 390.

With reference to the "B" arrows, the first material can flow from first reaction chamber $340_{(1,2)}$, through reaction channel $370_{(1,2)}$, past interface valve $362_{(1,2)}$, and into second reaction chamber $320_{(1,2)}$, where the first material can contact the fourth material. To allow such flow through reaction channel $370_{(1,2)}$, the interface channel $360_{(1)}$ can be activated so as to transform interface valve $362_{(1,2)}$ from a closed valve state to an open valve state. Under such conditions, first reaction chamber $340_{(1,2)}$ and second reaction chamber $320_{(1,2)}$ are in fluid communication via reaction channel $370_{(1,2)}$. Often, the presence, absence, or extent of any reaction between the first and third materials within second reaction chamber $340_{(1,2)}$ can be confirmed, detected, or quantified by inspection, for example with a reader or sensor 390.

With reference to the "C" arrows, the second material can flow from first reaction chamber $340_{(2,1)}$, through reaction channel $370_{(2,1)}$, past interface valve $362_{(2,1)}$, and into second reaction chamber $320_{(2,1)}$, where the second material can contact the third material. To allow such flow through reaction channel $370_{(2,1)}$, the interface channel $360_{(2)}$ can be activated so as to transform interface valve $362_{(2,1)}$ from a closed valve state to an open valve state. Under such conditions, first reaction chamber $340_{(2,1)}$ and second reaction chamber $320_{(2,1)}$ are in fluid communication via reaction channel $370_{(2,1)}$. Often, the presence, absence, or extent of any reaction between the first and third materials within second reaction chamber $320_{(2,1)}$ can be confirmed, detected, or quantified by inspection, for example with a reader or sensor 390.

With reference to the "D" arrows, the second material can flow from first reaction chamber $340_{(2,2)}$, through reaction channel $370_{(2,2)}$, past interface valve $362_{(2,2)}$, and into second reaction chamber $320_{(2,2)}$, where the second material can contact the fourth material. To allow such flow through reaction channel $370_{(2,2)}$, the interface channel $360_{(2)}$ can be activated so as to transform interface valve $362_{(2,2)}$ from a closed valve state to an open valve state. Under such conditions, first reaction chamber $340_{(2,2)}$ and second reaction chamber $320_{(2,2)}$ are in fluid communication via reaction channel $370_{(2,2)}$. Often, the presence, absence, or extent of any reaction between the fourth and second materials within second reaction chamber $320_{(2,2)}$ can be confirmed, detected, or quantified by inspection, for example with a reader or sensor 390.

Figure 5A:
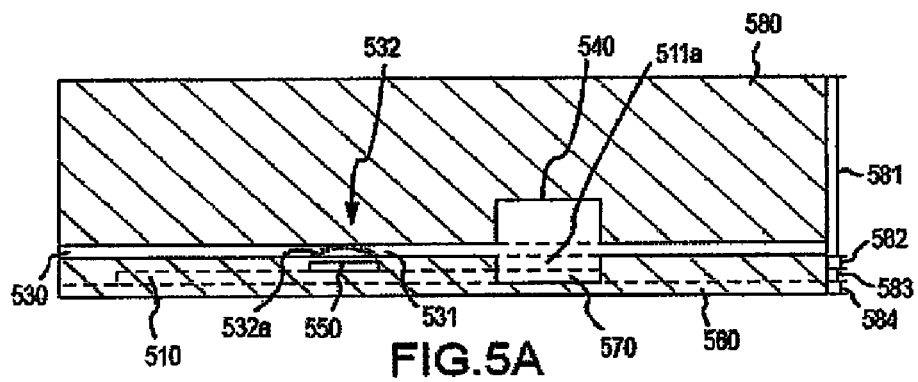
FIGS. 5A to 5C show cross-section views of a microfluidic device unit cell according to embodiments of the present invention.
Figure 5B:
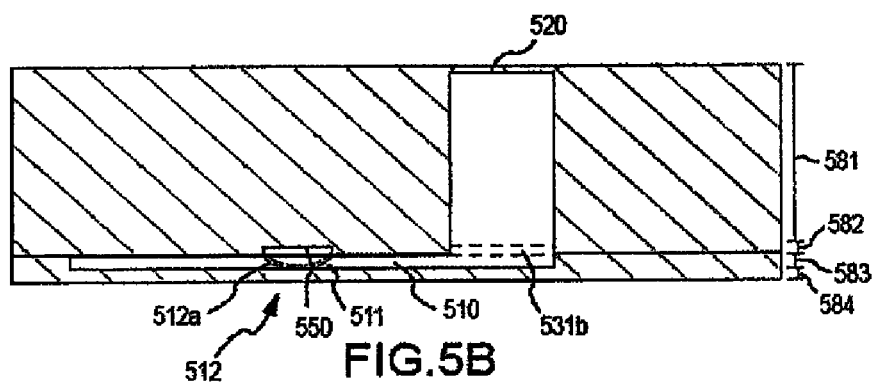
Figure 5C:
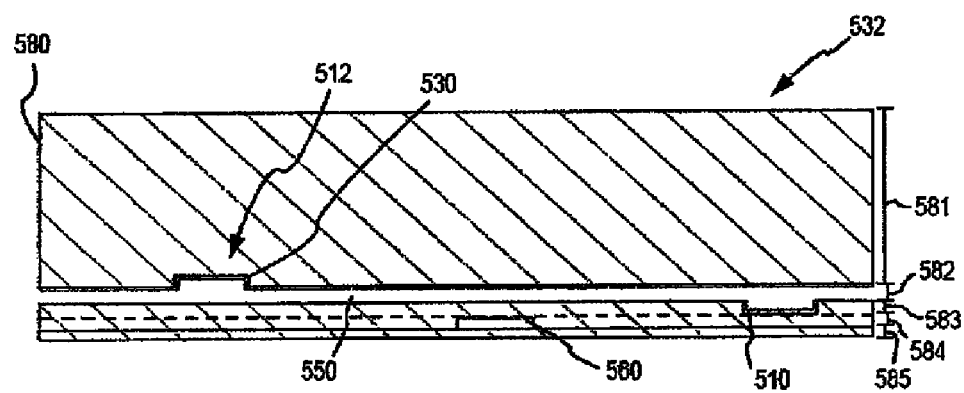

In some embodiments, the terms "isolation valve" and "containment valve" may be used interchangeably. Similarly, the terms "interface valve" and "reaction valve" may be used interchangeably. Such valves can be actuated or activated or otherwise controlled by any of a variety of valve operation methods or configurations. Exemplary valve systems and techniques which are well suited for use with embodiments of the present invention are described, for example, in U.S. Pat. No. 6,408,878, the content of which is incorporated herein by reference. Often, such valves include an elastomeric portion that, when actuated, deflects into a recess. For example, FIG. 5A shows a side view or cross section of a microfluidic device unit cell 500. The unit cell includes a first channel 530 and first sample chamber 540 in a first layer 581 of an elastomeric block 580, control channel 550 and via 511a in a second layer 582, and a reaction channel 570 in a third layer 583. An isolation valve 532 can be actuated, so as to inhibit or prevent flow through first channel 530. Actuation of isolation valve 532 can involve the deflection of an elastomeric portion 532a into a recess 531 of first channel 530. Fourth layer 584 includes interface channel 560. FIG. 5B shows another side view or cross section of microfluidic device unit cell 500. The unit cell includes a sample chamber 520 in a first layer 581, a control channel 550 and via 531b in a second layer 582, and a second channel 510 in a third layer 583. Isolation valve 512 can be actuated, so as to inhibit or prevent flow through second channel 510. Actuation of isolation valve 512 can involve the deflection of an elastomeric portion 512a into a recess 511 of second channel 510. FIG. 5C shows a side view or cross section which is orthogonal to the side views of FIGS. 5A and 5B. As depicted here, actuation of control channel 550 can operate to activate both isolation valve 532 and isolation valve 512. For example, by changing the pressure of fluid within control channel or containment line 550, it is possible to simultaneously deflect a first elastomeric portion upward into first channel 530 and a second elastomeric portion downward into second channel 510. Optionally this can result in the containment or isolation of a first material within a first chamber and a second material within a second chamber.

As shown in FIG. 5C, first channel 530 and second channel 510 each present a rectangular cross section. In some instances, either or both of these channels can present an arcuate shaped cross section, where the cross section is upright with regard to first channel 530 and inverted with regard to second channel 510.

Figure 6A:
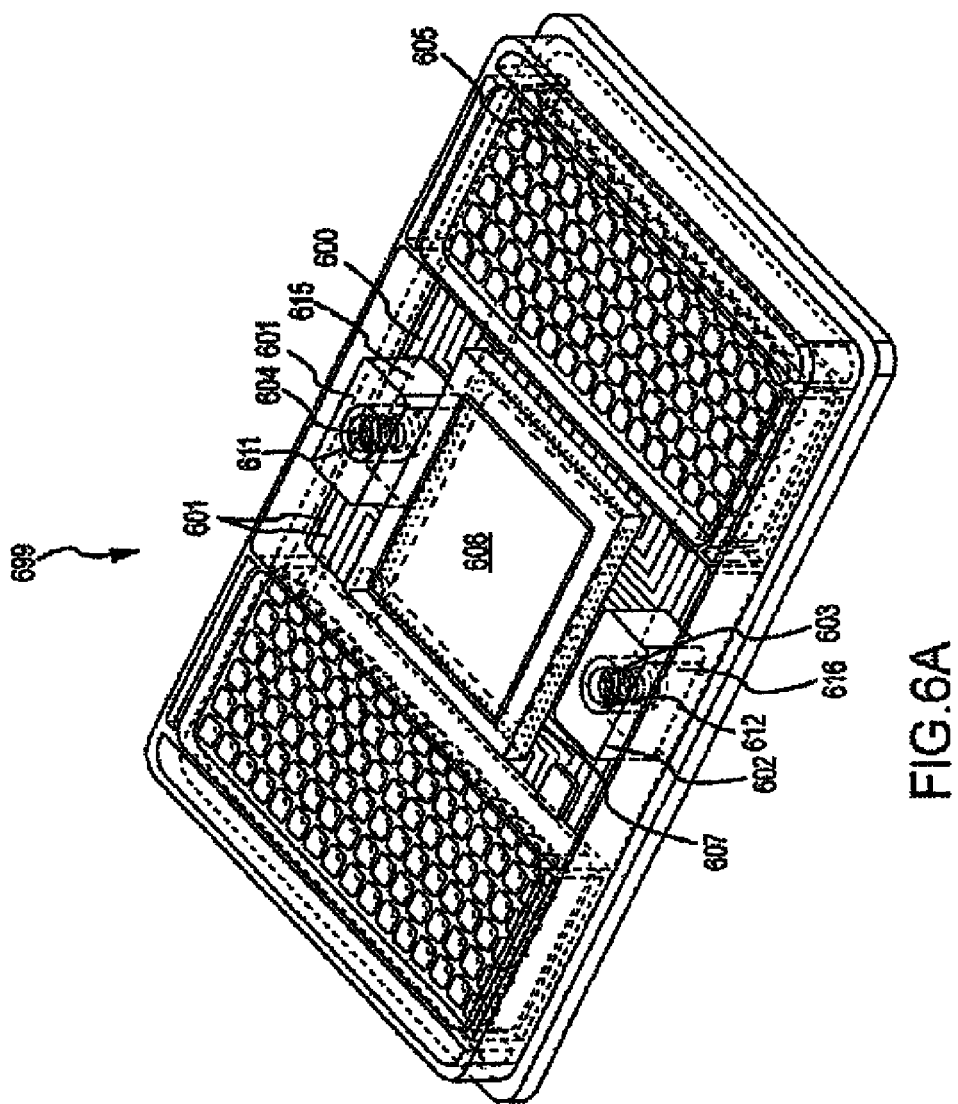
FIGS. 6A to 6C show a microfluidic device according to embodiments of the present invention.
Figure 6B:
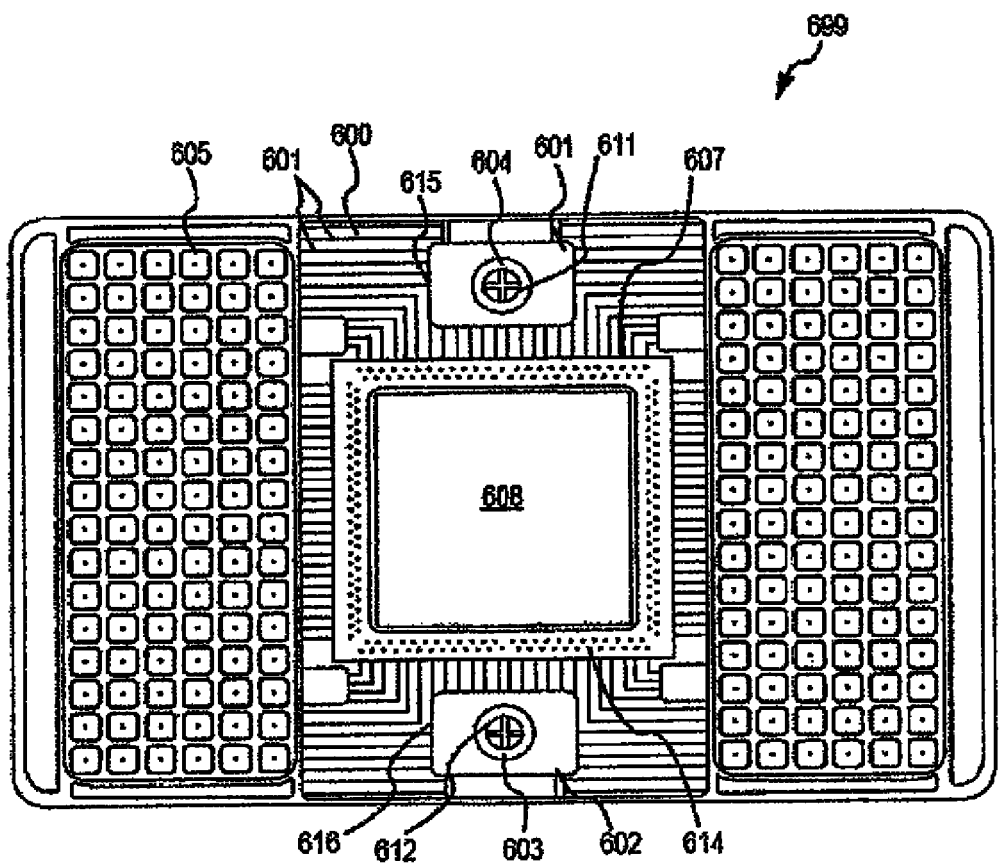

FIG. 6A illustrates a microfluidic device 699 according to embodiments of the present invention. Materials can be delivered from wells 605 toward elastomeric block 608 through passages or routing lines 601. FIG. 6B depicts microfluidic device 699 in a plan view. Microfluidic device 699 includes a substrate 600 with integrated pressure accumulator wells 601 and 602, each having a receptacle 603, 604 that contains a valve, such as a check valve. Microfluidic device 699 also includes one or more wells 605 for receiving materials such as samples or reagents, and one or more channels or routing lines disposed between wells 605 and an elastomeric block location 607 of substrate 600. An elastomeric block 608 can be coupled with substrate 600 at elastomeric block location 607. Elastomeric block 608 can include one or more layers of elastomeric material having microfabricated recesses or channels formed therein. Elastomeric block 608 can be coupled with substrate 600 in any of a variety of ways. For example, the elastomeric block can be attached or bonded with the substrate. In some cases, the block is directly bonded to the substrate. In some cases, the block is coupled with the substrate without the use of an adhesive. In some cases, the block is coupled with the substrate with an adhesive. Within elastomeric block 608 are one or more channels in fluid communication with one or more vias 614, which in turn provide fluid communication between the elastomeric block channels and the substrate channels. Hence, the substrate channels can provide fluid communication between wells 605 and channels within the elastomeric block.

Accumulator wells 601, 602 often include valves 611, 612, respectively, which can be check valves for introducing and holding gas of fluid under pressure into accumulator chambers 615 and 616. Valves 611 and 612 are situated inside of receptacles 604 and 603, respectively, which can keep liquid, when present in accumulator chambers 615 and 616, from contacting valves 611 and 612. In some embodiments, valves 611 and 612 may be mechanically opened by pressing a shave, pin or the like, within a check valve to overcome a self closing force of the check valve, thereby permitting release of pressure from the accumulator chamber, or reducing fluid pressure contained within the accumulator chamber.

Figure 6C:
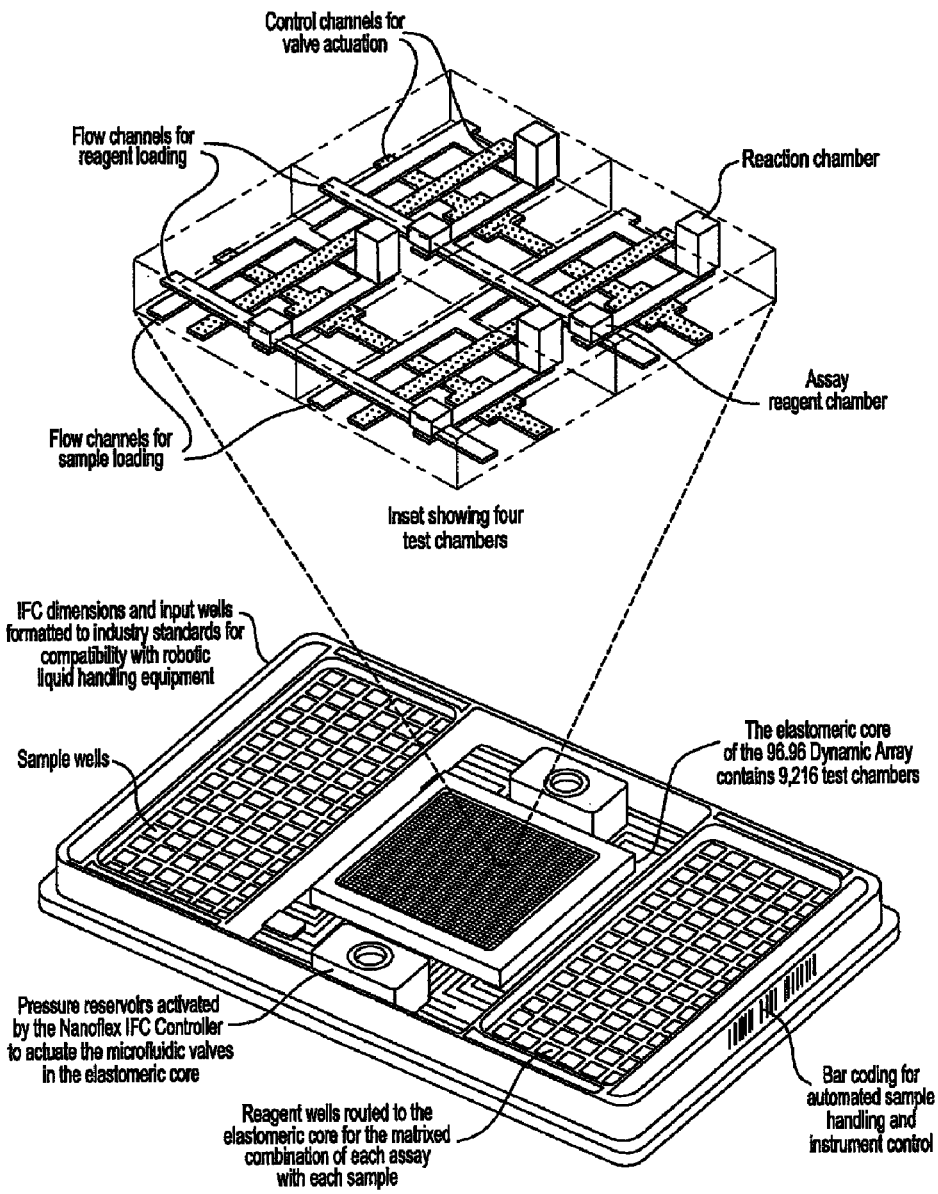

Substrate 600 and associated components may be fabricated from polymers, such as polypropylene, polyethylene, polycarbonate, high-density polyethylene, polytetrafluoroethylene PTFE or Teflon®, glass, quartz, transparent materials, polysilicon, metals, such as aluminum, or the like. Any of a variety of gases, liquids, or fluids can be introduced into accumulator chambers 615 and 616. In some cases, valves 611 and 612 can be actuated to release fluid pressure otherwise held inside of accumulator chambers 615 and 616. Optionally, a portion of substrate 600 beneath the elastomeric block region 607 can be transparent. In some cases, the portion may be opaque or reflective. Accumulator chambers 601 and 602 can be in fluid communication with channels contained in elastomeric block region 607, and ultimately, with channels contained in elastomeric block 608. Accumulator operation is described in U.S. Patent Publication No. 2007/0196912, the content of which is incorporated herein by reference. In some cases, operation of a channel, such as a control channel 150 as shown in FIG. 1, can be modulated or controlled by an accumulator. FIG. 6C illustrates further aspects of a microfluidic device in accordance with embodiments of the present invention.

Figure 7:
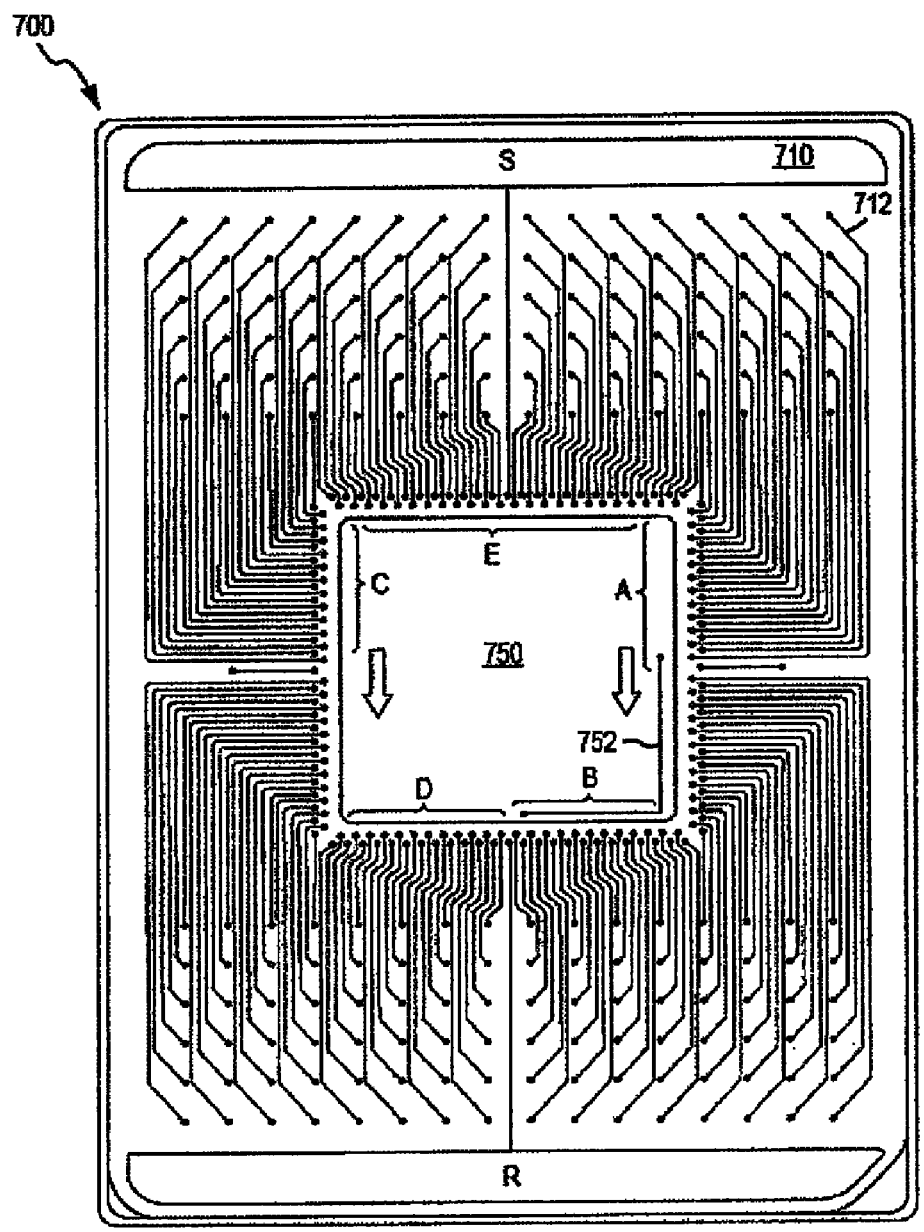
FIG. 7 illustrates a microfluidic device according to embodiments of the present invention.

FIG. 7 illustrates a microfluidic device 700 according to embodiments of the present invention. Device 700 includes a carrier 710 coupled with a chip or block 750. Carrier or frame 710 includes a plurality of routing lines 712 configured to allow flow from carrier wells (see wells 605 in FIG. 6B) toward chip 750. For example, routing lines disposed on the "S" side of the carrier can provide for the passage of sample, and routing lines disposed on the "R" side of the carrier can provide for the passage of reagent. In some cases, chip 750 can also include a plurality of routing lines 752. For example, routing lines 752 on the chip 750 can provide material transport on the chip from location A to location B, and from location C to location D. In this way, a portion of the samples loaded onto the carrier 710 can be transported to location E of the chip, and another portion of the samples loaded onto the carrier can be transported to locations D and B of the chip, such that some sample is loaded at one side of the block, and some sample is loaded at an opposing side of the block, as discussed above with reference to FIG. 3.

Figure 8:
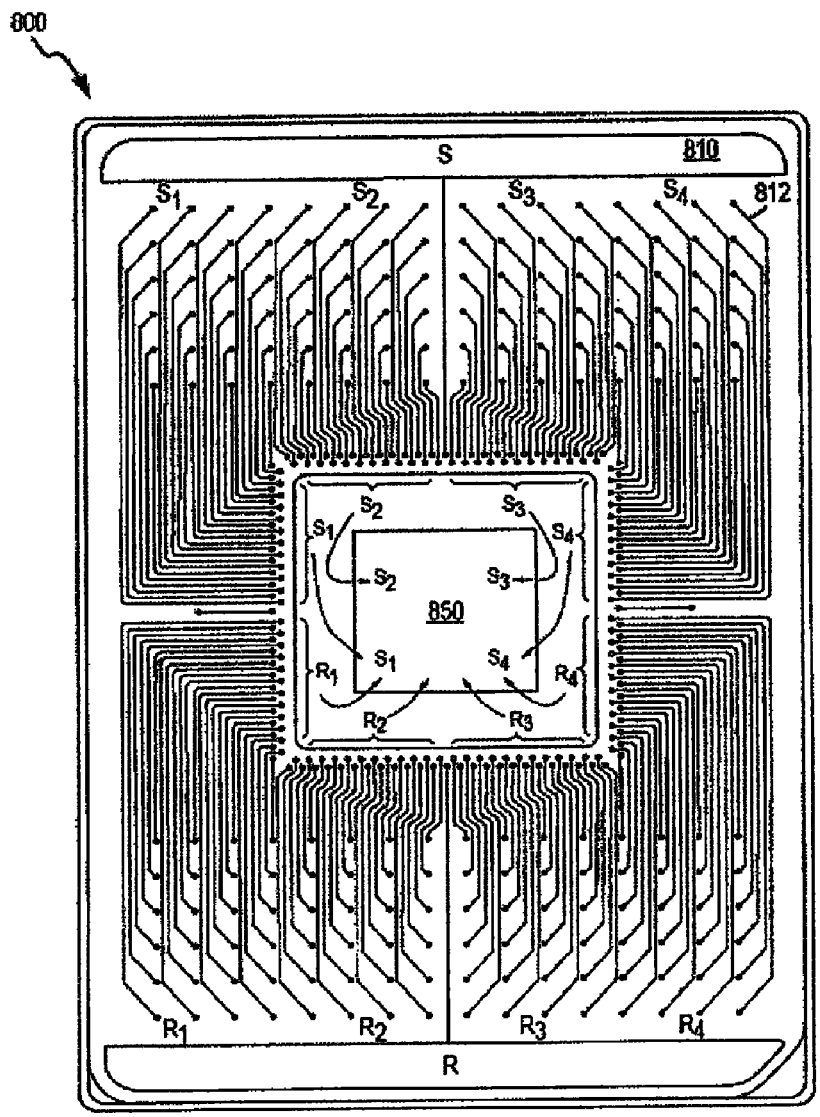
FIG. 8 illustrates a microfluidic device according to embodiments of the present invention.

FIG. 8 illustrates a microfluidic device 800 according to embodiments of the present invention. Device 800 includes a carrier 810 coupled with a chip or block 850. Carrier or frame 810 includes a plurality of routing lines 812 configured to allow flow from carrier wells toward chip 850. For example, routing lines disposed on the "S" side of the carrier can provide for the passage of sample, and routing lines disposed on the "R" side of the carrier can provide for the passage of reagent. As shown in this illustration, 24 samples loaded into wells at zone $S_1$ flow to the left side of the chip (upper half), 24 samples loaded into wells at zone $S_2$ flow to the upper side of the chip (left half), 24 samples loaded into wells at zone $S_3$ flow to the upper side of the chip (right half), and 24 samples loaded into wells at zone $S_4$ flow to the right side of the chip (upper half). Thereafter, through a set of routing lines optionally disposed at or within the elastomeric block, the $S_1$ samples flow to the left side of the chip (lower half) as shown by the arrows, the $S_2$ samples flow to the left side of the chip (upper half), the $S_3$ samples flow to the right side of the chip (upper half), and the $S_4$ samples flow to the right side of the chip (lower half). Further, 24 reagent portions loaded into wells at zone $R_1$ flow to the left side of the chip (lower half), 24 reagent portions loaded into wells at zone $R_2$ flow to the lower side of the chip (left half), 24 reagent portions loaded into wells at zone $R_3$ flow to the lower side of the chip (right half), and 24 reagent portions loaded into wells at zone $R_4$ flow to the right side of the chip (lower half). Thereafter, through another set of routing lines optionally disposed at or within the elastomeric block, the $R_1$ reagent portions flow to the lower side of the chip (left half), the $R_2$ reagent portions flow to the lower side of the chip (left half), the $R_3$ reagent portions flow to the lower side of the chip (right half), and the $R_4$ samples flow to the lower side of the chip (right half). Hence, routing lines on or in the chip can provide material transport on or through the chip from one location to another. In this way, a portion of the samples loaded at one end of the carrier (e.g., the "S" end) can be transported such that some sample is loaded at one side of the block, and some sample is loaded at an opposing side of the block, as further discussed herein with reference to FIG. 3.

In some embodiments, microfluidic devices may contain blind flow channels which include a region that functions as a reaction chamber or reaction site. Blind flow, or blind fill, can refer to the filling of a dead-end tube or flow channel with a liquid where a head of gas is pushed in front of the liquid bolus, and where that head of gas is vented or otherwise released from the flow channel, allowing the dead-end flow channel to fill fully with the liquid. In some embodiments, polydimethylsiloxane (PDMS) can be used as an elastomeric material. PDMS is sufficiently gas permeable that liquid pressurized at a few psi can drive the gas out of the channels, leaving them completely filled with liquid.

Table 1 provides an exemplary use of a microfluidic device where various materials can be loaded or introduced into four unit cells of the device. According to this table, sample can be flowed through first channels and reagent can be flowed through second channels. It is understood that alternatively, reagent can be flowed through first channels and sample can be flowed through second channels. Embodiments of the present invention encompass techniques where sample is flowed through a set of first channels and a set of second channels, and reagent is flowed through a set of first channels and a set of second channels.

TABLE 1

| channel | material | chamber |
| --- | --- | --- |
| first channel $330_{(1)}$ | DNA sample from person A | first chambers $340_{(1,1)}, 340_{(1,2)}$ |
| first channel $330_{(2)}$ | DNA sample from person B | first chambers $340_{(2,1)}, 340_{(2,2)}$ |
| second channel $310_{(1)}$ | disease X gene primers/probes | second chambers $320_{(1,1)}, 320_{(2,1)}$ |
| second channel $310_{(2)}$ | disease Y gene primers/probes | second chambers $320_{(1,2)}, 320_{(2,2)}$ |

Table 2 shows the mixtures occurring in the microfluidic device reaction chambers, and the experimental inquiries which can be answered, for example, by conducting a PCR reaction where the sample contains patient DNA and the reagent contains an oligonucleotide primer and probe set.

TABLE 2

| reaction chamber | materials mixed | inquiry |
|---|---|---|
| second chamber $320_{(1,1)}$ | DNA sample from person A disease X gene primer/probe | person A has gene for disease X? |
| second chamber $320_{(1,2)}$ | DNA sample from person A disease Y gene primer/probe | person A has gene for disease Y? |
| second chamber $320_{(2,1)}$ | DNA sample from person B disease X gene primer/probe | person B has gene for disease X? |
| second chamber $320_{(2,2)}$ | DNA sample from person B disease Y gene primer/probe | person B has gene for disease Y? |

It is understood that any of a variety of materials may be mixed or reacted in according to embodiments of the present invention. For example, genotyping applications may involve detecting the presence or absence of a target in a sample. Gene expression applications may involve measuring or quantifying amounts of materials contained in a sample. Such applications may benefit from the enhanced mixing function provided by embodiments of the present invention. Further, microfluidic devices and methods can be used to crystallize a protein. In one embodiment a method includes providing a microfluidic device having a first chamber having a dimension between 1000 μM and 1 μm, a second chamber having a dimension between 1000 μm and 1 μm, and one or more flow or control channels each having a dimension between 1000 μm and 1 μm. The first and second chambers can be in fluid communication with each other through a channel. A valve can be disposed along a channel which, when actuated to open or close, controls fluid communication between the first and second chambers, or into or out of the first or second chamber, or both. The method can include introducing a crystallization reagent into the first chamber, introducing the protein in a solution into the second chamber, opening a valve so that the solution containing the protein in the second chamber becomes in fluid communication with the crystallization reagent in the first chamber, and closing the valve after a period of time to interrupt fluid communication between the first and second chambers.

In some embodiments, a valve can be under the control of an automated valve actuating device, which in turn may be further under control of a computer or processor. A multilayer microfluidic device can include at least one elastomeric layer, and a valve can include a deflectable membrane. In some cases, a deflectable membrane of a valve can be deflectable into one or more channels to control fluid movement along the channels. Multiple elastomeric membranes may be bonded or adhered together to form an elastomeric block. In some cases, portions of channels or chambers can overlap with portions of other channels or chambers at an overlap region. Such channels or chambers can be in fluid communication through a via located at the overlap region.

Reduced Mixing Times

Figure 9A:
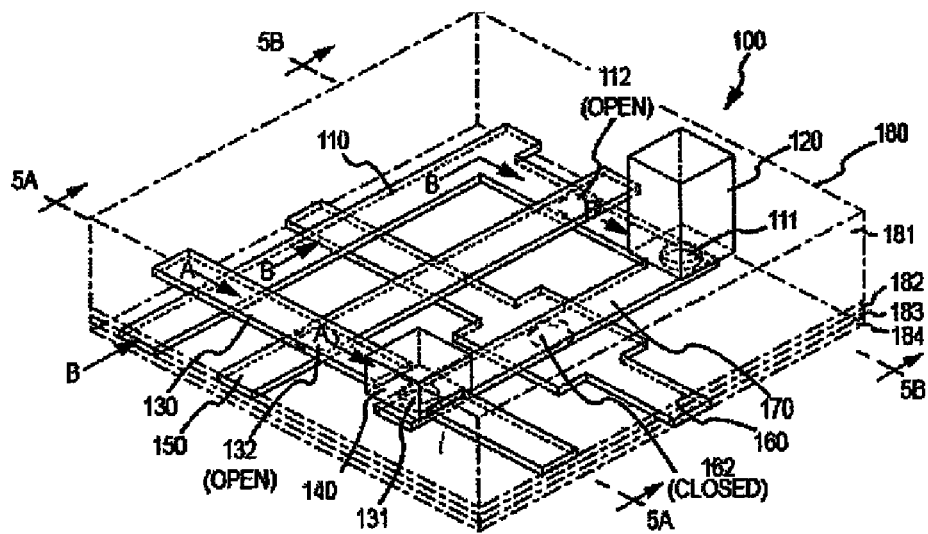
FIGS. 9A and 9B illustrate a microfluidic device according to embodiments of the present invention.

Embodiments of the present invention providing methods for reducing microfluidic device mixing times will now be described with reference to FIGS. 9A and 9B. FIG. 9A shows the unit cell 100 of FIG. 1. As discussed above with reference to FIG. 1, a first material, such as an assay reagent, can be introduced into first chamber 140 past open first isolation valve 132. Similarly, a second material, such as an assay sample, can be introduced into second chamber 120 past open second isolation valve 112. The first and second materials can be introduced under pressure. Once the first and second materials have been introduced, the first isolation valve 132 and the second isolation valve 112 can be closed via activation of control channel 150. In some embodiments, the first material is disposed within first chamber 140 at a first pressure and the second material is disposed within second chamber 120 at a second pressure. During introduction of the first material and the second material, interface valve 162 can be in the closed position so as to isolate the first material from the second material.

Figure 9B:
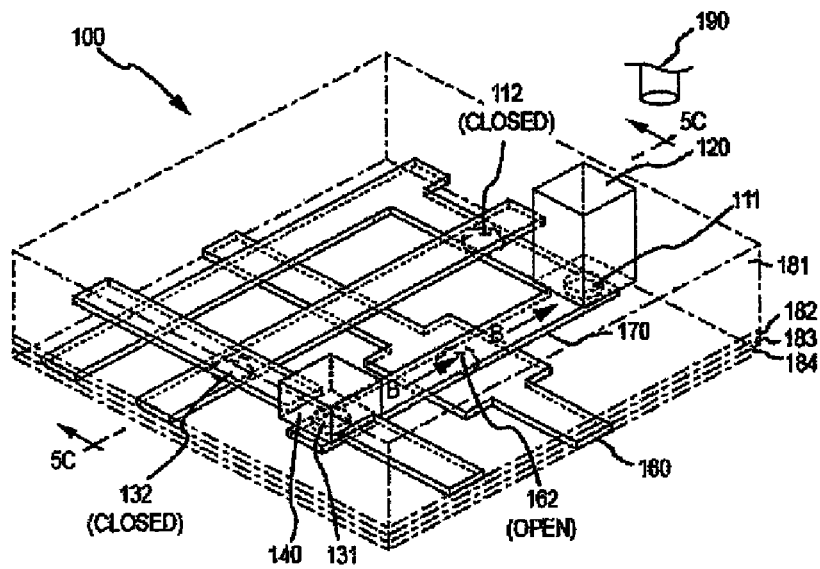

FIG. 9B shows the unit cell 100 of FIG. 2. As discussed above with reference to FIG. 2, the first material disposed within first chamber 140 can be mixed with the second material in second chamber 120 by opening interface valve 162. In instances where little to no pressure differential exists between the first material disposed in the first chamber 140 and the second material disposed in the second chamber 120, opening interface valve 162 will typically result in mixing by diffusion. Mixing by diffusion typically takes a significantly greater amount of time relative to the time required for some non-diffusion types of mixing.

In embodiments of the present invention, the first and second materials are introduced so as to be disposed within their respective chambers at pressure levels that are sufficiently different so that when interface valve 162 is opened, mixing between the first material and the second material occurs at least in part by fluid injection. For example, the first and second materials can be introduced so that the first material is disposed within first chamber 140 at a first pressure that is higher than a second pressure at which the second material is disposed within second chamber 120. Where this pressure differential is sufficiently different, opening interface valve 162 will result in some of the first material being injected into the second material. Preferably, the pressure differential will be sufficiently different such that some of the first material will be injected into second chamber 120. Although various pressure differentials can be used, it may be advantageous to use a pressure differential of 1 psi or greater.

The extent to which mixing occurs due to fluid injection may vary due to a number of factors, such as the materials involved, the pressure differential involved, and the characteristics of the microfluidic device involved. Less viscous materials may result in higher levels of mixing by injection than more viscous materials. Greater pressure differentials will typically result in higher levels of mixing by injection than lower pressure differentials. Microfluidic device characteristics, such as chamber volume, chamber compliance, and channel impedance, can also influence the amount of mixing that occurs by injection. When interface valve 162 is opened, material will flow from the higher pressure chamber towards the lower pressure chamber until equilibrium is reached. Larger and more compliant chambers may result in greater amounts of material flow for a given pressure differential. Chamber volume differentials can be used to vary the relationship between the two chamber pressures and the resulting equilibrium pressure. For example, where first chamber 140 is smaller than second chamber 120, the resulting equilibrium pressure may be closer to the pressure within second chamber 120 prior to opening interface valve 162 than to the pressure within first chamber 140 prior to opening interface valve 162. Greater amounts of pressure difference between a high pressure chamber and the equilibrium pressure may result in greater resulting amounts of material flow.

Increased Manufacturing Yield Rates

Embodiments of the present invention providing microfluidic devices with increased manufacturing yield rates, and related methods of manufacture, will now be described with reference to FIGS. 10A and 10B. A device can include, for example, a configuration that allows for the isolation of defective portions of a microfluidic device. During manufacture of a microfluidic device, manufacturing defects may result in one or more defective portions of a microfluidic device. A defect may render one or more fluid paths associated with a defective portion sufficiently non-functional as a result. For example, a defect may result in a sample channel or a reagent channel being rendered sufficiently non-functional due to their association with the defective portion of the microfluidic device. Embodiments of the present invention provide microfluidic devices that can be configured so as to isolate these defects.

Often, defects can be identified and located during quality control inspection(s). Such defects can include dysfunctional valves that may exist due to various causes (e.g., the presence of particles, mold defects, etc.). A microfluidic device can be non-destructively tested by filling the device with an inert volatile material (e.g., FC72 made by the 3M Corporation) and performing a microscopic inspection for defects. For example, the microscopic inspection can detect flows of the inert material indicative of failures (e.g., a flow indicative of a failed valve such as a containment valve, etc.). Based on the microscopic inspection, the defect can often be located.

FIG. 10A diagrammatically illustrates a microfluidic array device that provides an ability to isolate defects. FIG. 10A shows a pre-quality control configuration that has not yet been configured to isolate any particular defect. Microfluidic array device 400 includes a plurality of reagent inlets 402 and a plurality of sample inlets 404. Each of the reagent inlets 402 is in initial fluid communication with a unique pair of reagent flow channels 406. Likewise, each of the sample inlets 404 is in initial fluid communication with a unique pair of sample flow channels 408. Each of the reagent flow channels 406 is for the introduction of a reagent fluid into one or more reaction cells. Likewise, each sample flow channel 408 is for the introduction of a sample fluid into one or more reaction cells. While each reagent inlet 402 is shown in initial fluid communication with a unique pair of reagent flow channels 406, it should be appreciated that any particular reagent inlet 402 may be in initial fluid communication with any number of reagent flow channels 406, such as one, two, or more. The same applies for each sample inlet 404, which may be in initial fluid communication with any number of sample flow channels 408, such as one, two, or more.

FIG. 10B diagrammatically illustrates a portion of the microfluidic array device 400 of FIG. 10A. FIG. 10B shows a post-quality control configuration that has been configured to isolate a defect 414. Microfluidic array device 400 includes fusible isolation features by which individual reagent flow channels 406 and individual sample flow channels 408 can be selectively fluidically closed, thereby isolating their associated inlet from their associated one or more reaction cells. A fusible isolation feature can be provided by a containment valve 412 located under each of the reagent flow channels 406 and under each of the sample flow channels 408. All of the containment valves 412 can be actuated by one or more control channels 410. Once a containment valve 412 selected for fusing has been closed using its control channel 410, an exposure to a low frequency ultraviolet light can be used to cause the exposed containment valve 412 to fuse and remain closed once the control channel 410 pressure is released. This selective fusing of containment valves 412 allows for a selective approach in determining which reagent flow channels 406 and which sample flow channels 408 remain active. It should be appreciated that a variety of different approaches can be used to selectively determine which reagent flow channels and which sample flow channels are active. For example, each flow channel may be initially fluidically closed, and may be selectively opened, such as by removing material so as to open the flow channel.

The ability to selectively choose which of two flow channels will be connected with a particular inlet provides the ability to isolate the inlet from a defective flow channel, while still having the inlet connected with a functional flow channel. For example, a defective flow channel can be isolated from two associated inlets, while the two associated inlets can themselves be connected with adjacent functional channels. By creating a design with built in redundancy, the manufacturing yield rate can be significantly improved. For example, a microfluidic array device 400 that includes 48 reagent inlets 402 and 48 sample inlets 404 that are collectively in initial fluid communication with 50 reagent flow channels 406 and 50 sample flow channels 408 respectively can tolerate up to two reagent flow channels 406 and two sample flow channels 408 that cannot be used due to identified defects and still maintain a functioning 48 by 48 microfluidic device array 400.

Supplying Controlled Pressure

Embodiments of the present invention providing apparatus and systems for supplying controlled pressure to a microfluidic device will now be described with reference to FIGS. 11A, 11B, 11C, and 11D. Microfluidic device processing equipment is often used to supply pressurized fluids to a microfluidic device. For example, these fluids can include one or more sample fluids, one or more reagent fluids, and one or more control fluids. In certain instances, it may be desirable to use multiple pressure levels, such as greater than eight pressure levels, with any particular microfluidic device.

Figure 11A:
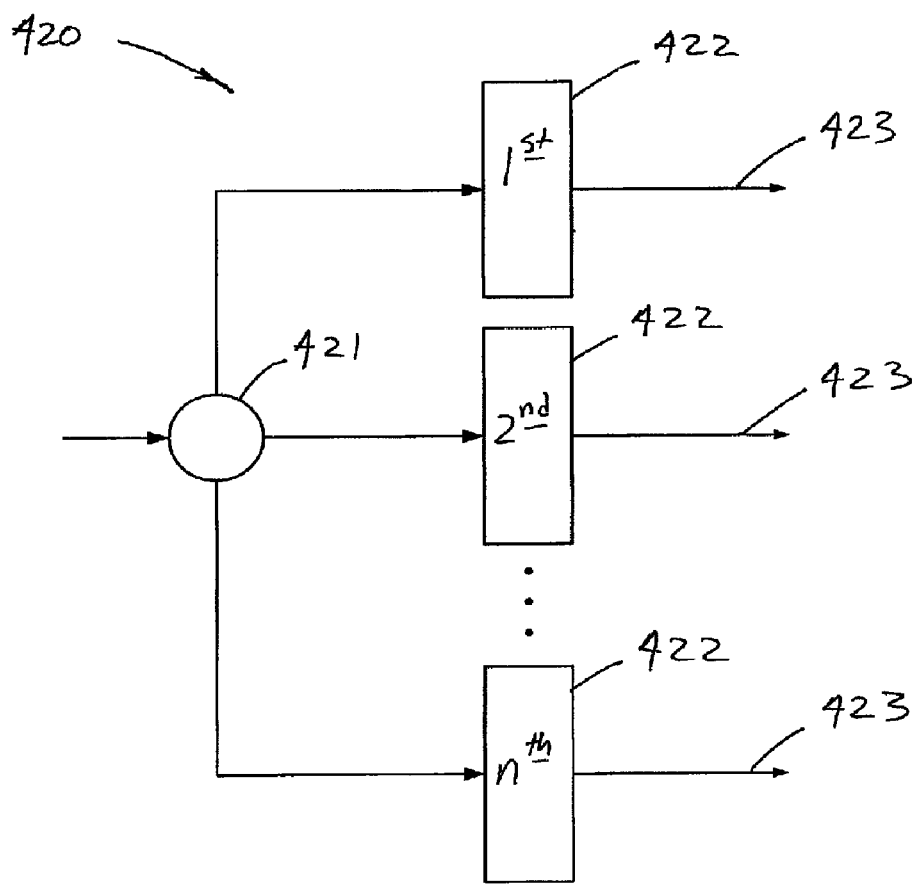
FIG. 11A is a simplified schematic diagram illustrating a pressure control apparatus for use with a microfluidic device according to embodiments of the present invention.

FIG. 11A diagrammatically illustrates an embodiment of a simplified controlled supply pressure apparatus 420 capable of providing multiple supply pressures to multiple supply outlets 423. Supply pressure apparatus 420 includes a single pressure regulator/transducer 421 that can be used to selectively supply pressure to each of a plurality of accumulators 422 (one through n). Pressure regulator/transducer 421 can employ rotary motion to couple its outlet with the desired accumulator 422. Each of the accumulators 422 (one through n) can supply a specific supply outlet 423 (one through n).

A key consideration regarding the supply of controlled pressure to a microfluidic device is that these devices typically require very little actual flow during the introduction of fluids, or during valve actuation. Because very little volume is required, it is not necessary to have a dedicated pressure regulator/transducer 421 for each supply outlet 423. Instead, a single pressure regulator/transducer 421 can periodically update the pressure within each accumulator 422 (one through n) to the extent necessary to account for any small amount of pressure change that occurred since the previous pressure update.

Figure 11B:
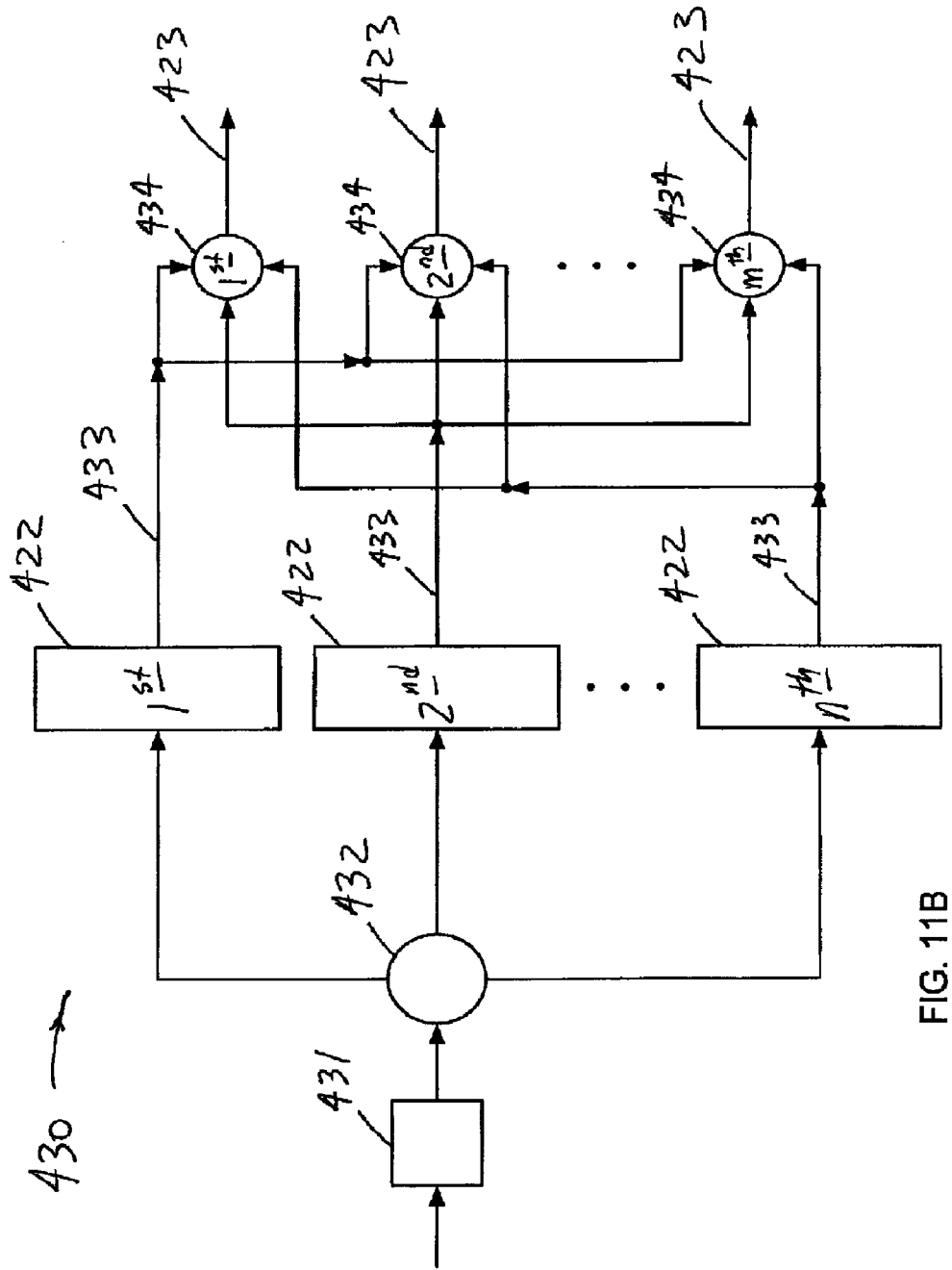
FIG. 11B is a simplified schematic diagram illustrating a pressure control apparatus for use with a microfluidic device according to embodiments of the present invention.

FIG. 11B diagrammatically illustrates another embodiment of a simplified controlled supply pressure apparatus capable of providing multiple supply pressures to multiple supply outlets 423. Supply pressure apparatus 430 includes a single pressure regulator/transducer 431 that can be used to selectively supply pressure to each of the accumulators 422 (one through n). In some embodiments, an accumulator selector valve 432, such as a rotary valve, can be used to selectively couple the output of pressure regulator/transducer 431 with an accumulator 422. In some embodiments, an integrated component can be used in place of pressure regulator/transducer 431 and accumulator selector valve 432, such as pressure regulator/transducer 421 shown in FIG. 11A. Each of the supply outlets 423 (one through m) can be supplied by an associated supply outlet selector valve 434 (one through m) that can selectively place a supply outlet 423 in fluid communication with an accumulator 422. In some embodiments, each accumulator 422 is used to supply a particular supply outlet 423, thereby eliminating the need for supply outlet selector valves 434.

Figure 11C:
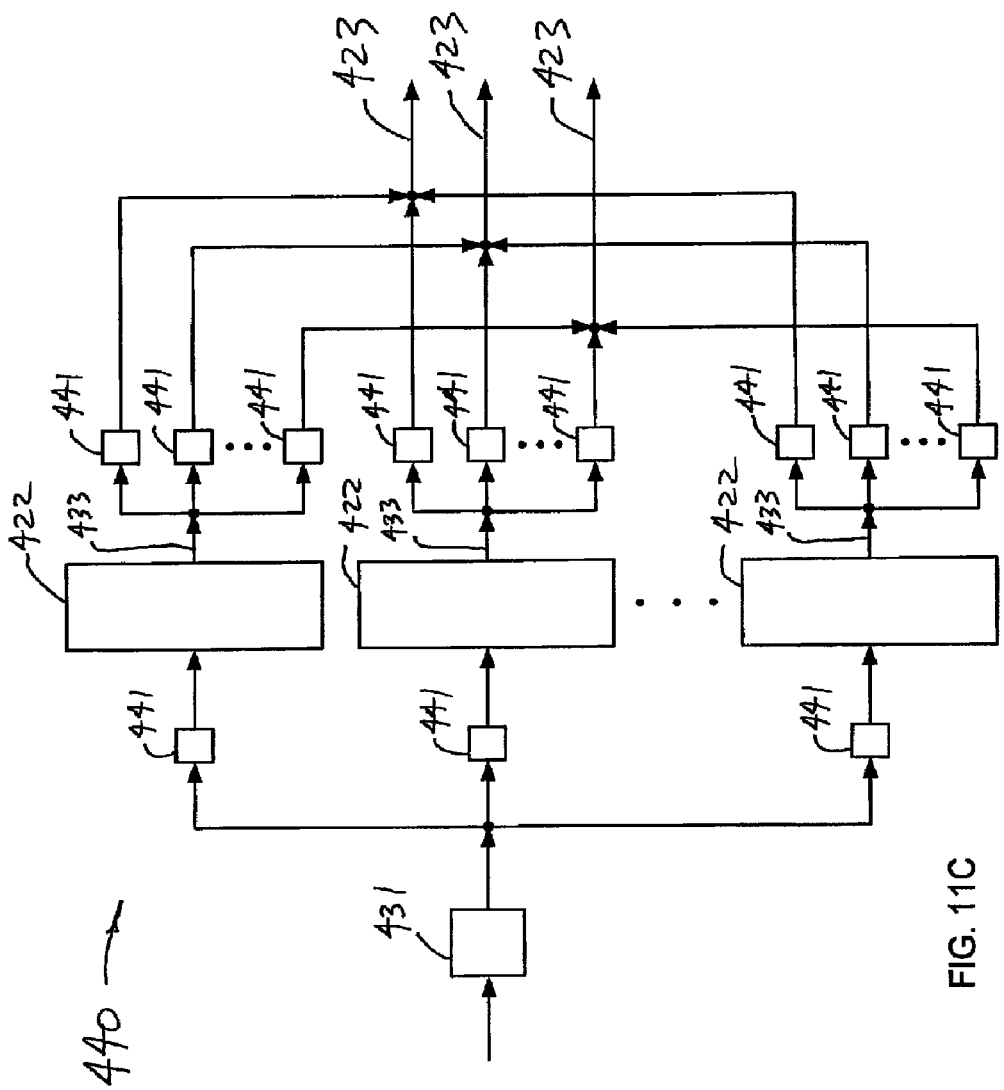
FIG. 11C is a simplified schematic diagram illustrating a pressure control apparatus for use with a microfluidic device according to embodiments of the present invention.

FIG. 11C diagrammatically illustrates another embodiment of a simplified controlled supply pressure apparatus capable of providing multiple supply pressures to multiple supply outlets 423. Supply pressure apparatus 440 is similar to supply pressure apparatus 430, but employs simple single inlet/outlet valves 441 in place of the more complex selector valves used in the embodiment of supply pressure apparatus 430 shown in FIG. 11B. In some embodiments, each accumulator 422 is used to supply a particular supply outlet 423, thereby eliminating the need for the associated selector valves 441.

Figure 11D:
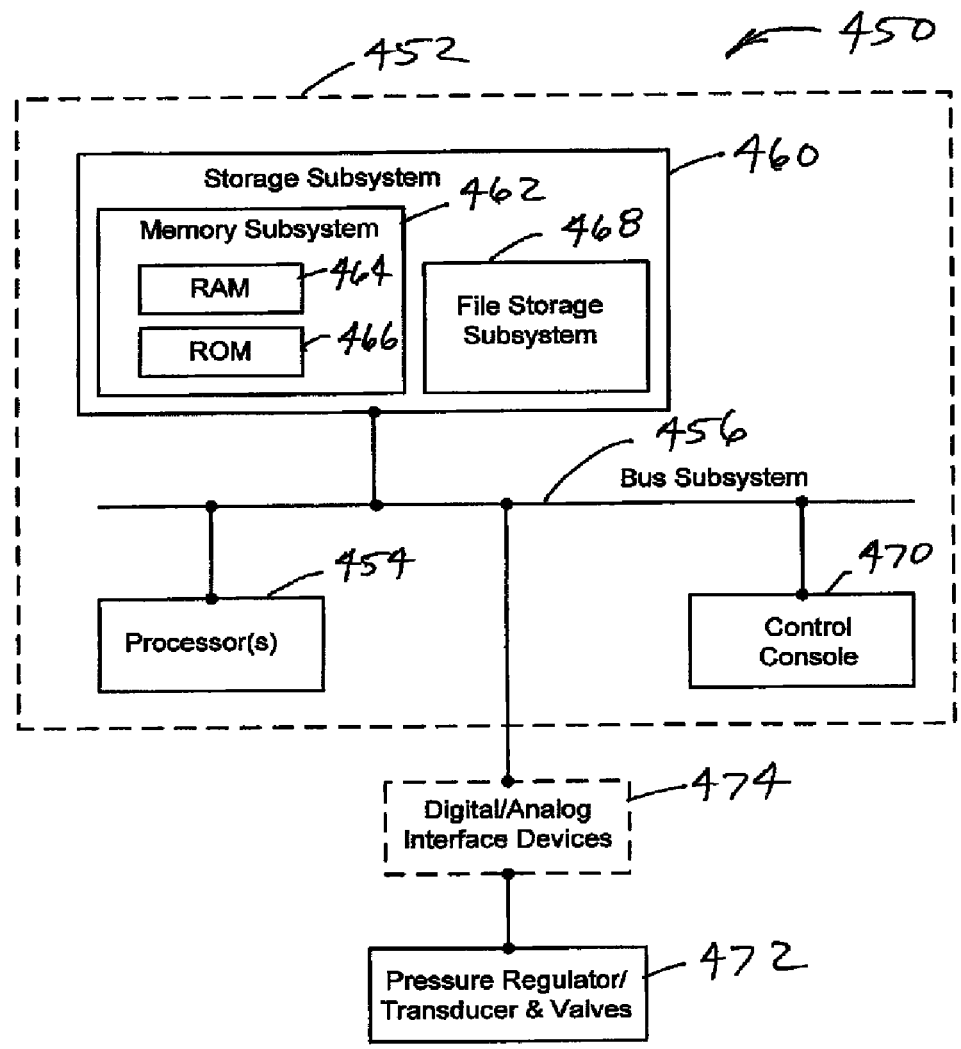
FIG. 11D is a simplified schematic diagram illustrating a control system for a pressure control apparatus for use with microfluidic devices according to embodiments of present invention.

FIG. 11D diagrammatically illustrates an embodiment of a control system 450 that can be used to control the operation of a simplified controlled supply pressure apparatus. Control unit 452 typically includes at least one processor 454 which communicates with a number of peripheral devices via bus subsystem 456. These peripheral devices typically include a storage subsystem 460 (memory subsystem 462 and file storage subsystem 468), and a control console 470.

Storage subsystem 460 maintains the basic programming and data constructs that provide the functionality of the control unit 452. Software modules for implementing control of the pressure regulator/tranducer and valves 472 discussed above are typically stored in storage subsystem 460. Storage subsystem 460 typically includes memory subsystem 462 and file storage subsystem 468.

Memory subsystem 462 typically includes a number of memories including a main random access memory (RAM) 464 for storage of instructions and data during program execution and a read only memory (ROM) 466 in which fixed instructions are stored.

File storage subsystem 468 provides persistent (non-volatile) storage for program and data files, and can include a hard drive, a disk drive, or other non-volatile memory such as flash memory. The disk drive can be used to input the software modules discussed above. Alternatively, any other means known in the art may be used to input the software modules, such as a USB port.

Control console 470 can provide an interface with a user. Control console 470 can be used to display information to the user and receive input from the user.

In this context, the term "bus subsystem" is used generically so as to include any mechanism for letting the various components and subsystems communicate with each other as intended. Bus subsystem 456 is shown schematically as a single bus, but a typical system has a number of buses such as a local bus and one or more expansion buses (e.g., ADB, SCSI, ISA, EISA, MCA, NuBus, or PCI), as well as serial and parallel ports.

Control system 450 can include digital to analog interface devices 474 if necessary so as to provide analog control signals to the pressure regulator and assorted valves.

Reduced Dehydration

Embodiments of the present invention providing methods and related microfluidic devices for reducing dehydration of a microfluidic device will now be described with reference to FIGS. 12A, 12B, and 12C. Dehydration of a microfluidic device can occur, for example, when the device is used to process a sample fluid that includes water.

Microfluidic device vent channels may provide a low impedance path for dehydration. Although microfluidic devices can often be blind filled with control fluid, reagent fluid, and sample fluid because air trapped within the device is able to escape through the device material (e.g., elastomeric material), vent channels are often established to facilitate faster loading. A vent channel can be located such that the air escaping through the device material can be collected by a vent channel, thereby reducing the distance within device material through which the escaping air travels. However, these vent channels provide a path by which dehydration may occur, especially during elevated temperature processing.

FIG. 12A shows a microfluidic device 480 that includes vertical vent channels 482, horizontal vent channels 484, and a ring of sacrificial chambers called dehydration chambers 486. Dehydration chambers 486 can be used to provide a reservoir of sample fluid that will evaporate first, thereby helping to reduce the amount of dehydration that interior chambers may experience. However, adjacently located vent channels 482 and 484 may provide low impedance dehydration paths that serve to increase the amount of dehydration that occurs.

Figure 12B:
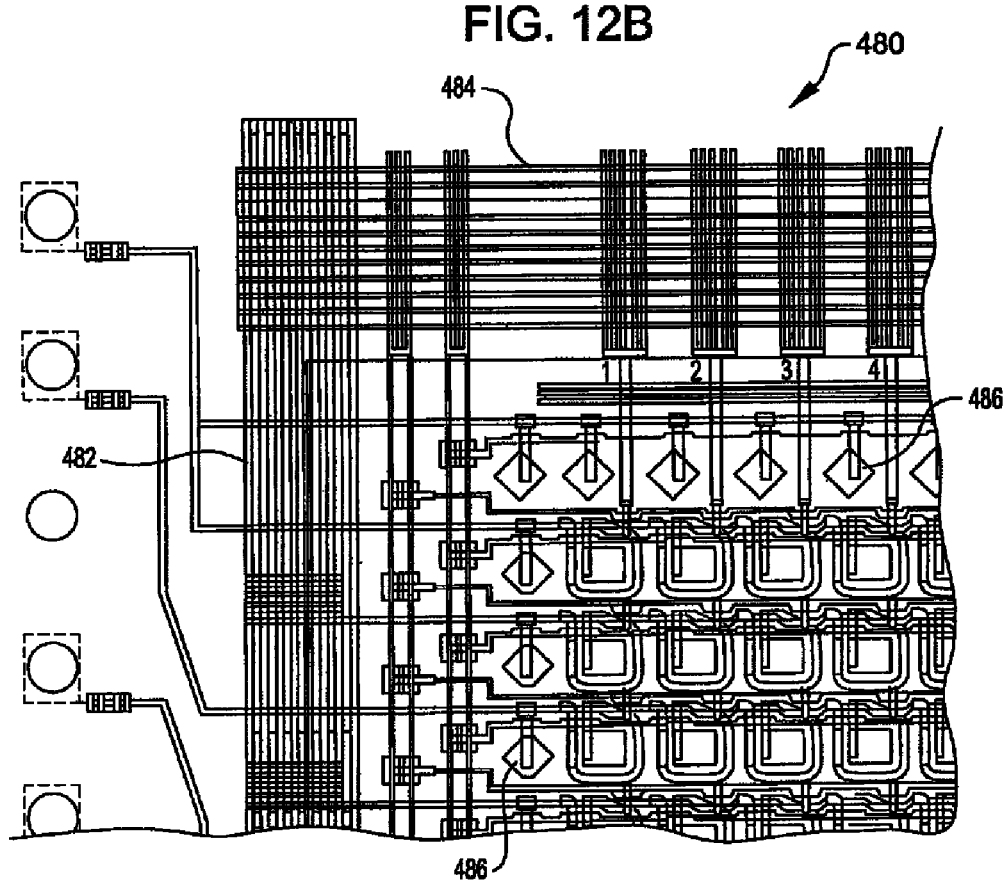
FIG. 12B shows a close-up view of the upper left hand corner of the microfluidic matrix device of FIG. 12A.
Figure 12C:
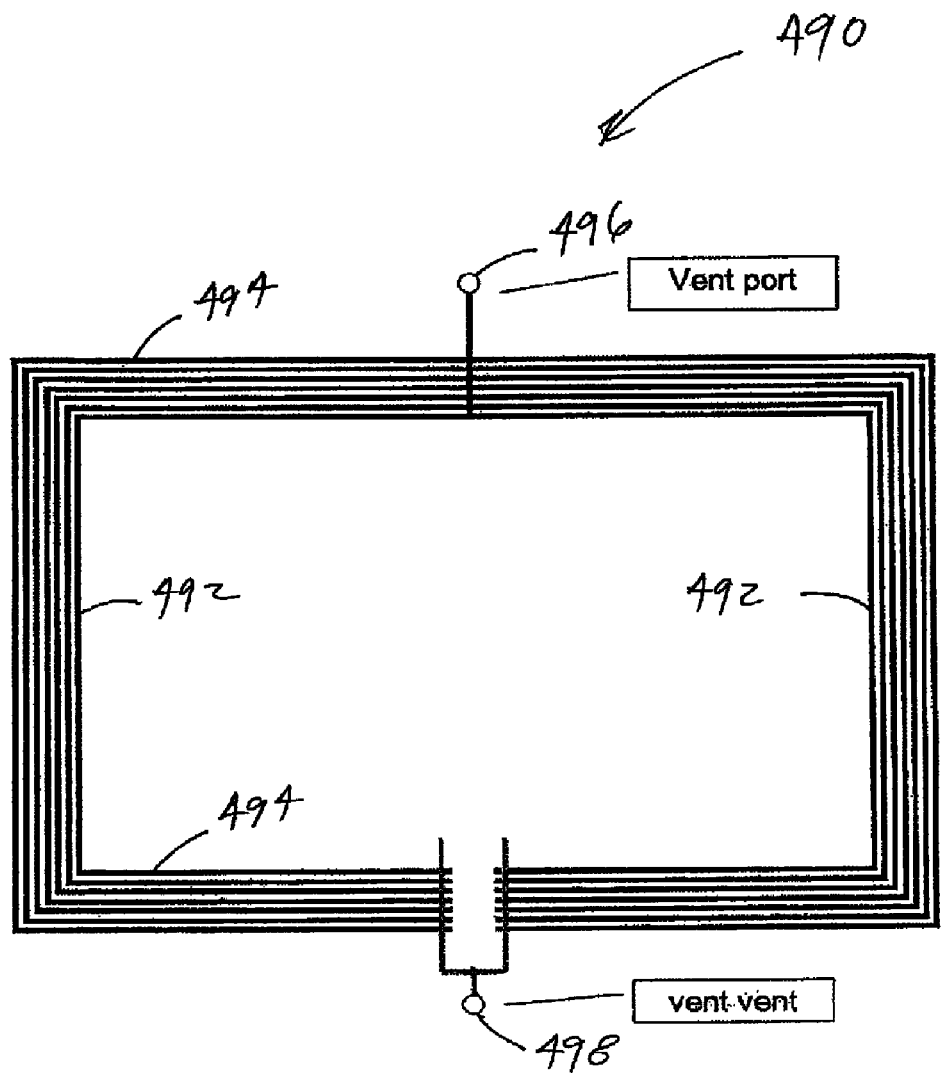
FIG. 12C is a simplified schematic diagram illustrating microfluidic device vent lines connected with a vent port and a vent according to embodiments of the present invention.

FIG. 12B is a close-up view of a portion of microfluidic device 480 of FIG. 12A, and shows a number of adjacently located vertical vent channels 482 and horizontal vent channels 484.

To reduce dehydration, one or more vent channels can be filled with substantially non-permeable fluid, such as a perfluoropolyether oil. The substantially non-permeable fluid can be introduced after control fluid, reagent, and sample are loaded into the chip. At this point in time, the vent channels 482 and 484 have served their purpose, but remain as a dehydration liability.

A vent channel 482 or 484 can be filled in a variety of ways. One approach is to simply blind fill a vent channel 482 and/or 484 with a substantially impermeable fluid, such as control fluid. With blind filling, any air trapped within the vent channel can escape through the permeable elastomeric material. In microfluidic device 480, vertical vent channels 482 are all directly connected with each other and horizontal vent channels 484 are all directly connected with each other. However, vertical vent channels 482 and horizontal vent channels 484 are on different planes and communicate with each other only through the permeable elastomeric material. A small modification can be made to interconnect vertical vent channels 482 with horizontal vent channels 484 by forming a few well placed vias in the 4 corners of the microfluidic device 480. These vias can be formed in a variety of ways, such as with a laser. An existing vent channel port that provides an escape path for air during loading of the microfluidic device 480 can be used as an introduction port for the substantially non-permeable fluid.

Additional embodiments are best described with reference to FIG. 12C, which diagrammatically illustrates microfluidic device configuration 490 that includes interconnected vertical vent channels 492 and horizontal vent channels 494 that are in fluid communication with a vent channel port 496. These concentric vent channels can be located so as to go almost entirely around a microfluidic device. In one embodiment, a vent channel vent 498 is provided that is not fluidically connected with vent channels 492 or 494, but is located within another plane of the microfluidic device and is not connected by a via. A substantially non-permeable fluid, such as a perfluoropolyether oil, can be injected into vent channel port 496, thereby pushing air within vent channels 492 and 494 towards vent channel vent 498, where it escapes through the permeable elastomeric material to emerge from vent channel vent 498. A vent channel vent 498 that is not directly connected with vent channels 492 and 494 may provide better retention for the substantially non-permeable fluid. In some embodiments, vent channel vent 498 can be connected with vent channels 492 and 494, thereby facilitating faster loading of the substantially non-permeable fluid. However, this may result in reduced retention of the substantially non-permeable fluid as compared to configurations where vent channel vent 498 is not directly connected with vent channels 492 and 494.

Improved Mixture Ratio Control

Embodiments of the present invention providing microfluidic devices and related methods for improved sample to reagent mixture ratio control will now be described with reference to FIG. 13. Often, it may be important for sample fluids and reagent fluids to be mixed within certain ratio limits.

Figure 13:
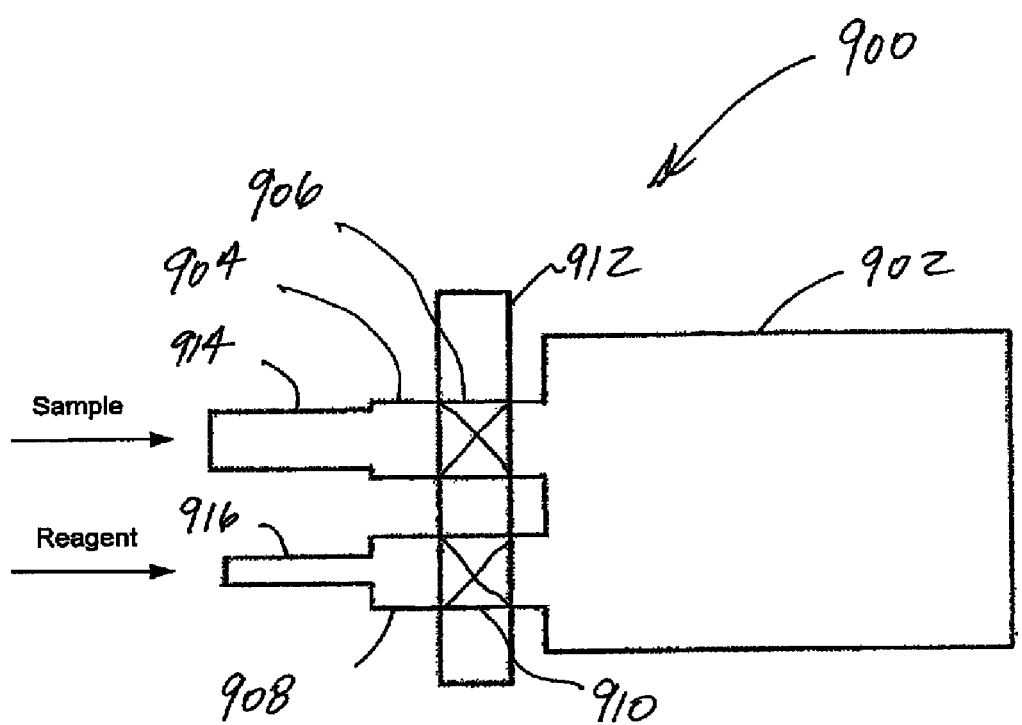
FIG. 13 shows a diagram illustrating a microfluidic device configuration providing flow rate control of a sample and a reagent introduced into a reaction chamber according to embodiments of the present invention.

FIG. 13 diagrammatically illustrates a microfluidic device configuration 900 providing flow rate control of a sample fluid and/or a reagent fluid introduced into a reaction chamber 902. Reaction chamber 902 is in fluid communication with a sample channel 904 through a sample interface valve 906 for controlling fluid communication between reaction chamber 902 and sample channel 904. Sample channel 904 can be in fluid communication with a sample chamber (not shown) for storing a sample fluid. Reaction chamber 902 is also in fluid communication with a reagent channel 908 through a reagent interface valve 910 for controlling fluid communication between reaction chamber 902 and reagent channel 908. Reagent channel 908 can be in fluid communication with a reagent chamber (not shown) for storing a reagent fluid. Sample interface valve 906 and reagent interface valve 910 can be actuated via a control channel 912. Sample channel 904 can include a sample channel restriction 914 for controlling the flow rate of sample fluid into reaction chamber 902. Likewise, reagent channel 908 can include a reagent channel restriction 916 for controlling the flow rate of reagent fluid into reaction chamber 902. In the embodiment shown, sample interface valve 906 is disposed between sample channel restriction 914 and reaction chamber 902, and reagent interface valve 910 is disposed between reagent channel restriction 916 and reaction chamber 902.

Various embodiments of a microfluidic device providing flow rate control are possible. For example, sample channel restriction 914 can be disposed between sample interface valve 906 and reaction chamber 902, and reagent channel restriction 916 can be disposed between reagent interface valve 910 and reaction chamber 902. In some embodiments, sample interface valve 906 can be actuated via a separate sample interface control channel (not shown), and reagent interface valve 910 can be actuated via a separate reagent interface control channel (not shown). In some embodiments, a microfluidic device can include a plurality of flow rate controlling configurations. In some embodiments, a microfluidic device can incorporate flow rate control for just a reagent fluid, or even just a sample fluid. In some embodiments, the amount of sample fluid received by a reaction chamber 902 can exceed the amount of reagent fluid received. In some embodiments, the ratio of sample fluid to reagent fluid received by a reaction chamber 902 can be approximately a specific ratio, such as ten to one.

Embodiments of the present invention provide related methods for using a microfluidic device configured to provide flow rate control. A method can include, for example, providing a microfluidic device with flow rate control, introducing sample fluid into a sample chamber with sample interface valve 906 closed, introducing reagent fluid into a reagent chamber with reagent interface valve 910 closed, opening sample interface valve 906 to transfer sample fluid to reaction chamber 902, opening reagent interface valve 910 to transfer reagent fluid to reaction chamber 902, closing sample interface valve 906 after the transfer of sample fluid to reaction chamber 902, and closing reagent interface valve 910 after the transfer of reagent fluid to reaction chamber 902. In some embodiments, sample interface valve 906 and reagent interface valve 910 are opened at the same time, and closed at the same time. In embodiments with a separate sample interface control channel and/or a separate reagent interface control channel, sample interface valve 906 and reagent interface valve 910 can be opened at the same time or different times, and closed at the same time or different times.

Increased Resistance to Compression Fixture Induced Failure

Embodiments of the present invention providing microfluidic devices and systems with increased resistance to compression fixture pressure induced failures will now be described with reference to FIGS. 14A, 14B, 15, 16, 17, 18A, 18B, 19, and 20. Compression fixtures are often used to hold a microfluidic device in place during elevated temperature processing. A compression fixture may cause increased pressure levels within a microfluidic device, which may result in a sufficient pressure differential across a closed isolation valve for valve failure, which may result in failure of the microfluidic device.

Figure 14A:
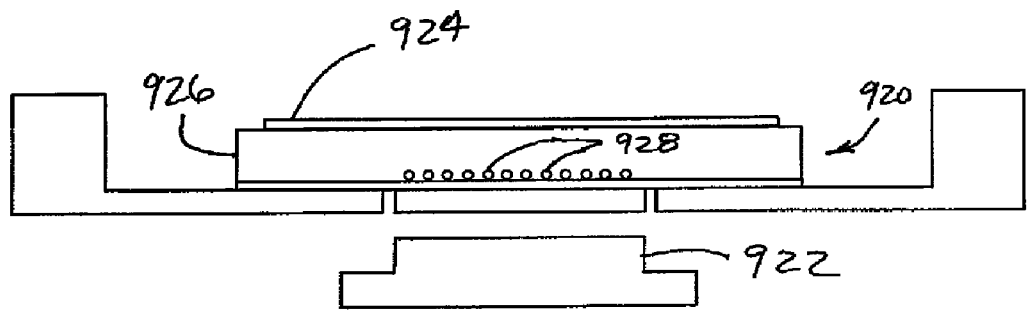
FIG. 14A shows a cross-section view of a microfluidic device being held in thermal communication with a thermal control source via a compression fixture.

FIG. 14A shows a cross-section view of a microfluidic device 920 being held in thermal communication with a thermal control source 922 via a compression fixture 924. Compression fixture 924 may impart compressive forces on the top of an elastomeric portion 926 of microfluidic device 920. These compressive forces typically result in internal compressive stresses within elastomeric portion 926, and typically result in increased pressure levels within fluid filled structures of elastomeric portion 926, such as within reaction sites 928 that typically contain a mixture of sample fluid and reagent fluid being reacted at an elevated temperature.

Figure 14B:
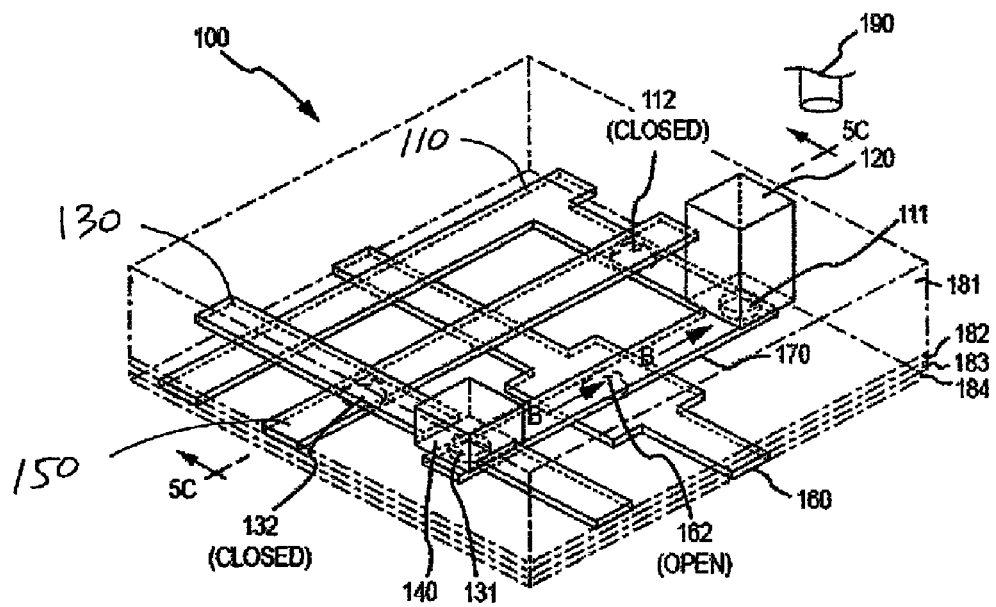
FIG. 14B depicts a perspective view of a unit cell of a microfluidic device according to embodiments of the present invention.

FIG. 14B depicts a perspective view of an exemplary unit cell 100 of a microfluidic device that can provide one of the reaction sites 928 shown in FIG. 14A. Various fluid filled structures that may be subject to increased pressure levels in response to compression fixture 924 forces can be seen, such as first channel 130, first isolation valve 132, first chamber 140, second channel 110, second isolation valve 112, second chamber 120, control channel 150, interface channel 160, interface valve 162, and reaction channel 170. Compression fixture 924 may be used during elevated temperature processing, which typically occurs only after the microfluidic device has been loaded with sample fluid, reagent fluid, and control fluid. At this point, first isolation valve 132 and second isolation valve 112 are closed and are maintained closed by pressure within control channel 150, and interface valve 162 is open, thereby allowing mixing of sample and reagent fluid. Compression fixture 924 forces may result in increased pressure within the mixture of sample and reagent fluid trapped between first isolation valve 132 and second isolation valve 112. Often, compression fixture 924 forces do not result in corresponding increases in pressure within portions of first channel 130 and second channel 110 that are disposed upstream of first isolation valve 132 and second isolation valve 112 respectively, due to the ability of fluid within these channels to flow out of the microfluidic device. This may result in an increased pressure differential across first isolation valve 132 and/or second isolation valve 112, which may reach a magnitude necessary to overcome the actuation force provided by control channel 150, thereby causing valve failure. The potential for valve failure under these circumstances is aggravated because the pressure within control line 150 may remain essentially constant where control fluid within control line 150 is free to be pushed out towards the accumulator. The entire volume of control fluid is sufficiently small that, when some of the control fluid is pushed into the accumulator, it causes a negligible change in gas volume within the accumulator, and hence a negligible change in accumulator pressure.

Figure 15:
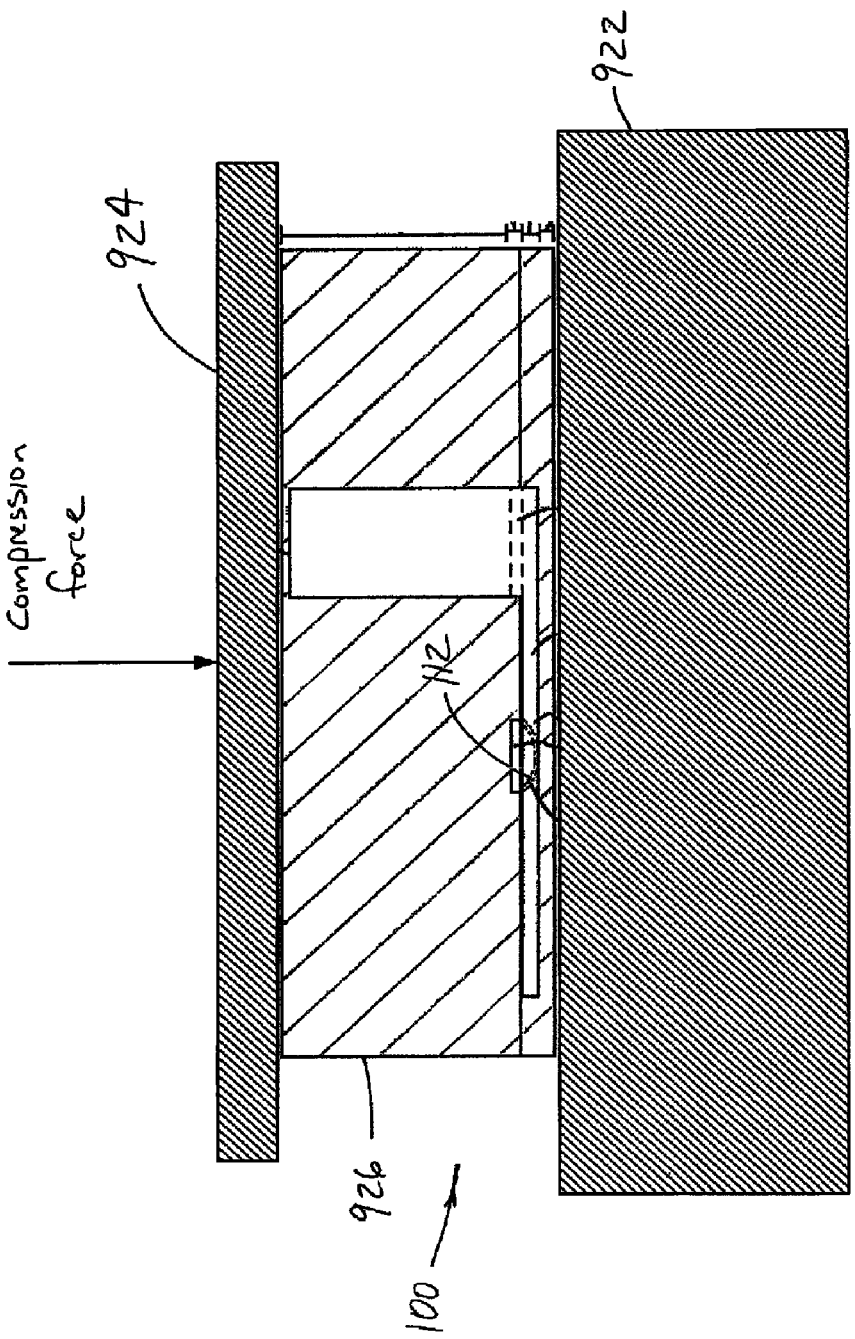
FIG. 15 shows a cross-section view of a microfluidic device unit cell being held in thermal communication with a thermal control source via a compression fixture.

FIG. 15 shows a cross-section view of a microfluidic device unit cell 100 being held in thermal communication with a thermal control source 922 via a compression fixture 924. Compression fixture 924 force results in downward deflection of the upper portions of elastomeric portion 926, which typically results in increased pressure within the fluid trapped between first isolation valve 132 (not shown) and second isolation valve 112, as discussed above. This increased pressure may result in a pressure differential across one or both isolation valves sufficient in magnitude to cause valve failure, so that the previously trapped fluid is squeezed out of the unit cell 100.

Embodiments of the present invention can provide improved resistance to compression fixture pressure induced failures by restricting the backflow of control fluid. By restricting backflow of control fluid, the pressure within control channel 150 is elevated during compression fixture 924 use, thereby providing increased actuation forces to first isolation valve 132 and second isolation valve 112. With increased actuation forces, first isolation valve 132 and second isolation valve 112 are capable of resisting increased pressure differentials before failure.

Figure 16:
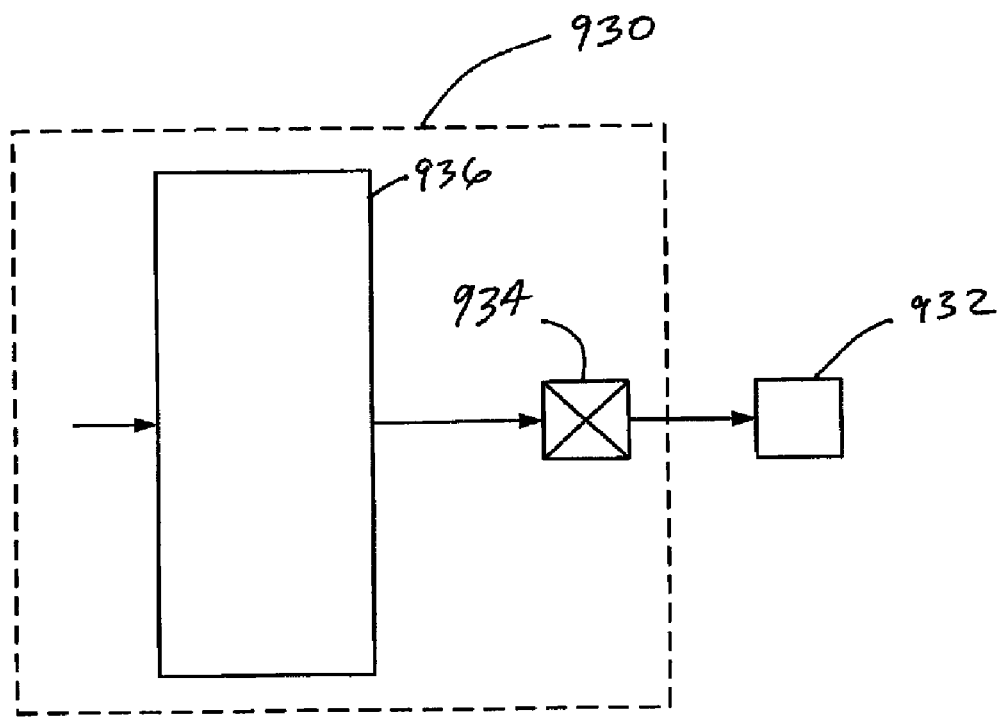
FIG. 16 shows a diagram of a control fluid introduction device with a backflow prevention feature according to embodiments of the present invention.

FIG. 16 shows an embodiment of the present invention that includes a control fluid introduction device 930 that restricts the backflow of control fluid from a microfluidic device 932. In some embodiments, a control fluid introduction device 930 can include a backflow restriction feature 934 that restricts the backflow of control fluid during compression fixture 924 use. A variety of devices can be used as a backflow restriction feature 934, such as a valve that is closed during compression fixture use, or a check valve that provides for normal control channel use required to actuate valves within the microfluidic device 932. In some embodiments, control fluid introduction device 930 can be adapted to eliminate the presence of gas within accumulator 936 during compression fixture 924 use. Elimination of gas within accumulator 936 helps to reduce the backflow of control fluid during compression fixture 924 use.

Figure 17:
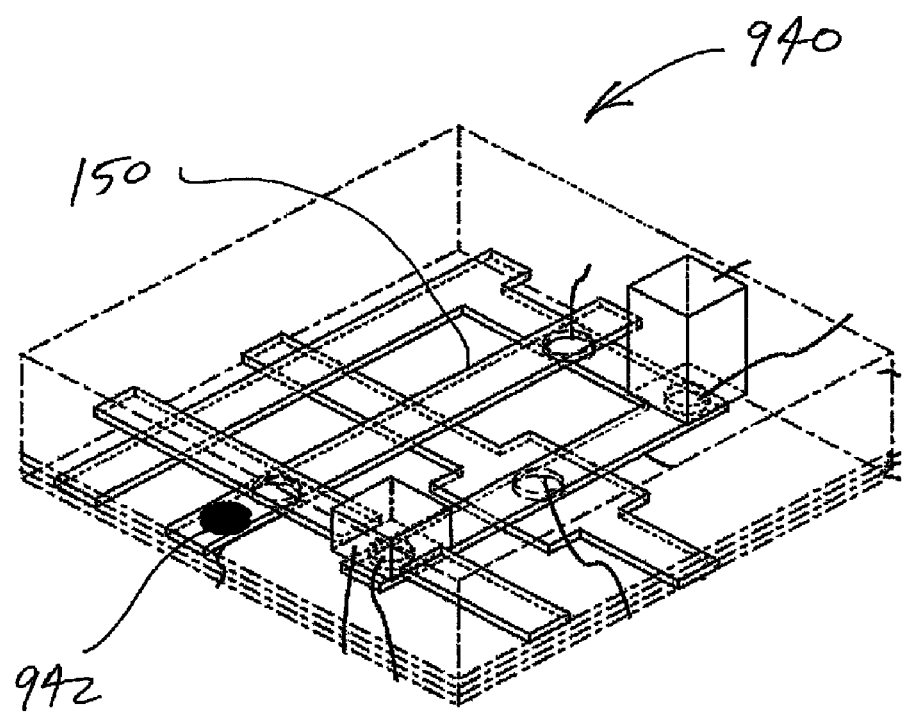
FIG. 17 depicts a perspective view of a unit cell of a microfluidic device having a backflow prevention feature according to embodiments of the present invention.

FIG. 17 depicts a perspective view of a unit cell 940 of a microfluidic device having an on-chip backflow prevention feature 942 according to embodiments of the present invention. An on-chip backflow prevention feature 942 can be, for example, located so as to prevent backflow of control fluid within control channel 150 during compression fixture 924 use. In some embodiments, the on-chip backflow prevention feature 942 can be a check valve, such as check valves as described in co-pending and commonly owned International Publication Number WO 2008/043046 A2, filed Oct. 4, 2007, which is incorporated herein for all purposes. In some embodiments, the on-chip backflow prevention feature 942 can be a valve that can be fused in a close position, such as by an application of thermal energy or by an application of low-frequency ultraviolet light and/or other electromagnetic radiation. In some embodiments, a valve is fused in the closed position by way of polymer cross-linking. In some embodiments, the polymer cross-linking is induced by the application of ultraviolet light (e.g., 200 to 240 nm wavelength light) and/or other electromagnetic radiation. In some embodiments, backflow of control fluid within control channel 150 can be restricted by sealing closed control channel 150 either within or outside the elastomeric portion of the microfluidic device (e.g., by application of ultraviolet light and/or other electromagnetic radiation, by application of thermal energy, or actuation of a guided pin or cam). In some embodiments, control channel 150 may be self-sealed, such as by solidifying control fluid within control channel 150.

Figure 18A:
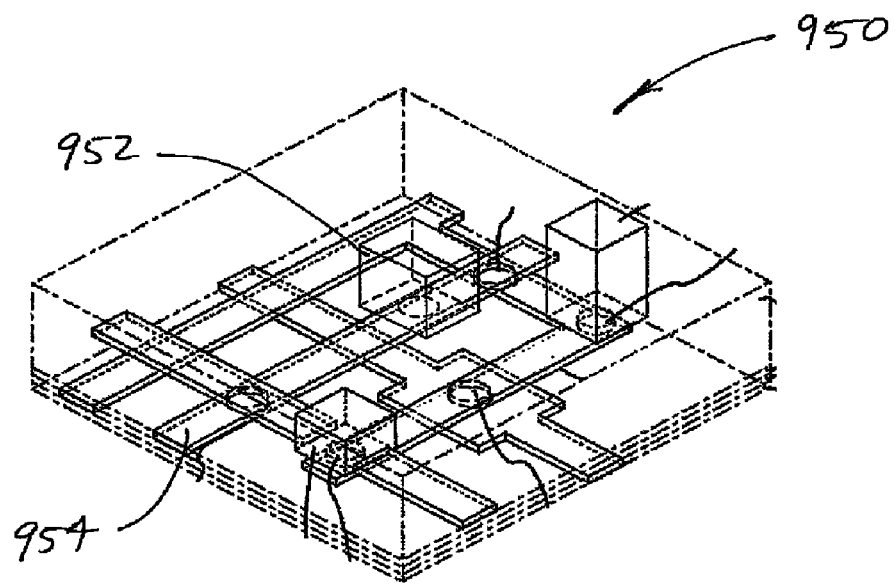
FIG. 18A depicts a perspective view of a unit cell of a microfluidic device having a pressure compensation feature according to embodiments of the present invention.
Figure 18B:
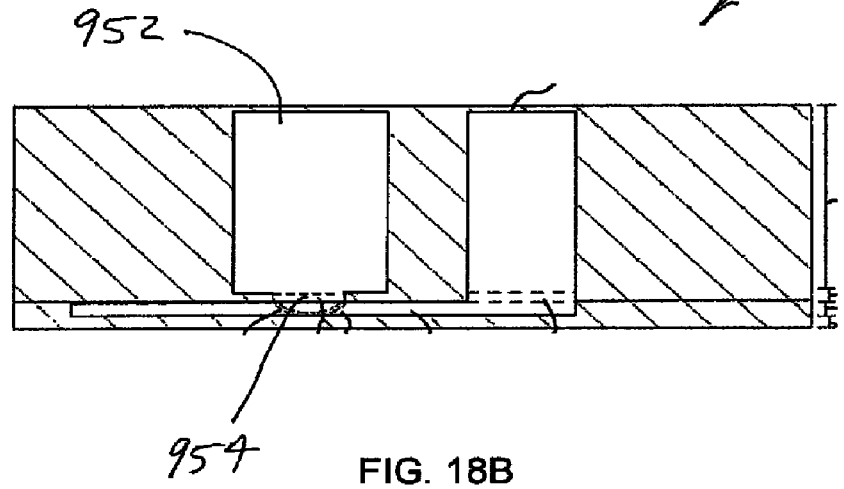
FIG. 18B shows a cross-section view of a microfluidic device unit cell having a pressure compensation feature according to embodiments of the present invention.

FIG. 18A depicts a perspective view of a microfluidic device unit cell 950 having a pressure compensation feature according to embodiments of the present invention. A pressure compensation feature can include, for example, a control fluid chamber 952 in fluid communication with control channel 954. During compression fixture 924 use, control fluid is squeezed out of control fluid chamber 952, which may serve to increase the pressure within control channel 954 by increasing the amount of control fluid that must be accommodated within a limited volume elsewhere. The level of pressure increase can be further increased through the use of features that limit the backflow of control fluid, or that limit the space available for the control fluid to escape to, or both. FIG. 18B shows a cross-section view of a microfluidic device unit cell 950 having a pressure compensation feature. It should be appreciated that downward deflection of the top surface of the microfluidic device that may occur during compression fixture use may result in squeezing control fluid out of control fluid chamber 952, thereby increasing pressure within control channel 954 and helping to resist against pressure induced valve failure.

Figure 19:
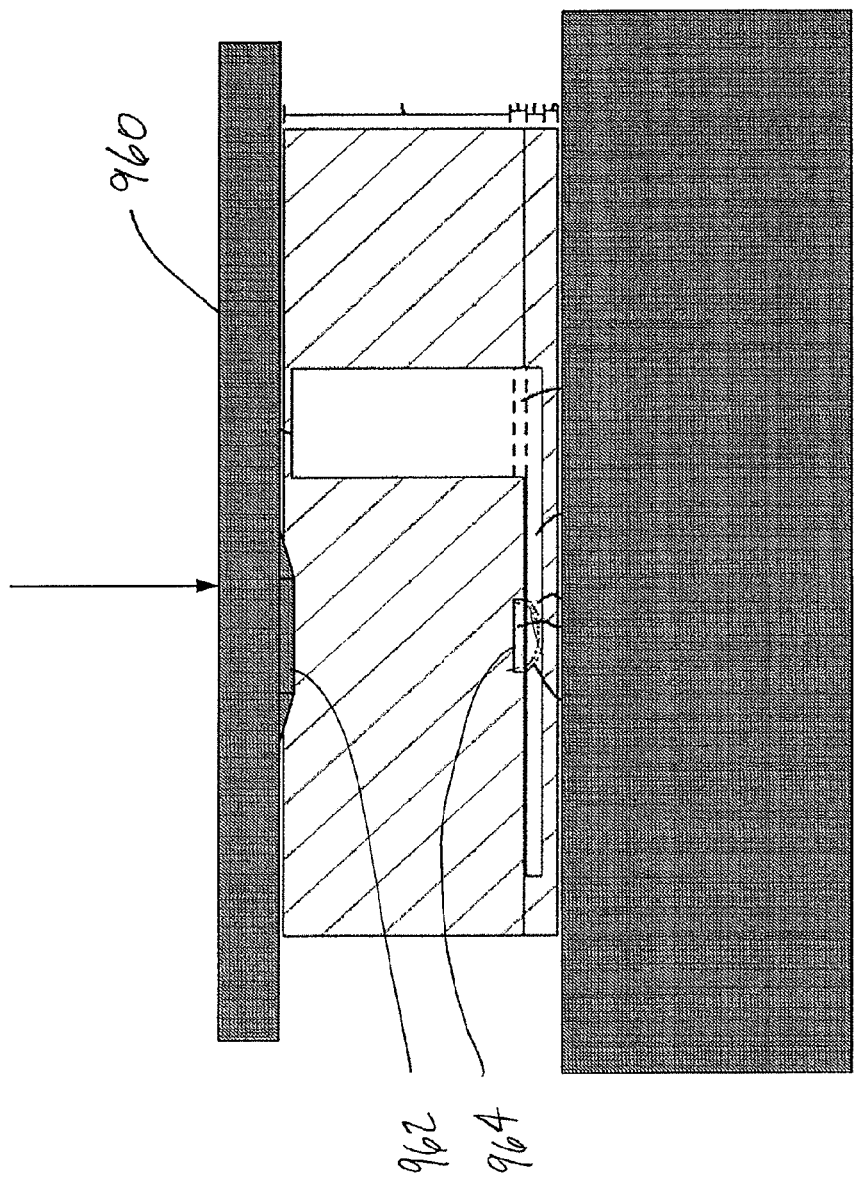
FIG. 19 shows a cross-section view of a microfluidic device unit cell being held in thermal communication with a thermal control source by way of a preferential compression fixture according to embodiments of the present invention.

FIG. 19 shows a cross-section view of a microfluidic device unit cell being held in thermal communication with a thermal control source by way of a preferential compression fixture 960 according to embodiments of the present invention. A preferential compression fixture 960 can include, for example, a pad 962 for applying pressure preferentially to areas of a microfluidic device where control-fluid-filled structures exist so as to produce increased control fluid pressure in control channel 964 in response to compression by the preferential compression fixture 960. As shown, pad 962 can be used to locally cause increased downward deflection of the upper surface of the microfluidic device in locations above control-fluid-filled structures, such as control channel 964. This localized increased downward deflection creates localized increased internal compressive strains that imposed increased amounts of constriction upon control-fluid-filled structures. This increased constriction may elevate the pressure level within the control fluid, especially where backflow of control fluid is restricted. As discussed above, increased control fluid pressure levels provides increased resistance to valve failure.

Figure 20:
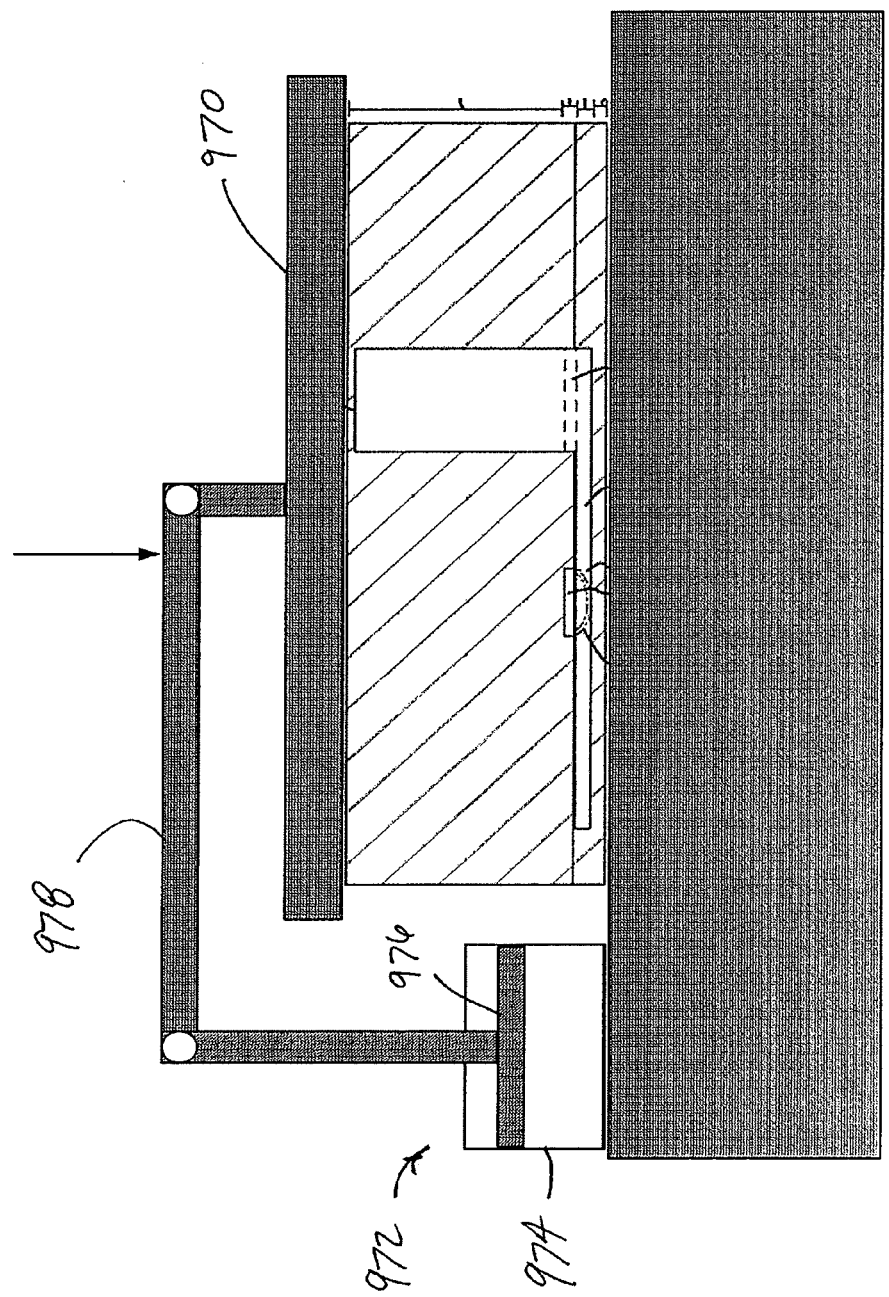
FIG. 20 shows a cross-section view of a microfluidic device unit cell being held in thermal communication with a thermal control source by way of a compression fixture coupled with a pressure compensation device according to embodiments of the present invention.

FIG. 20 shows a simplified diagrammatic cross-section view of a microfluidic device unit cell being held in thermal communication with a thermal control source by way of a compression fixture 970 coupled with a pressure compensation device 972 according to embodiments of the present invention. A pressure compensation device 972 can include, for example, a control-fluid-pressurization device 974 that can be used to produce increased control fluid pressure in response to compression fixture 970 force. The amount of pressure increase for a given amount of compression fixture 970 force can be varied so as to provide sufficient increases in interface valve actuation forces necessary to counteract resulting pressure differentials across interface valves. The control-fluid-pressurization device 974 can include a syringe type plunger 976 that is subjected to an actuation force when the compression fixture 970 is used. The control-fluid-pressurization device 974 can provide control fluid pressure increases proportional to the amount of compression fixture 970 force. The control-fluid-pressurization device 974 can be coupled with the compression fixture 970 via a mechanical linkage 978 that provides a suitable level of actuation force to control-fluid-pressurization device 974 in response to compression fixture 970 force. The control-fluid-pressurization device 974 can be independently actuated in response to a signal indicating the amount of compression fixture 970 force, and the signal can be generated using a force sensing transducer, which can include a strain sensing gage.

Temperature Controlled Reactions with Reduced Condensation

Embodiments of the present invention providing microfluidic methods and systems for conducting temperature controlled reactions so as to reduce condensation levels within a microfluidic device will now be described with reference to FIGS. 21A, 21B, and 21C. Conducting elevated temperature controlled reactions using a microfluidic device having an elastomeric portion sometimes results in condensation within the elastomeric portion.

Figure 21A:
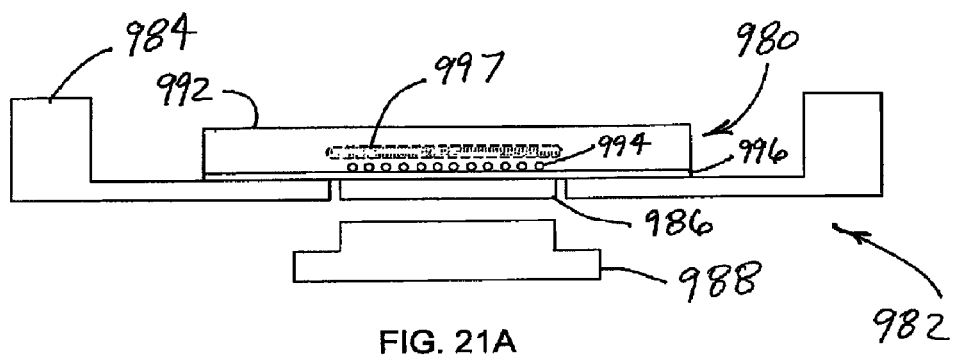
FIG. 21A shows a cross-section diagram of a microfluidic device being heated by a thermal control source.

FIG. 21A shows a cross-sectional diagram of a microfluidic device 980 being heated by a thermal control device 982. Thermal control device 982 may include a carrier 984, an integrated heat spreader 986, a thermal control source 988, and a compression fixture 990 (shown in FIG. 21B). Microfluidic device 980 may include an elastomeric portion 992, reaction sites 994 disposed within elastomeric portion 992, and a device bottom layer 996. During heating, temperatures of the reaction sites 994 are elevated, which results in greater levels of evaporation of water from reaction sites 994, and sample fluid and reagent structures. Some of the evaporated water travels through permeable elastomeric portion 992. Often, temperatures within regions of elastomeric portion 992 permit condensation of the evaporated water, resulting in a thin fogged layer 997. This thin fogged layer 997 is typically located above reaction cells 994. A thin fogged layer 997 does not necessarily prevent fluorescent imaging of the reaction sites.

Figure 21B:
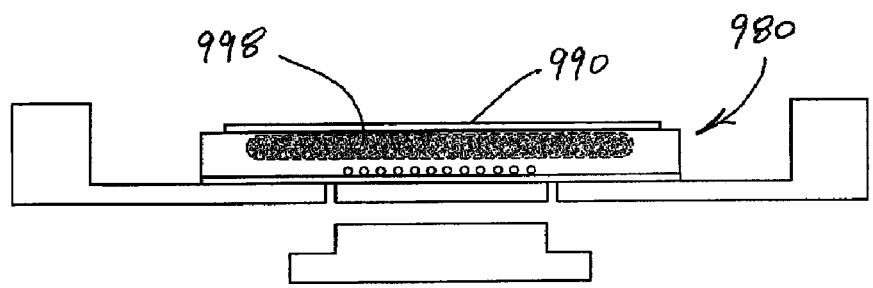
FIG. 21B shows a cross-section diagram of a microfluidic device held in place during heating by a compression fixture.

FIG. 21B shows a cross-sectional diagram of the microfluidic device 980 being held in contact with a thermal control source by way of a non-permeable compression fixture plate 990. Using a non-permeable compression fixture plate, such as the fixture plate 990, during thermal cycling often results in a thick fogged layer 998 with extensive amounts of condensation. The non-permeable compression fixture plate 990 prevents the escape of moisture from contacted surfaces of elastomeric portion 992. The increased moisture content results in increased amounts of condensation. A thick fogged layer 998 may interfere with fluorescent imaging of the reaction sites.

Figure 21C:
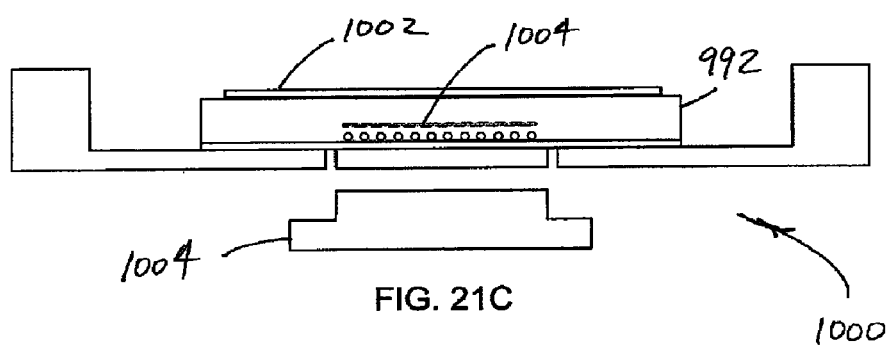
FIG. 21C shows a cross-section diagram of a microfluidic device held in place during heating by a compression fixture according to embodiments of the present invention.

FIG. 21C shows a cross-section diagram of a microfluidic device held in place during heating by a compression fixture 1002 according to embodiments of the present invention. A thermal control device 1000 can be adapted so as to reduce condensation within elastomeric portion 992 in a variety of ways. In one approach, compression fixture 1002 can be heated so as to elevate the temperature of one or more points on elastomeric portion 992 contacted by the compression fixture 1002 above a condensation threshold. When the temperature(s) of the contacted point(s) is/are heated above a condensation threshold, internal temperatures within the elastomeric portion 992 are elevated a sufficient extent to decrease the size and intensity of the fogged layer (resulting in a reduced fogged layer 1004 that is smaller and thus more transparent than thick fogged layer 998) so as to permit fluorescent imaging of the reaction sites. Preferably, the temperature(s) of the contacted point(s) is/are elevated above forty degrees centigrade. More preferably, the temperature(s) of the contacted point(s) is/are elevated above seventy degrees centigrade. The optimum amount of temperature elevation may depend on various factors (e.g., the fluids involved, the temperature of the thermal control source, etc.). A compression fixture 1002 can be heated with the thermal control source 1004, or the thermal control device 1000 can include a separate heat source for heating the compression fixture 1002.

In another approach, the thermal control device 1000 can be adapted for the egress of moisture from elastomeric portion 992. A compression fixture 1002 can, for example, include a permeable or perforated portion that is held in contact with elastomeric portion 992 of the microfluidic device. The permeable or perforated portion of compression fixture 1002 provides a path for moisture egress from elastomeric portion 992. Moisture egress helps to reduce moisture levels within elastomeric portion 992, which in turn helps reduce the extent of any fogging. Thermal control device 1000 can include venting adapted to remove moisture from elastomeric portion 992. The venting can be passive, or forced. Thermal control device 1000 can also include a dehydration device for removing moisture from elastomeric portion 992. Thermal control device 1000 can include a combination of compression fixture heating and adaptation for the egress of moisture from elastomeric portion 992.

Improved Fluorescent Imaging

Embodiments of the present invention providing methods and systems for improved fluorescent imaging of microfluidic devices will now be described with reference to FIGS. 22, 23A, and 23B. The present invention can provide improved imaging through the use of improved illumination that reduces the amount of electromagnetic radiation reflected in the imaging direction.

Figure 22:
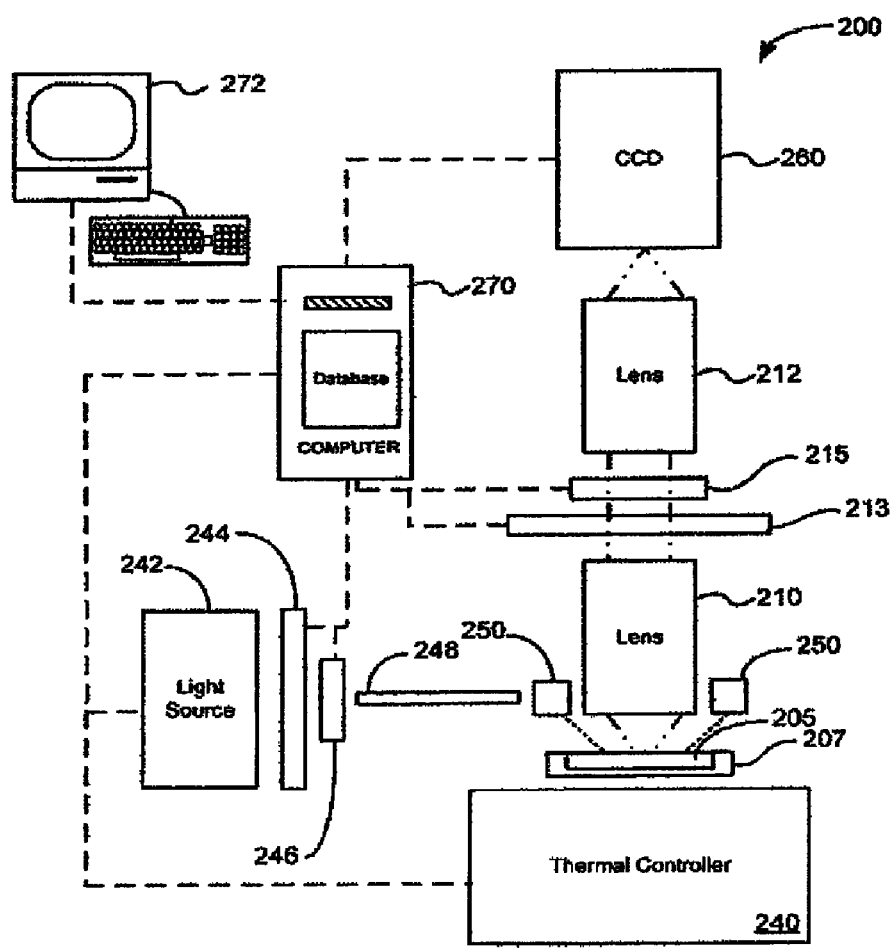
FIG. 22 is a simplified schematic diagram illustrating an optical imaging system according to an embodiment of the present invention.

As illustrated in FIG. 22, optical imaging systems provided according to some embodiments of the present invention include fluorescence imaging systems coupled to thermal control modules. Such systems are adapted to collect data from microfluidic chips with N×M geometries. In some embodiments, N is equal to M. For example, embodiments of the present invention utilize microfluidic devices with 48×48 reaction chambers, 96×96 reaction chambers, and other geometries. In a particular embodiment, 96 samples and 96 reagents are utilized in a microfluidic device with a 96×96 reaction chamber geometry. As will be evident to one of skill in the art, the methods and systems provided according to embodiments of the present invention enable one platform to perform multiple applications.

FIG. 22 is a simplified schematic diagram illustrating an optical imaging system according to an embodiment of the present invention. As illustrated in FIG. 22, an optical source 242 is provided according to embodiments of the present invention. As will be described more fully below, in some embodiments of the present invention, light from optical source 242 is utilized to induce fluorescence in a sample. In other embodiments, chemiluminescence is utilized as a indicator. Depending on the embodiment, system components will be added, removed, or used, as will be evident to one of skill in the art. In various embodiments, optical sources including light emitting diodes (LEDs), lasers, arc lamps, incandescent lamps, and the like are utilized. These sources may be polychromatic or monochromatic. In a particular embodiment, the optical source is characterized by a first spectral bandwidth. In a specific embodiment, the optical source is a white light source producing optical radiation over a spectral range from about 400 nm to about 700 nm. Merely by way of example, a Lambda LS 300W Xenon Arc lamp, available from Sutter Instruments of Novato, Calif. is utilized as an optical source is some embodiments of the present invention. As will be evident to one of skill in the art, other optical sources characterized by larger or smaller spectral bandwidths are capable of being utilized in alternative embodiments.

Excitation filter wheel 244 is illustrated in FIG. 22. In some embodiments, for example, those in which the optical source is polychromatic, the excitation filter wheel 244 is utilized to spectrally filter the light emitted by the optical source 242. Of course, multiple filters could also be used. As an example, in an embodiment, the excitation filter wheel provides a number of spectral filters each adapted to pass a predetermined wavelength range as appropriate for exciting specific fluorescence from a sample. As illustrated in FIG. 22, the excitation filter wheel 244 is coupled to computer 270, providing for computer control of the filters. In a particular embodiment, the excitation filter wheel provides a number of spectral filters:

Filter 1: A filter with a center wavelength of 485 nm and a spectral bandwidth of 20 nm;

Filter 2: A filter with a center wavelength of 530 nm and a spectral bandwidth of 20 nm; and Filter 3: A filter with a center wavelength of 580 nm and a spectral bandwidth of 20 nm.

As will be evident to one of skill in the art, embodiments of the present invention are not limited to these particular spectral filters, but will utilize spectral filters adapted for fluorescence processes for particular samples. Moreover, although the previous discussion related to the use of a filter wheel, this is not required by the present invention. In alternative embodiments, spectral filters are provided in geometries other than a wheel. For example, spectral filters that drop into a filter holder, electro-optic filters, filters placed into the optical path by actuators, and the like are included according to embodiments of the present invention. Moreover, in other embodiments, the optical source is a tunable laser adapted to emit radiation at predetermined wavelengths suitable for excitation of fluorescence. One of ordinary skill in the art would recognize many variations, modifications, and alternatives.

As illustrated in FIG. 22, excitation shutter 246 is provided according to embodiments of the present invention. The excitation shutter is operated under control of the computer 270 in some embodiments, to block/pass the optical signal generated by the optical source 242 and spectrally filtered by the excitation filter wheel 244. Depending on the application, the excitation source is blocked while samples are inserted and removed from the system as well as for calibration operations. In some embodiments, the excitation shutter is not utilized, for example, in embodiments utilizing laser sources, which provide alternative means to extinguish the optical source.

When the excitation shutter is operated in an open position, the optical excitation signal passes through a fiber bundle 248 and is directed so as to impinge on a microfluidic device 205 provided in chip carrier 207. Other embodiments of the present invention utilize quartz light guides, liquid light guides, other scrambling systems, and the like to increase illumination homogeneity. As illustrated in FIG. 22, the excitation optical signal is directed, through reflection by optical illuminator 250, refraction, or combinations thereof, to impinge on a surface of the microfluidic device 205. As illustrated in FIG. 22, illumination of the microfluidic device is via optical illuminator 250. In other embodiments illumination maybe coupled to the microfluidic device obliquely from one or more sides of device, via a ring light, or via a portion of the collection optical train (the optical path between the microfluidic device and the detector 260.

In some embodiments, the illumination of the microfluidic device with light produced by the excitation source is provided over a two-dimensional area of the sample. In these embodiments, a large field of view is provided, which enables the performance of fluorescence applications that involve imaging of time resolved chemical processes and reactions. As an example, fluorescent imaging of protein calorimetry and nucleic acid amplification processes are time resolved processes that benefit from embodiments of the present invention. In some of these processes, simultaneously excitation of the fluorescent samples provided in a number of reaction chambers and simultaneous collection of the fluorescent signals produced by the reactions occurring in the number of reaction chambers is desirable. In other processes, for instance, fluorescence lifetime imaging, a brief excitation pulse is followed by detection (and analysis) of the fluorescent signal as it decays in time from an initial level. One of ordinary skill in the art would recognize many variations, modifications, and alternatives.

As an example, nucleic acid amplification processes typically include the target DNA, a thermostable DNA polymerase, two oligonucleotide primers, deoxynucleotide triphosphates (dNTPs), a reaction buffer, and magnesium. Once assembled, the reaction is placed in a thermal cycler, an instrument that subjects the reaction to a series of different temperatures for varying amounts of time. This series of temperature and time adjustments is referred to as one cycle of amplification. Each cycle theoretically doubles the amount of targeted sequence (amplicon) in the reaction. Ten cycles theoretically multiply the amplicon by a factor of about one thousand; 20 cycles, by a factor of more than a million in a matter of hours. In some applications, it is desirable to acquire fluorescent imaging data from a large area (e.g., on the order of several $cm^2$) in a time period ranging from seconds to minutes.

In some embodiments of the present invention, the methods and systems provided by embodiments of the present invention facilitate image capture processes that are performed in a predetermined time period. Merely by way of example, in an embodiment of the present invention a method of imaging microfluidic devices is provided. The method includes capturing an image of a spatial region associated with at least a determined number of chambers of a microfluidic device using an image detection spatial region during a time frame of less than one minute, whereupon the capturing of the image of the spatial region is substantially free from a stitching and/or scanning process.

Embodiments of the present invention provide a variety of time frames for image capture, ranging from 1 millisecond to 1 minute. In some embodiments, time frames for image capture are greater than one minute. Depending on the emission properties associated with the processes performed in the chambers of the microfluidic device, the time frame for image capture will vary. For example, in an embodiment, the time frame is 10 ms, 50 ms, 100 ms, 250 ms, 500 ms, 750 ms, or 1 second. In other embodiments, the time frame is 2 seconds, 5 seconds, 10 seconds, 15 seconds, 20 seconds, 30 seconds, 40 seconds, 50 seconds, or 1 minute. Of course, the time frame will depend on the particular applications.

In some embodiments, the image capture process is performed in a synchronous manner, capturing an image of a determined number of chambers simultaneously. As an example, in an exemplary PCR process, the microfluidic device is maintained at a temperature of 90° C. for a time period of 15 seconds. Subsequently, the microfluidic device is maintained at a temperature of 60° C. for 45 seconds. The heating and cooling cycle is repeated at a one minute cycle period for a number of cycles. Utilizing embodiments of the present invention, images of a determined number of chambers present in the microfluidic device are acquired synchronously, while the chambers are maintained at a uniform temperate as a function of position. For example, a two-dimensional image of an entire microfluidic device may be acquired utilizing a 30 second exposure while the microfluidic device is maintained at the temperature of 60° C. One of skill in the art will appreciate the benefits provided by the present invention over raster scanning or stitching systems, in which images of chambers in a first portion (e.g., an upper left quadrant) of the microfluidic device are acquired prior to images of chambers in a second portion (e.g., a lower right quadrant) of the microfluidic device.

In other embodiments, multiple images are acquired of the determined number of chambers during a time frame of less than one minute. As an example of these embodiments, multiple images associated with multiple fluorophores are acquired in a particular embodiment. During the 45 second time period during which the microfluidic device is maintained at the temperature of 60° C., three consecutive images utilizing exposures of 15 seconds may be acquired for three different fluorophores, for example, Rox™, Vic®, and Fam™. Utilizing these multiple images, differential fluorescence ratios can be calculated and analyzed. Of course, depending on the strength of the fluorescent emissions, the exposure times for the various fluorophores may be modified as appropriate the particular application. In this way, embodiments of the present invention provide for imaging of a microfluidic device in multiple spectral bands while the microfluidic device is maintained a constant temperature. The constant temperature, as illustrated by the previous example, may be a portion of a PCR process including cyclical temperature processes.

Embodiments of the present invention provide methods and systems are also adapted to perform and analyze chemiluminescence processes. In some of these processes, reactions occur on a first time scale and an image of the chemiluminescence process is acquired on a second time scale. In a particular process, the second time scale is less than the first time scale. Thus, embodiments of the present invention are adapted to capture synchronous images of chemiluminescence processes when the samples in the reaction chambers of interest have been reacting for an equal amount of time. In some of these processes, temperature control, including temperature cycling of the samples is provided, whereas in other embodiments, the reaction chambers are maintained at a constant temperature.

As illustrated in FIG. 22, a thermal controller, also referred to as a temperature controller, 240 is provided according to embodiments of the present invention. A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of channels of a microfluidic device).

When microfluidic device 205 is illuminated, the illumination radiation may be reflected by numerous features of microfluidic device 205. Reflective features can include flow channels, vents, valves, etc., which are typically primarily oriented along two mutually perpendicular directions. Reflective features can also include any other feature that reflects light to any significant degree. Reflected illumination radiation may interfere with the image capture process by adding undesirable reflected illumination radiation to the desired fluorescent signal as seen in the imaging direction. Typically, the imaging direction is generally perpendicular to the microfluidic device, although other imaging directions may be practiced.

Embodiments of the present invention provide methods and systems with reduced imaging interference from reflected illumination radiation. By reducing the amount of illumination radiation that is reflected in the imaging direction, the image capture process is improved. In some embodiments, the use of an illumination direction that produces a significant amount of reflected illumination in the imaging direction is avoided. This can be accomplished by avoiding illumination directions that align with primary feature directions of the microfluidic device 205. This suppresses high-efficiency reflection paths, and effectively reduces the brightness of unwanted clutter in fluorescent images.

Figure 23B:
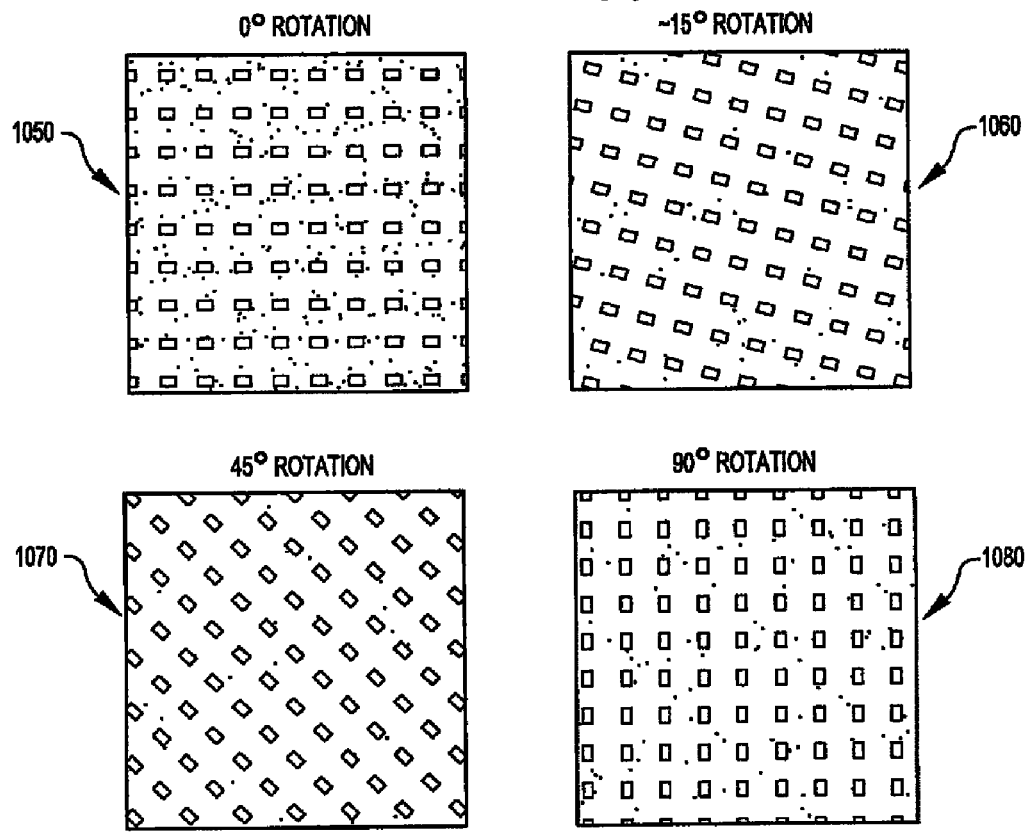
FIG. 23B shows additional reflection test results using illumination in accordance with embodiments of the present invention.

FIGS. 23A and 23B show results for reflection tests using illumination in accordance with embodiments of the present invention. Each of these figures shows test results for a microfluidic device for four illumination directions. The images shown in these figures were obtained by rotating the microfluidic chip relative to the illumination direction by the indicated amount, thereby producing illumination from an illumination direction with an azimuth of the indicated amount relative to a primary feature direction of the microfluidic device. The images were obtained from the imaging direction. These images qualitatively demonstrate the impact that illumination direction has upon the amount of unwanted reflections as seen from the imaging direction. As can be seen in image 1010 of FIG. 23A and image 1050 of FIG. 23B, when microfluidic device 205 is positioned at zero degree azimuth relative to the illumination direction, the resulting images contain notable amounts of reflective clutter from areas adjacent to the rectangular reaction sites. As can be seen in image 1040 of FIG. 23A and image 1080 of FIG. 23B, when microfluidic device 205 is positioned at 90 degree azimuth relative to the illumination direction, the resulting images also contain notable amounts of reflective clutter. As can be seen in image 1020 of FIG. 23A and image 1060 of FIG. 23B, when microfluidic device 205 is positioned at 15 degree azimuth relative to the illumination direction, the resulting images contain reduced amounts of reflective clutter as compared to the zero degree and 90 degree azimuth images. As can be seen in image 1030 of FIG. 23A and image 1070 of FIG. 23B, when microfluidic device 205 is positioned at 45 degree azimuth relative to the illumination direction, the resulting images contain the least amount of reflective clutter as compared to the other images.

There are several ways to reduce the amount of reflective clutter in the resulting image. For example, the illumination direction can be varied in both azimuth and elevation relative to the microfluidic device so as to reduce unwanted reflective clutter in the resulting image. As a further example, microfluidic device features can be designed with reflection characteristics in mind so as to minimize the amount of reflections produced, and/or minimize the amount of reflections directed in the imaging direction.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. An apparatus for supplying controlled pressure to a microfluidic device, the apparatus comprising:
   a holder configured to couple with a microfluidic device, the microfluidic device having a plurality of reaction cells;
   a plurality of accumulators for supplying controlled pressure to the microfluidic device; and
   a pressure regulator for selectively regulating pressure supplied to each of the plurality of accumulators.

2. The apparatus of claim 1, wherein the pressure regulator comprises an accumulator selector valve.

3. The apparatus of claim 1, wherein the pressure regulator employs rotary motion.

4. The apparatus of claim 1, further comprising one or more first supply outlet selector valves for selectively placing a first supply outlet in fluid communication with one of the plurality of accumulators.

5. The apparatus of claim 4, further comprising one or more second supply outlet selector valves for selectively placing a second supply outlet in fluid communication with one of the plurality of accumulators.

6. The apparatus of claim 5, wherein the pressure regulator comprises an accumulator selector valve.

7. The apparatus of claim 6, wherein the pressure regulator employs rotary motion.

8. The apparatus of claim 5, wherein one or more of the first supply outlet selector valves comprise a rotary valve, and wherein one or more of the second supply outlet selector valves comprise a rotary valve.

9. A system for supplying controlled pressure to a microfluidic device, the system comprising:
   a holder configured to couple with a microfluidic device, the microfluidic device having a plurality of reaction cells;
   a plurality of accumulators for supplying controlled pressure to the microfluidic device;
   a pressure regulator for selectively regulating pressure supplied to each of the plurality of accumulators; and
   a control unit for controlling the operation of the pressure regulator.

10. The system of claim 9, wherein the pressure regulator comprises an accumulator selector valve.

11. The system of claim 9, wherein the pressure regulator employs rotary motion.

12. The system of claim 9, further comprising one or more first supply outlet selector valves for selectively placing a first supply outlet in fluid communication with one of the plurality of accumulators.

13. The system of claim 12, further comprising one or more second supply outlet selector valves for selectively placing a second supply outlet in fluid communication with one of the plurality of accumulators.

14. The system of claim 13, wherein the pressure regulator comprises an accumulator selector valve.

15. The system of claim 14, wherein the pressure regulator employs rotary motion.

16. The system of claim 13, wherein one or more of the first supply outlet selector valves comprise a rotary valve, and wherein one or more of the second supply outlet selector valves comprise a rotary valve.

* * * * *